US009110025B2

(12) United States Patent  (10) Patent No.: US 9,110,025 B2
Rissin et al.  (45) Date of Patent: Aug. 18, 2015

(54) METHODS AND SYSTEMS FOR EXTENDING DYNAMIC RANGE IN ASSAYS FOR THE DETECTION OF MOLECULES OR PARTICLES

(75) Inventors: David M. Rissin, Somerville, MA (US); David Fournier, Northborough, MA (US); David C. Duffy, Arlington, MA (US)

(73) Assignee: Quanterix Corporation, Lexington, MA (US)

(*) Notice: Subject to any disclaimer, the term of this patent is extended or adjusted under 35 U.S.C. 154(b) by 1153 days.

(21) Appl. No.: 13/037,987

(22) Filed: Mar. 1, 2011

(65) Prior Publication Data

US 2011/0245097 A1  Oct. 6, 2011

Related U.S. Application Data

(63) Continuation-in-part of application No. 12/731,136, filed on Mar. 24, 2010, now Pat. No. 8,415,171.

(60) Provisional application No. 61/309,165, filed on Mar. 1, 2010, provisional application No. 61/441,894, filed on Feb. 11, 2011.

(51) Int. Cl.
  *C12Q 1/68* (2006.01)
  *G01N 21/64* (2006.01)
  *G01N 33/543* (2006.01)

(52) U.S. Cl.
  CPC ...... *G01N 21/6452* (2013.01); *G01N 33/54313* (2013.01); *G01N 33/54366* (2013.01)

(58) Field of Classification Search
  None
  See application file for complete search history.

(56) References Cited

U.S. PATENT DOCUMENTS

| 3,712,986 | A |   | 1/1973  | Collings        |
|-----------|---|---|---------|-----------------|
| 4,200,110 | A |   | 4/1980  | Peterson et al. |
| 4,232,119 | A |   | 11/1980 | Carlsson et al. |
| 4,631,211 | A |   | 12/1986 | Houghten        |
| 4,780,421 | A | * | 10/1988 | Kameda et al. ............... 436/518 |
| 4,883,642 | A |   | 11/1989 | Bisconte        |
| 4,907,037 | A |   | 3/1990  | Boisde et al.   |
| 4,924,870 | A |   | 5/1990  | Wlodarczyk et al. |
| 4,962,037 | A |   | 10/1990 | Jett et al.     |
| 5,026,159 | A |   | 6/1991  | Allen et al.    |
| 5,028,535 | A |   | 7/1991  | Buechler et al. |
| 5,089,391 | A |   | 2/1992  | Buechler et al. |
| 5,091,300 | A |   | 2/1992  | Hurni et al.    |
| 5,108,961 | A |   | 4/1992  | Zhong et al.    |
| 5,152,816 | A |   | 10/1992 | Berkey          |
| 5,190,857 | A |   | 3/1993  | Allen et al.    |
| 5,196,306 | A |   | 3/1993  | Bobrow et al.   |
| 5,244,636 | A |   | 9/1993  | Walt et al.     |
| 5,244,813 | A |   | 9/1993  | Walt et al.     |
| 5,250,264 | A |   | 10/1993 | Walt et al.     |
| 5,252,494 | A |   | 10/1993 | Walt            |
| 5,298,741 | A |   | 3/1994  | Walt et al.     |
| 5,315,375 | A |   | 5/1994  | Allen           |
| 5,320,814 | A |   | 6/1994  | Walt et al.     |
| 5,329,461 | A |   | 7/1994  | Allen et al.    |
| 5,374,395 | A |   | 12/1994 | Robinson et al. |
| 5,405,783 | A |   | 4/1995  | Pirrung et al.  |
| 5,445,934 | A |   | 8/1995  | Fodor et al.    |
| 5,468,846 | A |   | 11/1995 | Ichikawa et al. |
| 5,488,567 | A |   | 1/1996  | Allen et al.    |
| 5,512,490 | A |   | 4/1996  | Walt et al.     |
| 5,532,138 | A |   | 7/1996  | Singh et al.    |
| 5,532,379 | A |   | 7/1996  | Fujimoto        |
| 5,545,531 | A |   | 8/1996  | Rava et al.     |
| 5,583,001 | A |   | 12/1996 | Bobrow et al.   |
| 5,620,850 | A |   | 4/1997  | Bamdad et al.   |
| 5,633,972 | A |   | 5/1997  | Walt et al.     |
| 5,690,894 | A |   | 11/1997 | Pinkel et al.   |
| 5,700,637 | A |   | 12/1997 | Southern        |
| 5,731,158 | A |   | 3/1998  | Bobrow et al.   |
| 5,770,455 | A |   | 6/1998  | Cargill et al.  |
| 5,807,522 | A |   | 9/1998  | Brown et al.    |
| 5,814,524 | A |   | 9/1998  | Walt et al.     |
| 5,885,529 | A | * | 3/1999  | Babson et al. .................. 422/65 |

(Continued)

FOREIGN PATENT DOCUMENTS

| AU | 199956253 B2 | 3/2000 |
|----|--------------|--------|
| CN | 1635146 A    | 7/2005 |

(Continued)

OTHER PUBLICATIONS

International Preliminary Report on Patentability for PCT/US2012/022923 mailed Aug. 8, 2013.
Office Action for U.S. Appl. No. 13/527,210, filed Jun. 19, 2012, which Office Action is dated Feb. 6, 2014, and claims as pending for Office Action for U.S. Appl. No. 13/527,210 as of Nov. 20, 2013.
Notice of Allowance for U.S. Appl. No. 13/527,210, filed Jun. 19, 2012, which Notice of Allowance is dated May 27, 2014, and claims as pending for U.S. Appl. No. 13/527,210 as of Nov. 20, 2013.
Office Communication for U.S. Appl. No. 13/035,472, filed Feb. 25, 2011, which Office Communication is dated Mar. 20, 2014, and claims as pending for U.S. Appl. No. 13/035,472.
International Search Report and Written Opinion for International Application No. PCT/US2009/005250, mailed Mar. 22, 2010.

(Continued)

*Primary Examiner* — Ann Lam
(74) *Attorney, Agent, or Firm* — Wolf, Greenfield & Sacks, P.C.

(57) ABSTRACT

Described herein are systems and methods for extending the dynamic range of assay methods and systems used for determining the concentration of analyte molecules or particles in a fluid sample. In some embodiments, a method comprises spatially segregating a plurality of analyte molecules in a fluid sample into a plurality of locations. At least a portion of the locations may be addressed to determine the percentage of said locations containing at least one analyte molecule. Based at least in part on the percentage, a measure of the concentration of analyte molecules in the fluid sample may be determined using an analog, intensity-based detection/analysis method/system and/or a digital detection/analysis method/system. In some cases, the assay may comprise the use of a plurality of capture objects.

17 Claims, 14 Drawing Sheets

(56) References Cited

U.S. PATENT DOCUMENTS

| | | | |
|---|---|---|---|
| 5,900,481 A | 5/1999 | Lough et al. | |
| 5,981,180 A | 11/1999 | Chandler et al. | |
| 6,001,564 A | 12/1999 | Bergeron et al. | |
| 6,007,690 A | 12/1999 | Nelson et al. | |
| 6,013,445 A | 1/2000 | Albrecht et al. | |
| 6,023,540 A | 2/2000 | Walt et al. | |
| 6,133,436 A | 10/2000 | Koster et al. | |
| 6,143,496 A | 11/2000 | Brown et al. | |
| 6,156,270 A | 12/2000 | Buechler | |
| 6,174,695 B1 | 1/2001 | Hammock et al. | |
| 6,210,910 B1 | 4/2001 | Walt et al. | |
| 6,266,459 B1 | 7/2001 | Walt et al. | |
| 6,285,807 B1 | 9/2001 | Walt et al. | |
| 6,327,410 B1 | 12/2001 | Walt et al. | |
| 6,329,139 B1 | 12/2001 | Nova et al. | |
| 6,368,874 B1 | 4/2002 | Gallop et al. | |
| 6,377,721 B1 | 4/2002 | Walt et al. | |
| 6,388,746 B1 | 5/2002 | Eriksson et al. | |
| 6,396,995 B1 | 5/2002 | Stuelpnagel et al. | |
| 6,406,845 B1 | 6/2002 | Walt et al. | |
| 6,432,630 B1* | 8/2002 | Blankenstein | 435/4 |
| 6,482,593 B2 | 11/2002 | Walt et al. | |
| 6,582,908 B2 | 6/2003 | Fodor et al. | |
| 6,602,702 B1* | 8/2003 | McDevitt et al. | 435/288.7 |
| 6,620,584 B1 | 9/2003 | Chee et al. | |
| 6,635,452 B1 | 10/2003 | Monforte et al. | |
| 6,667,159 B1 | 12/2003 | Walt et al. | |
| 6,713,309 B1 | 3/2004 | Anderson et al. | |
| 6,714,303 B2 | 3/2004 | Ivarsson | |
| 6,821,449 B2 | 11/2004 | Caplen et al. | |
| 6,838,051 B2 | 1/2005 | Marquiss et al. | |
| 6,858,394 B1 | 2/2005 | Chee et al. | |
| 6,859,570 B2 | 2/2005 | Walt | |
| 6,878,345 B1 | 4/2005 | Astle | |
| 6,929,924 B2 | 8/2005 | Bouanani et al. | |
| 6,942,968 B1 | 9/2005 | Dickinson et al. | |
| 6,943,034 B1 | 9/2005 | Winkler et al. | |
| 6,991,939 B2 | 1/2006 | Walt et al. | |
| 6,999,657 B2 | 2/2006 | Walt | |
| 7,056,746 B2 | 6/2006 | Seul et al. | |
| 7,060,431 B2 | 6/2006 | Chee et al. | |
| 7,115,884 B1 | 10/2006 | Walt et al. | |
| 7,211,390 B2 | 5/2007 | Rothberg et al. | |
| 7,244,559 B2 | 7/2007 | Rothberg et al. | |
| 7,250,267 B2 | 7/2007 | Walt et al. | |
| 7,264,929 B2 | 9/2007 | Rothberg et al. | |
| 7,348,181 B2 | 3/2008 | Walt et al. | |
| 7,480,433 B2 | 1/2009 | Walt et al. | |
| 7,572,581 B2 | 8/2009 | Gelfand et al. | |
| 7,651,841 B2 | 1/2010 | Song et al. | |
| 7,759,062 B2 | 7/2010 | Allawi et al. | |
| 7,776,553 B2 | 8/2010 | Love et al. | |
| 7,838,250 B1 | 11/2010 | Goix et al. | |
| 8,222,047 B2* | 7/2012 | Duffy et al. | 436/518 |
| 8,236,574 B2* | 8/2012 | Duffy et al. | 436/518 |
| 8,415,171 B2* | 4/2013 | Rissin et al. | 436/518 |
| 8,460,878 B2 | 6/2013 | Walt et al. | |
| 8,460,879 B2 | 6/2013 | Walt et al. | |
| 8,492,098 B2 | 7/2013 | Walt et al. | |
| 8,846,415 B2* | 9/2014 | Duffy et al. | 436/518 |
| 2002/0009391 A1 | 1/2002 | Marquiss et al. | |
| 2002/0090650 A1 | 7/2002 | Empedocles et al. | |
| 2002/0122612 A1 | 9/2002 | Walt et al. | |
| 2003/0027126 A1 | 2/2003 | Walt et al. | |
| 2003/0091475 A1 | 5/2003 | Yu et al. | |
| 2003/0104361 A1 | 6/2003 | Weininger et al. | |
| 2003/0198573 A1 | 10/2003 | Forood et al. | |
| 2004/0038426 A1 | 2/2004 | Manalis | |
| 2004/0053322 A1 | 3/2004 | McDevitt et al. | |
| 2004/0071599 A1 | 4/2004 | Rusch et al. | |
| 2004/0072278 A1 | 4/2004 | Chou et al. | |
| 2004/0086426 A1 | 5/2004 | Vann et al. | |
| 2004/0101918 A1 | 5/2004 | Cauci | |
| 2004/0142386 A1 | 7/2004 | Rigler et al. | |
| 2004/0248325 A1* | 12/2004 | Bukusoglu | 436/548 |
| 2004/0253624 A1 | 12/2004 | Smith et al. | |
| 2004/0259237 A1 | 12/2004 | Kellogg et al. | |
| 2005/0112655 A1 | 5/2005 | Banerjee et al. | |
| 2005/0130173 A1 | 6/2005 | Leamon et al. | |
| 2005/0130188 A1 | 6/2005 | Walt et al. | |
| 2005/0131650 A1 | 6/2005 | Andersson et al. | |
| 2005/0164289 A1 | 7/2005 | Quate et al. | |
| 2005/0226780 A1 | 10/2005 | Sandell et al. | |
| 2005/0244308 A1 | 11/2005 | Tanaami et al. | |
| 2005/0266433 A1 | 12/2005 | Kapur et al. | |
| 2006/0006067 A1 | 1/2006 | Unger | |
| 2006/0013543 A1 | 1/2006 | Walt et al. | |
| 2006/0040297 A1 | 2/2006 | Leamon et al. | |
| 2006/0068409 A1 | 3/2006 | Phan et al. | |
| 2006/0078998 A1 | 4/2006 | Puskas et al. | |
| 2006/0084183 A1 | 4/2006 | Henricksen | |
| 2006/0139635 A1 | 6/2006 | Kersey et al. | |
| 2007/0040095 A1 | 2/2007 | Walt et al. | |
| 2007/0074972 A1 | 4/2007 | Nassef et al. | |
| 2007/0116607 A1 | 5/2007 | Wang et al. | |
| 2007/0259381 A1 | 11/2007 | Walt et al. | |
| 2007/0259385 A1 | 11/2007 | Walt et al. | |
| 2007/0259448 A1 | 11/2007 | Walt et al. | |
| 2008/0032324 A1 | 2/2008 | Walt et al. | |
| 2008/0064115 A1 | 3/2008 | Goix | |
| 2009/0036324 A1 | 2/2009 | Fan et al. | |
| 2009/0142755 A1 | 6/2009 | Albitar | |
| 2009/0149341 A1 | 6/2009 | Walt et al. | |
| 2009/0156425 A1 | 6/2009 | Walt et al. | |
| 2009/0170728 A1 | 7/2009 | Walt et al. | |
| 2009/0239308 A1 | 9/2009 | Dube et al. | |
| 2009/0254180 A1 | 10/2009 | Pazanowski | |
| 2009/0289834 A1 | 11/2009 | Devensky | |
| 2009/0307772 A1 | 12/2009 | Markham | |
| 2010/0075355 A1* | 3/2010 | Duffy et al. | 435/18 |
| 2010/0075407 A1 | 3/2010 | Duffy et al. | |
| 2010/0075439 A1* | 3/2010 | Duffy et al. | 436/518 |
| 2010/0075862 A1 | 3/2010 | Duffy et al. | |
| 2010/0140289 A1 | 6/2010 | Knobel et al. | |
| 2010/0189338 A1 | 7/2010 | Lin et al. | |
| 2010/0192573 A1 | 8/2010 | Hamilton et al. | |
| 2010/0204335 A1 | 8/2010 | Beddingfield et al. | |
| 2011/0183330 A1 | 7/2011 | Lo et al. | |
| 2011/0195852 A1 | 8/2011 | Walt et al. | |
| 2011/0212462 A1* | 9/2011 | Duffy et al. | 435/7.1 |
| 2011/0212537 A1 | 9/2011 | Duffy et al. | |
| 2011/0212848 A1 | 9/2011 | Duffy et al. | |
| 2012/0196774 A1 | 8/2012 | Fournier et al. | |
| 2012/0214160 A1 | 8/2012 | Deng et al. | |
| 2012/0277114 A1* | 11/2012 | Duffy et al. | 506/9 |
| 2012/0289428 A1* | 11/2012 | Duffy et al. | 506/9 |
| 2013/0165342 A1* | 6/2013 | Rissin et al. | 506/9 |
| 2013/0345078 A1 | 12/2013 | Walt et al. | |
| 2014/0094386 A1 | 4/2014 | Wilson et al. | |

FOREIGN PATENT DOCUMENTS

| | | |
|---|---|---|
| DE | 19540098 A1 | 4/1997 |
| EP | 0 805 215 A2 | 11/1997 |
| EP | 1 180 679 A1 | 2/2002 |
| EP | 1 259 810 B1 | 11/2006 |
| EP | 1 721 657 A1 | 11/2006 |
| EP | 2 267 451 A2 | 12/2010 |
| JP | 2001-269196 A | 10/2001 |
| JP | 2002-506200 A | 2/2002 |
| JP | 2002-525587 A | 8/2002 |
| JP | 2002-526743 A | 8/2002 |
| JP | 2004-354164 A | 12/2004 |
| JP | 2005-518553 A | 6/2005 |
| JP | 2006-511792 A | 4/2006 |
| WO | WO 88/05533 A1 | 7/1988 |
| WO | WO 93/06121 A1 | 4/1993 |
| WO | WO 93/24517 A2 | 12/1993 |
| WO | WO 95/25116 A1 | 9/1995 |
| WO | WO 95/32425 A1 | 11/1995 |
| WO | WO 95/35506 A2 | 12/1995 |
| WO | WO 97/27326 A1 | 7/1997 |
| WO | WO 98/50782 A2 | 11/1998 |
| WO | WO 99/45357 A2 | 9/1999 |

(56) References Cited

FOREIGN PATENT DOCUMENTS

| WO | WO 99/58948 A2 | 11/1999 |
|---|---|---|
| WO | WO 00/04372 A1 | 1/2000 |
| WO | WO 00/47996 A2 | 8/2000 |
| WO | WO 01/57520 A2 | 8/2001 |
| WO | WO 03/054142 A2 | 7/2003 |
| WO | WO 03/073817 A1 | 9/2003 |
| WO | WO 2004/065000 A1 | 8/2004 |
| WO | WO 2004/083443 A1 | 9/2004 |
| WO | WO 2005/019419 A2 | 3/2005 |
| WO | WO 2005/023414 A1 | 3/2005 |
| WO | WO 2005/033283 A2 | 4/2005 |
| WO | WO 2005/054431 A2 | 6/2005 |
| WO | WO 2006/007726 A1 | 1/2006 |
| WO | WO 2006/055739 A2 | 5/2006 |
| WO | WO 2006/078289 A2 | 7/2006 |
| WO | WO 2006/102297 A1 | 9/2006 |
| WO | WO 2006/108180 A2 | 10/2006 |
| WO | WO 2007/044091 A2 | 4/2007 |
| WO | WO 2007/044974 A2 | 4/2007 |
| WO | WO 2007/081385 A2 | 7/2007 |
| WO | WO 2007/081386 A2 | 7/2007 |
| WO | WO 2007/081387 A1 | 7/2007 |
| WO | WO 2007/084192 A2 | 7/2007 |
| WO | WO 2007/098148 A2 | 8/2007 |
| WO | WO 2007/114947 A2 | 10/2007 |
| WO | WO 2008/048371 A2 | 4/2008 |
| WO | WO 2009/029073 A1 | 3/2009 |
| WO | WO 2010/039180 A2 | 4/2010 |
| WO | WO 2011/109372 A1 | 9/2011 |

OTHER PUBLICATIONS

International Preliminary Report on Patentability, Chapter 1, for International Application No. PCT/US2009/005250, mailed Apr. 7, 2011.
International Search Report and Written Opinion for International Application No. PCT/US2009/005248, mailed Mar. 1, 2010.
International Preliminary Report on Patentability, Chapter 1, for International Application No. PCT/US2009/005248, mailed Apr. 7, 2011.
International Search Report and Written Opinion for International Application No. PCT/US2011/026645, mailed Nov. 24, 2011.
International Preliminary Report on Patentability for PCT/US2011/026645 mailed Sep. 13, 2012.
International Search Report and Written Opinion for International Application No. PCT/US2011/026657, mailed May 24, 2011.
International Preliminary Report on Patentability for PCT/US2011/026657 mailed Sep. 13, 2012.
International Search Report and Written Opinion for International Application No. PCT/US2011/026665, mailed Jul. 5, 2011.
International Preliminary Report on Patentability for PCT/US2011/026665 mailed Sep. 13, 2012.
Invitation to Pay Additional Fees for PCT/US2012/022923 mailed Apr. 2, 2012.
International Search Report and Written Opinion for International Application No. PCT/US2012/022923 mailed Jun. 25, 2012.
International Search Report and Written Opinion for International Application No. PCT/US2007/019184, mailed Jun. 19, 2008.
International Preliminary Report on Patentability, Chapter 1, for International Application No. PCT/US2007/019184, mailed Mar. 11, 2010.
European Search Report for European Application No. 07751131.9, mailed Sep. 8, 2009.
Extended European Search Report for European Application No. 12177276.8 mailed Nov. 26, 2012.
International Search Report and Written Opinion for International Application No. PCT/US2007/004349, mailed Aug. 21, 2008.
International Preliminary Report on Patentability, Chapter 1, for International Application No. PCT/US2007/004349 dated Sep. 25, 2008.
International Preliminary Report on Patentability, Chapter 2, for International Application No. PCT/US2007/004349 dated Mar. 23, 2009.
Office Action for U.S. Appl. No. 12/236,484, filed Sep. 23, 2008, published as US 2010-0075862 on Mar. 25, 2010, which Office Action is dated Sep. 9, 2010, and claims as pending for U.S. Appl. No. 12/236,484 as of Sep. 9, 2010.
Office Action for U.S. Appl. No. 12/236,484, filed Sep. 23, 2008, published as US 2010-0075862 on Mar. 25, 2010, which Office Action is dated Apr. 13, 2011, and claims as pending for U.S. Appl. No. 12/236,484 as of Apr. 13, 2011.
Office Action for U.S. Appl. No. 12/236,486, filed Sep. 23, 2008, published as US 2010-0075407 on Mar. 25, 2010, which Office Action is dated Nov. 23, 2011, and claims as pending for U.S. Appl. No. 12/236,486 as of Nov. 23, 2011.
Notice of Allowance for U.S. Appl. No. 12/236,486, filed Sep. 23, 2008, published as US-2010-0075407 on Mar. 25, 2010, which Notice of Allowance is dated Mar. 22, 2012, and claims as allowed for U.S. Appl. No. 12/236,486 as of Mar. 25, 2010.
Office Action for U.S. Appl. No. 13/527,210, filed Jun. 19, 2012, which Office Action is dated Jun. 20, 2013, and claims as pending for Office Action for U.S. Appl. No. 13/527,210 as of Jun. 20, 2013.
Office Action for U.S. Appl. No. 12/236,488, filed Sep. 23, 2008, published as US 2010-0075439 on Mar. 25, 2010, which Office Action is dated Aug. 2, 2010, and claims as pending for U.S. Appl. No. 12/236,488 as of Aug. 2, 2010.
Office Action for U.S. Appl. No. 12/731,130, filed Mar. 24, 2010, published as US 2011-0212848 on Sep. 1, 2011, which Office Action is dated Mar. 28, 2012, and claims as pending for U.S. Appl. No. 12/731,130 as of Mar. 28, 2012.
Notice of Allowance for U.S. Appl. No. 12/731,130, filed Mar. 24, 2010, published as US 2011-0212848 on Sep. 1, 2011, which Notice of Allowance is dated Jun. 1, 2012, and allowed claims for U.S. Appl. No. 12/731,130 as of Jun. 1, 2012.
Office Action for U.S. Appl. No. 12/731,135, filed Mar. 24, 2010, published as US 20110212462 on Sep. 1, 2011, which Office Action is dated May 23, 2013, and claims as pending for U.S. Appl. No. 12/731,135 as of May 23, 2013.
Office Action for U.S. Appl. No. 12/731,136, filed Mar. 24, 2010, published as 2011-0212537 on Sep. 1, 2011, which Office Action is dated Jun. 15, 2012, and claims as pending for Office Action for U.S. Appl. No. 12/731,136 as of Jun. 15, 2012.
Notice of Allowance for U.S. Appl. No. 12/731,136, filed Mar. 24, 2010, published as 2011-0212537 on Sep. 1, 2011, which Notice of Allowance is dated Nov. 15, 2012, and claims as allowed for U.S. Appl. No. 12/731,136 as of Nov. 15, 2012.
Office Action for U.S. Appl. No. 11/707,385, filed Feb. 16, 2007, published as US 2007-0259448 on Nov. 8, 2007, which Office Action is dated Jan. 26, 2010, and claims as pending for U.S. Appl. No. 11/707,385 as of Jan. 26, 2010.
Office Action for U.S. Appl. No. 11/707,385, filed Feb. 16, 2007, published as US 2007-0259448 on Nov. 8, 2007, which Office Action is dated Mar. 16, 2009, and claims as pending for U.S. Appl. No. 11/707,385 as of Mar. 16, 2009.
Office Action for U.S. Appl. No. 11/707,385, filed Feb. 16, 2007, published as US 2007-0259448 on Nov. 8, 2007, which Office Action is dated Sep. 27, 2012, and claims as pending for U.S. Appl. No. 11/707,385 as of Sep. 27, 2012.
Notice of Allowance for U.S. Appl. No. 11/707,385, filed Feb. 16, 2007, published as US-2007-0259448 on Nov. 8, 2007, which Notice of Allowance is dated Feb. 25, 2013, and claims as allowed for Office Action for U.S. Appl. No. 11/707,385 as of Feb. 25, 2013.
Office Action for U.S. Appl. No. 11/707,383, filed Feb. 16, 2007, published as US 2007-0259385 on Nov. 8, 2007, which Office Action is dated Mar. 16, 2009, and claims as pending for U.S. Appl. No. 11/707,383 as of Mar. 16, 2009.
Office Action for U.S. Appl. No. 11/707,383, filed Feb. 16, 2007, published as US 2007-0259385 on Nov. 8, 2007, which Office Action is dated Nov. 27, 2009, and claims as pending for U.S. Appl. No. 11/707,383 as of Nov. 27, 2009.

(56) References Cited

OTHER PUBLICATIONS

Office Action for U.S. Appl. No. 11/707,383, filed Feb. 16, 2007, published as US 20070259385 on Nov. 8, 2007, which Office Action is dated Sep. 27, 2012, and claims as pending for U.S. Appl. No. 11/707,383 as of Sep. 27, 2012.

Notice of Allowance for U.S. Appl. No. 11/707,383, filed Feb. 16, 2007, published as US 2007-0259385 on Nov. 8, 2007, which Office Action is dated Feb. 8, 2013, and claims as allowed for U.S. Appl. No. 11/707,383 as of Feb. 8, 2013.

Office Action for U.S. Appl. No. 11/707,384, filed Feb. 16, 2007, published as US 2007-0259381 on Nov. 8, 2007, which Office Action is dated Mar. 16, 2009, and claims as pending for U.S. Appl. No. 11/707,384 as of Mar. 16, 2009.

Office Action for U.S. Appl. No. 11/707,384, filed Feb. 16, 2007, published as US 2007-0259381 on Nov. 8, 2007, which Office Action is dated Dec. 2, 2009, and claims as pending for U.S. Appl. No. 11/707,384 as of Dec. 2, 2009.

Office Action for U.S. Appl. No. 11/707,384, filed Feb. 16, 2007, published as US 2007-0259381 on Nov. 8, 2007, which Office Action is dated Sep. 27, 2012, and claims as pending for U.S. Appl. No. 11/707,384 as of Sep. 27, 2012.

Notice of Allowance for U.S. Appl. No. 11/707,384, filed Feb. 16, 2007, published as US 2007-0259381 on Nov. 8, 2007, which Office Action is dated Feb. 6, 2013, and claims as allowed for U.S. Appl. No. 11/707,384 as of Feb. 6, 2013.

[No Author Listed] Novel test following prostate surgery could detect cancer recurrence earlier. AACR Press Release. Sep. 29, 2010. Last accessed at http://www.aacr.org/home/public--media/aacr-press-releases.aspx?d=2072 on Jan. 31, 2012. 2 pages.

[No Author Listed] Quanterix corporation awarded $185,000 grant from the National Cancer Institute. Quanterix Press Release. Sep. 30, 2008. Last accessed at http://www.quanterix.com/news/pressReleases/SBIR1Grant.html on Jan. 31, 2012. 1 page.

[No Author Listed] Quanterix corporation raises $15 million in series A financing. Quanterix Press Release. Aug. 25, 2008. Last accessed at http://www.quanterix.com/news/pressReleases/seriesAFunding.html on Jan. 31, 2012. 2 pages.

[No Author Listed] Single molecule arrays for digital detection in complex samples. Quanterix Corporation. IQT Technology Focus Day. Mar. 25, 2010. PowerPoint presentation. 30 pages.

Adams et al., Encoded fiber-optic microsphere arrays for probing protein-carbohydrate interactions. Angewandte Chemie. 2003; 115:5475-5478.

Agrawal et al., Nanometer-scale mapping and single-molecule detection with color-coded nanoparticle probes. Proc Natl Acad Sci U S A. Mar. 4, 2008;105(9):3298-303. Epub Feb. 27, 2008.

Agrawal et al., Single-bead immunoassays using magnetic microparticles and spectral-shifting quantum dots. *J Agric Food Chem*. May 16, 2007; 55(10):3778-82. Epub Apr. 25, 2007.

Ahn et al., Detection of *Salmonella* spp. Using microsphere-based, fiber-optic DNA microarrays. Anal Chem. Aug. 1, 2005; 77(15):5041-7.

Ahn et al., Fiber-optic microarray for simultaneous detection of multiple harmful algal bloom species. Appl Environ Microbiol. Sep. 2006; 72(9):5742-9.

Albert et al., Automatic decoding of sensor types within randomly ordered, high-density optical sensor arrays. *Anal Bioanal Chem*. Apr. 2002; 373(8):792-802. Epub Jul. 27, 2002.

Albert et al., Cross-reactive chemical sensor arrays. *Chem Rev*. Jul. 12, 2000; 100(7):2595-626.

Albert et al., Information coding in artificial olfaction multisensor arrays. Anal Chem. Aug. 15, 2003; 75(16):4161-7.

Albert et al., Optical multibead arrays for simple and complex odor discrimination. *Anal Chem*. Jun. 1, 2001; 73(11):2501-8.

Angenendt et al., Subnanoliter enzymatic assays on microarrays. Proteomics. Feb. 2005;5(2):420-5.

Arnaud, Observing single enzymes at work. Chemical & Engineering News. Oct. 2007; 85(44): 8.

Beer et al., On-chip, real-time, single-copy polymerase chain reaction in picoliter droplets. Anal Chem. Nov. 15, 2007;79(22):8471-5. Epub Oct. 11, 2007. Abstract only.

Bencic-Nagale et al., Extending the longevity of fluorescence-based sensor arrays using adaptive exposure. Anal Chem. Oct. 1, 2005; 77(19):6155-62.

Bhat et al., Single molecule detection in nanofluidic digital array enables accurate measurement of DNA copy number. Anal Bioanal Chem. May 2009;394(2):457-67. Epub Mar. 15, 2009.

Biran et al., Optical imaging fiber-based live bacterial cell array biosensor. *Anal Biochem*. Apr. 1, 2003; 315(1):106-13.

Biran et al., Optical imaging fiber-based single live cell arrays: a high-density cell assay platform. *Anal Chem*. Jul. 1, 2002; 74(13):3046-54.

Blake et al., Phenotypic consequences of promoter-mediated transcriptional noise. Mol Cell. Dec. 28, 2006; 24(6):853-65.

Blicharz et al., Detection of inflammatory cytokines using a fiber optic microsphere immunoassay array. *Proc. SPIE*. 2006; 6380, 638010-1-638010-6.

Blicharz et al., Fiber-optic microsphere-based antibody array for the analysis of inflammatory cytokins in saliva. Anal. Chem. 2009;81(6):2106-14.

Blicharz et al., Use of colorimetric test strips for monitoring the effect of hemodialysis on salivary nitrite and uric acid in patients with end-stage renal disease: a proof of principle. Clin Chem. Sep. 2008; 54(9):1473-80. Epub Aug. 1, 2008.

Bourzac, Next-generation diagnostics: a startup can detect tiny traces of cancer markers in blood samples. Technol Rev. May 13, 2008. Last accessed at http://www.technologyreview.com/Biztech/20760/?a=f on Feb. 2, 2012. 2 pages.

Bowden et al., Development of a microfluidic platform with an optical imaging microarray capable of attomolar target DNA detection. Anal Chem. Sep. 1, 2005; 77(17):5583-8. Epub Aug. 4, 2005.

Boyden, The chemotactic effect of mixtures of antibody and antigen on polymorphonuclear leucocytes. J Exp Med. Mar. 1, 1962;115:453-66.

Brehm-Stecher et al., Single-cell microbiology: tools, technologies, and applications. *Microbiol Mol Biol Rev*. Sep. 2004; 68(3):538-59.

Brogan et al., Optical fiber-based sensors: application to chemical biology. Curr Opin Chem Biol. Oct. 2005; 9(5):494-500. Epub Aug. 24, 2005.

Bronk et al., Combined imaging and chemical sensing using a single optical imaging fiber. *Anal Chem*. Sep. 1, 1995; 67(17):2750-7.

Bronk et al., Fabrication of patterned sensor arrays with aryl azides on a polymer-coated imaging optical fiber bundle. *Anal Chem*. Oct. 15, 1994; 66(20):3519-20.

Burton et al., A microfluidic chip-compatible bioassay based on single-molecule detection with high sensitivity and multiplexing. *Lab Chip*. Apr. 7, 2010; 10(7):843-51. Epub Jan. 14, 2010.

Campian, Colored and fluorescent solid supports. Innovation and Perspectives in Solid Phase Synthesis. Ed. R. Epton, Mayflower Worldwide Limited, Birmingham. Ch. 77. 1994:469-472.

Chen et al., Microfabricated arrays of cylindrical wells facilitate single-molecule enzymology of alpha-chymotrypsin. *Biotechnol Prog*. Jul.-Aug. 2009; 25(4):929-37.

Chin et al., Editor's Choice: Distinctive individualism. Science. Apr. 4, 2008;320:21.

Chon et al., Characterization of single-cell migration using a computer-aided fluorescence time-lapse videomicroscopy system. Anal Biochem. Oct. 15, 1997;252(2):246-54.

Deutsch et al., Apparatus for high-precision repetitive sequential optical measurement of living cells. *Cytometry*. Jul. 1, 1994; 16(3):214-26.

Dicesare et al., Individual cell migration analysis using fiber-optic bundles. Anal Bioanal Chem. May 2005; 382(1):37-43. Epub Apr. 1, 2005.

Dickinson et al., A chemical-detecting system based on a cross-reactive optical sensor array. *Nature*. Aug. 22, 1996; 382(6593):697-700.

Dickinson et al., Convergent, self-encoded bead sensor arrays in the design of an artificial. *Anal Chem*. Jun. 1, 1999; 71(11):2192-8.

Dickinson et al., Current trends in 'artificial-nose' technology. *Trends Biotechnol*. Jun. 1998; 16(6):250-8.

(56) References Cited

OTHER PUBLICATIONS

Duffy. Single Molecule Arrays (Simoa) for Ultrasensitive Protein Detection in Companion Diagnostics. Next Generation DX Summit. Aug. 22, 2012. PowerPoint presentation.
Egner et al., Tagging in combinatorial chemistry: the use of coloured and flurorescent beads. Chem Commun. 1997; 735-736.
Eid et al., Real-time DNA sequencing from single polymerase molecules. *Science*. Jan. 2, 2009; 323(5910):133-8. Epub Nov. 20, 2008.
Ekins et al., Single-molecule ELISA. Clin Chem. Mar. 2011;57(3):372-5. Epub Oct. 13, 2010. Papers in press. Oct. 13, 2010. pp 1-3.
English et al., Ever-fluctuating single enzyme molecules: Michaelis-Menten equation revisited. Nat Chem Biol. Feb. 2006; 2(2):87-94. Epub Dec. 25, 2005.
Epstein et al., Combinatorial decoding: an approach for universal DNA array fabrication. *J Am Chem Soc*. Nov. 12, 2003; 125(45):13753-9.
Epstein et al., *Fluorescence-based nucleic acid detection and microarrays*. Analytica Chimica Acta. 2002; 469:3-36.
Epstein et al., High-density fiber-optic genosensor microsphere array capable of zeptomole detection limits. *Anal Chem*. Apr. 15, 2002; 74(8):1836-40.
Epstein et al., High-density, microsphere-based fiber optic DNA microarrays. *Biosens Bioelectron*. May 2003; 18(5-6):541-6.
Epstein, et al., Fluorescence-based fibre optic arrays: a universal platform for sensing. *Chem Soc Rev*. Jul. 2003; 32(4):203-14.
Ferguson et al., A fiber-optic DNA biosensor microarray for the analysis of gene expression. *Nat Biotechnol*. Dec. 1996; 14(13):1681-4.
Ferguson et al., High-density fiber-optic DNA random microsphere array. *Anal Chem*. Nov. 15, 2000; 72(22):5618-24.
Ferguson et al., Simultaneous monitoring of pH, $CO_2$ and $O_2$ using an optical imaging fiber. Analytica Chimica Acta. 1997; 340(1-3):123-131.
Fister et al., Counting single chromophore molecules for ultrasensitive analysis and separations on microchip devices. Analytical Chemistry. 1998; 70:431-437.
Fulton et al., Advanced multiplexed analysis with the FlowMetrix system. *Clin Chem*. Sep. 1997; 43(9):1749-56.
Furka et al., General method for rapid synthesis of multicomponent peptide mixtures. Int J Pept Protein Res. Jun. 1991;37(6):487-93.
Gebel, Molecule counting made easy. Anal Chem. Sep. 1, 2009; 7130-7131.
Giaever et al., Micromotion of mammalian cells measured electrically. Proc Natl Acad Sci U S A. Sep. 1, 1991;88(17):7896-900.
Gorris et al., Analytical chemistry on the femtoliter scale. Angew Chem Int Ed. 2010; 49:2-18.
Gorris et al., Mechanistic aspects of horseradish peroxidase elucidated through single-molecule studies. *J Am Chem Soc*. May 6, 2009; 131(17):6277-82.
Gorris et al., Optical-fiber bundles. FEBS J. Nov. 2007; 274(21):5462-70. Epub Oct. 12, 2007.
Gorris et al., Stochastic inhibitor release and binding from single-enzyme molecules. *Proc Natl Acad Sci U S A*. Nov. 6, 2007; 104(45):17680-5. Epub Oct. 26, 2007.
Härma et al., Europium nanoparticles and time-resolved fluorescence for ultrasensitive detection of prostate-specific antigen. *Clin Chem*. Mar. 2001; 47(3):561-8.
Härma et al., Miniature single-particle immunoassay for prostate-specific antigen in serum using recombinant Fab fragments. *Clin Chem*. Nov. 2000; 46(11):1755-61.
Härma et al., Zeptomole detection sensitivity of prostate-specific antigen in a rapid microtitre plate assay using time-resolved fluorescence. *Luminescence*. Nov.-Dec. 2000;15(6):351-5.
Hashida et al., Immune complex transfer enzyme immunoassay that is more sensitive and specific than western blotting for detection of antibody immunoglobulin G to human immunodeficiency virus type 1 in serum with recombinant pol and gag proteins as antigens. *Clin Diagn Lab Immunol*. Sep. 1995; 2(5):535-41.

Haugland, Handbook: A Guide to Fluorescent Probes and Labeling Technologies. Invitrogen, Eugene, OR. Molecular Probes, US. pp. 473-538.
He et al., Selective encapsulation of single cells and subcellular organelles into picoliter- and femtoliter-volume droplets. *Anal Chem*. Mar. 15, 2005; 77(6):1539-44.
Healey et al., Fiberoptic DNA sensor array capable of detecting point mutations. *Anal Biochem*. Sep. 5, 1997; 251(2):270-9.
Healey et al., Multianalyte biosensors on optical imaging bundles. *Biosens Bioelectron*. 1997; 12(6):521-9.
Healey et al., Photodeposition of micrometer-scale polymer patterns on optical imaging fibers. *Science*. Aug. 25, 1995; 269(5227):1078-80.
Hindson et al., High-throughput droplet digital PCR system for absolute quantitation of DNA copy number. *Anal Chem*. Nov. 15, 2011;83(22):8604-10. Epub Oct. 28, 2011.
Hirano et al., A novel method for DNA molecular counting. Nucleic Acids Symp Ser. 2000;(44):157-8.
Hirschfeld, Remote and in-situ analysis. Anal Chem. 1986; 324:618-624.
Hunsaker et al., Nucleic acid hybridization assays employing dA-tailed capture probes. II. Advanced multiple capture methods. *Anal Biochem*. Sep. 1989; 181(2):360-70.
Johnson et al., Identification of multiple analytes using an optical sensor array and pattern recognition neural networks. Analytical Chemistry. 1997; 69(22):4641-8.
Kiss et al., High-throughput quantitative polymerase chain reaction in picoliter droplets. Anal Chem. Dec. 1, 2008;80(23):8975-81.
Kremsky et al., Immobilization of DNA via oligonucleotides containing an aldehyde or carboxylic acid group at the 5' terminus. *Nucleic Acids Res*. Apr. 10, 1987; 15(7):2891-909.
Kuang et al., Living bacterial cell array for genotoxin monitoring. *Anal Chem*. May 15, 2004; 76(10):2902-9.
Kuang et al., Monitoring "promiscuous" drug effects on single cells of multiple cell types. *Anal Biochem*. Oct. 15, 2005; 345(2):320-5.
Kuang et al., Simultaneously monitoring gene expression kinetics and genetic noise in single cells by optical well arrays. *Anal Chem*. Nov. 1, 2004; 76(21):6282-6.
Lafratta et al., Very high density sensing arrays. Chem Rev. Feb. 2008; 108(2):614-37. Epub Jan. 30, 2008.
Lee et al., A fiber-optic microarray biosensor using aptamers as receptors. *Anal Biochem*. Jun. 15, 2000; 282(1):142-6.
Li et al., Detection of single-molecule DNA hybridization using enzymatic amplification in an array of femtoliter-sized reaction vessels. J Am Chem Soc. Sep. 24, 2008; 130(38):12622-3. Epub Sep. 3, 2008.
Li et al., Molecule by molecule direct and quantitative counting of antibody-protein complexes in solution. *Anal Chem*. Aug. 1, 2004; 76(15):4446-51.
Lu et al., Single-molecule enzymatic dynamics. *Science*. Dec. 4, 1998; 282(5395):1877-82.
Luo et al., Single-molecule and ensemble fluorescence assays for a functionally important conformational change in T7 DNA polymerase. *Proc Natl Acad Sci U S A*. Jul. 31, 2007; 104(31):12610-5. Epub Jul. 18, 2007.
Melin et al., Microfluidic large-scale integration: the evolution of design rules for biological automation. *Annu Rev Biophys Biomol Struct*. 2007; 36:213-31.
Michael et al., Combined imaging and chemical sensing of fertilization-induced acid release from single sea urchin eggs. *Anal Biochem*. Sep. 10, 1999; 273(2):168-78.
Michael et al., Randomly ordered addressable high-density optical sensor arrays. *Anal Chem*. Apr. 1, 1998; 70(7):1242-8.
Monk et al., Fabrication of gold microtubes and microwires in high aspect ratio capillary arrays. *J Am Chem Soc*. Sep. 22, 2004; 126(37):11416-7.
Monk et al., Optical fiber-based biosensors. *Anal Bioanal Chem*. Aug. 2004; 379(7-8):931-45. Epub Jun. 23, 2004.
Monk et al., Progress toward the dermination of $Sr^{2+}$ in highly basic solutions using imagining optical fiber sensor arrays. J. Mater. Chem. 2005; 15:4361-4366.
Morrison et al., Nanoliter high throughput quantitative PCR. Nucleic Acids Res. 2006;34(18):e123. Epub Sep. 25, 2006.

(56) References Cited

OTHER PUBLICATIONS

Munkholm et al., Polymer modification of fiber optic chemical sensors as a method of enhancing fluroescence signal for pH measurement. Anal Chem. 1986; 58:1427-1430.
Nagai et al., High-throughput PCR in silicon based microchamber array. *Biosens Bioelectron.* Dec. 2001; 16(9-12):1015-9.
Nalefski et al., Single-molecule detection for femtomolar quantification of proteins in heterogeneous immunoassays. *Clin Chem.* Nov. 2006; 52(11):2172-5.
Nam et al., Nanoparticle-based bio-bar codes for the ultrasensitive detection of proteins. *Science.* Sep. 26, 2003;301(5641):1884-6.
Niemeyer et al., Combination of DNA-directed immobilization and immuno-PCR: very sensitive antigen detection by means of self-assembled DNA-protein conjugates. *Nucleic Acids Res.* Aug. 15, 2003; 31(16):e90, 7 pages.
Panova et al., In situ fluorescence imaging of localized corrosion with a pH-sensitive imaging fiber. *Anal Chem.* Apr. 15, 1997; 69(8):1635-41.
Pantano et al., Analytical applications of optical imaging fibers. *Anal Chem.* Aug. 1, 1995; 67(15):481A-487A.
Pantano et al., Ordered nanowell arrays. Chemistry of Materials. 1996;8: 2832-2835.
Pantano et al., Toward a near-field optical array. Rev. Sci. Instrum. 1997; 68(3) 1357-1359.
Peterson et al., Fiber optic pH probe for physiological use. *Anal Chem.* May 1980; 52(6):864-9.
Qiu et al., Fluorescence single-molecule counting assays for high-sensitivity detection of cytokines and chemokines. *Clin Chem.* Nov. 2007; 53(11):2010-2.
Randle et al., Integrating molecular detection and response to create self-signalling antibodies. *Biochem Biophys Res Commun.* Nov. 12, 2004; 324(2):504-10.
Rissin et al., Attomolar detection of proteins in serum using single molecule enzyme-linked immunosorbent assays. Quanterix Corporation. Oak Ridge Conference, San Jose, CA. Poster. 2010. 1 page.
Rissin et al., Digital concentration readout of single enzyme molecules using femtoliter arrays and Poisson statistics. *Nano Lett.* Mar. 2006; 6(3):520-3.
Rissin et al., Digital readout of target binding with attomole detection limits via enzyme amplification in femtoliter arrays. *J Am Chem Soc.* May 17, 2006; 128(19):6286-7.
Rissin et al., Distinct and long-lived activity states of single enzyme molecules. J Am Chem Soc. Apr. 16, 2008; 130(15):5349-53. Epub Mar. 5, 2008.
Rissin et al., Duplexed sandwich immunoassays on a fiber-optic microarray. *Anal Chim Acta.* Mar. 30, 2006; 564(1):34-9. Epub Nov. 11, 2005.
Rissin et al., Single-molecule enzyme-linked immunosorbent assay detects serum proteins at subfemtomolar concentrations. *Nat Biotechnol.* Jun. 2010; 28(6):595-9 and supplemental pages. Epub May 23, 2010.
Roeffaers et al., Single-molecule fluorescence spectroscopy in (bio)catalysis. *Proc Natl Acad Sci U S A.* Jul. 31, 2007; 104(31):12603-9. Epub Jul. 30, 2007.
Rondelez et al., Highly coupled ATP synthesis by F1-ATPase single molecules. *Nature.* Feb. 17, 2005; 433(7027):773-7
Rondelez et al., Microfabricated arrays of femtoliter chambers allow single molecule enzymology. *Nat Biotechnol.* Mar. 2005; 23(3):361-5. Epub Feb. 20, 2005.
Rotman, Measurement of activity of single molecules of beta-D-galactosidase. *Proc Natl Acad Sci U S A.* Dec. 15, 1961; 47:1981-91.
Schauer et al., A cross-reactive, class-selective enzymatic array assay. *J Am Chem Soc.* Sep. 26, 2001; 123(38):9443-4.
Schmidinger, et al., Inhibitor and protein microarrays for activity-based recognition of lipolytic enzymes. *Chembiochem.* Mar. 2006; 7(3):527-34.
Schweitzer et al., Inaugural article: immunoassays with rolling circle DNA amplification: a versatile platform for ultrasensitive antigen detection. *Proc Natl Acad Sci U S A.* Aug. 29, 2000; 97(18):10113-9.

Seydack, Nanoparticle labels in immunosensing using optical detection methods. *Biosens Bioelectron.* Jun. 15, 2005; 20(12):2454-69. Epub Dec. 16, 2004.
Shen et al. High-throughput SNP genotyping on universal bead arrays. Mutat Res. Jun. 3, 2005;573(1-2):70-82.
Shephard et al., Array-based binary analysis for bacterial typing. *Anal Chem.* Jan. 1, 2005; 77(1):319-26.
Song et al., Detecting biological warfare agents. *Emerg Infect Dis.* Oct. 2005; 11(10):1629-32.
Song et al., Fiber-optic microsphere-based arrays for multiplexed biological warfare agent detection. Anal Chem. Feb. 15, 2006; 78(4):1023-33.
Soukka et al., Supersensitive time-resolved immunofluorometric assay of free prostate-specific antigen with nanoparticle label technology. Clin Chem. 2001; 47(7):1269-78.
Stamou et al., Self-assembled microarrays of attoliter molecular vessels. *Angew Chem Int Ed Engl.* Nov. 24, 2003; 42(45):5580-3.
Steemers et al., Multi-analyte sensing: from site-selective deposition to randomly ordered addressable optical sensors. Microchimica Acta. 1999; 131:99-105.
Steemers et al., Screening unlabeled DNA targets with randomly ordered fiber-optic gene arrays. *Nat Biotechnol.* Jan. 2000; 18(1):91-4.
Stitzel et al., Array-to-array transfer of an artificial nose classifier. *Anal Chem.* Nov. 1, 2000; 73(21):5266-71. Epub Sep. 28, 2001.
Subbaraman, Detecting single cancer molecules. Technol Rev. Jun. 3, 2010. Last accessed at http://www.technologyreview.com/biomedicine/25462/ on Jan. 31, 2012. 1 page.
Sykes et al., Quantitation of targets for PCR by use of limiting dilution. Biotechniques. 1992;13(3):444-9.
Szunerits et al., "Aluminum Surface Corrosion and the Mechanism of Inhibitors Using pH and Metal Ion Selective Imaging Fiber Bundles," *Analytical Chemistry*, 2002, 74(4), 886-894.
Szunerits et al., "Fabrication of an Optoelectrochemical Microring Array," *Analytical Chemistry*, 2002, 74(7), 1718-1723.
Szunerits et al., Spatially resolved electrochemiluminescence on an array of electrode tips. *Anal Chem.* Sep. 1, 2003; 75(17):4382-8.
Szunerits et al., The use of optical fiber bundles combined with electrochemistry for chemical imaging. *Chemphyschem.* Feb. 17, 2003; 4(2):186-92. Epub Feb. 7, 2003.
Szurdoki et al., A duplexed microsphere-based fluorescent immunoassay. *Anal Biochem.* Apr. 15, 2001; 291(2):219-28.
Tam et al., An imaging fiber-based optical tweezer array for microparticle array assembly. Applied Physics Letters. 2004; 84(21):4289-4291.
Tam et al., Fabrication and optical characterization of imaging fiber-based nanoarrays. Talanta. Sep. 15, 2005; 67(3):498-502. Epub Jul. 27, 2005.
Tam et al., Parallel microparticle manipulation using an imaging fiber bundle-based optical tweezer array and a digital micromirror device. Applied Physics Letters. 2006; 89:194101/1-194101/3.
Tan et al., Monitoring the reactions of single enzyme molecules and single metal ions. *Anal Chem.* 1997; 69:4242-4248.
Taylor et al., Application of high-density optical microwell arrays in a live-cell biosensing system. *Anal Biochem.* Feb. 15, 2000; 278(2):132-42.
Tessler et al., Protein quantification in complex mixtures by solid phase single-molecule counting. *Anal Chem.* Sep. 1, 2009; 81(17):7141-8.
Thaxton et al., Nanoparticle-based bio-barcode assay redefines "undetectable" PSA and biochemical recurrence after radical prostatectomy. Proc Natl Acad Sci U S A. Nov. 3, 2009;106(44):18437-42. Epub Oct. 19, 2009.
Timmerman, Quanterix CEO sets sight on early detection of cancer, neurological diseases in the blood. Xconomy. Jan. 19, 2010. Last accessed at http://www.xconomy.com/boston/2010/01/19/quanterix-ceo-sets-sight-on-early-detection-of-cancer-neurological-diseases-in-the-blood/ on Jan. 31, 2012. 4 pages.
Todd et al., Ultrasensitive flow-based immunoassays using single-molecule counting. *Clin Chem.* Nov. 2007; 53(11):1990-5. Epub Sep. 21, 2007.

(56) References Cited

OTHER PUBLICATIONS

Tromberg et al., Development of antibody-based fiber-optic sensors for detection of a benzo[a]pyrene metabolite. *Anal Chem.* Sep. 15, 1988; 60(18):1901-8.

Ueberfeld et al., Reversible ratiometric probe for quantitative DNA measurements. *Anal Chem.* Feb. 15, 2004; 76(4):947-52. Epub Jan. 20, 2004.

Vo-Dinh et al., Phase-resolved fiber-optics fluoroimmunosensor. Applied Spectroscopy. 1990; 44(1):128-132.

Vogelstein et al., Digital PCR. Proc Natl Acad Sci U S A. Aug. 3, 1999;96(16):9236-41.

Walt et al., Biosensing with live cells using a high-density optical fiber array. Radiation Research. 2001; 156(4):442.

Walt et al., Microsensor arrays for saliva diagnostics. Ann N Y Acad Sci. Mar. 2007; 1098:389-400.

Walt et al., Optical sensor arrays for odor recognition. *Biosens Bioelectron.* Sep. 15, 1998; 13(6):697-9.

Walt et al., Ultrasensitive detection of proteins using single molecule arrays (SiMoA). Presented Mar. 1, 2010. Pittcon. Abstract and PowerPoint presentation. 32 pages.

Walt, An array of solutions, fiber arrays contribute to studies of individual cellular behavior and response. SPIE's oemagazine. 2005; 19-21.

Walt, Fiber optic array biosensors. Biotechniques. Nov. 2006; 41(5):529, 531, 533, 535 passim.

Walt, Fiber optic imaging sensors. Accounts of Chemical Research. 1998; 31:267-278.

Walt, Imaging optical sensor arrays. *Curr Opin Chem Biol.* Oct. 2002; 6(5):689-95.

Walt, Techview: molecular biology. Bead-based fiber-optic arrays. *Science.* Jan. 21, 2000;287(5452):451-2.

Wang et al., Quantification of protein based on single-molecule counting by total internal reflection fluorescence microscopy with adsorption equilibrium. *Anal Chim Acta.* May 2, 2007; 590(1):104-9. Epub Mar. 15, 2007.

Warren et al., Transcription factor profiling in individual hematopoietic progenitors by digital RT-PCR. Proc Natl Acad Sci U S A. Nov. 21, 2006;103(47):17807-12. Epub Nov. 10, 2006.

Whitaker et al., Fiber-based single cell analysis of reporter gene expression in yeast two-hybrid systems. *Anal Biochem.* Jan. 1, 2007; 360(1):63-74. Epub Oct. 30, 2006.

Whitaker et al., Multianalyte single-cell analysis with multiple cell lines using a fiber-optic array. *Anal Chem.* Dec. 1, 2007; 79(23):9045-53. Epub Nov. 1, 2007.

White et al., An olfactory neuronal network for vapor recognition in an artificial nose. *Biol Cybern.* Apr. 1998; 78(4):245-51.

White et al., Rapid analyte recognition in a device based on optical sensors and the olfactory system. Analytical Chemistry. 1996; 68(13):2191-2202.

Wu et al., Development and preliminary clinical validation of a high sensitivity assay for cardiac troponin using a capillary flow (single molecule) fluorescence detector. *Clin Chem.* Nov. 2006; 52(11):2157-9.

Xie et al., Optical studies of single molecules at room temperature. *Annu Rev Phys Chem.* 1998; 49:441-80.

Xie et al., Single gold nanoparticles counter: an ultrasensitive detection platform for one-step homogeneous immunoassays and DNA hybridization assays. J Am Chem Soc. Sep. 9, 2009;131(35):12763-70.

Xue et al., Differences in the chemical reactivity of individual molecules of an enzyme. *Nature.* Feb. 23, 1995; 373(6516):681-3.

Young et al., Integrating high-content screening and ligand-target prediction to identify mechanism of action. Nat Chem Biol. Jan. 2008; 4(1):59-68. Epub Dec. 9, 2007.

[No Author Listed], bioMérieux and Quanterix Sign Strategic Partnership in Ultrasensitive and Multiplex Immunoassays. Quanterix Press Release. Nov. 15, 2012. 2 pages.

[No Author Listed], Does Brain Hypoxia Help Kick Off Alzheimer's Pathology? Alzheimer Research Forum. Dec. 16, 2011. http://www.alzforum.org/new/detailprint.asp?id=3002 [last accessed Jan. 30, 2012]. 4 pages.

[No Author Listed], Pittcon Announces 2010 Technical Program: Webcast of Selected Symposia. Press Release. Oct. 15, 2009. http://archive.constantcontact.com/fs033/1102032821298/archive/1102745632000.html [last accessed Jan. 31, 2012]. 2 pages.

[No Author Listed], Quanterix and STRATEC Announce Strategic Partnership. Quanterix Press Release. Aug. 16, 2011. 2 pages.

[No Author Listed], Quanterix Announces Commercial Availability of its Simoa Single Molecule Array Technology. Quanterix Press Release. Jul. 30, 2013. 2 pages.

[No Author Listed], Quanterix Digital ELISA Measures Low Abundance Biomarkers of Inflammation in Crohn's Disease. Quanterix Press Release. Aug. 19, 2011. Last accessed at http://www.quanterix.com/events-news/press-releases/item/142-quanterix-digital-elisa-measures-low-abundance-biomarkers-of-inflammation-in-crohn's-disease on Sep. 20, 2012.

[No Author Listed], Quanterix Launches Multiplexed Single Molecule Immunoassay Technology to Improve Diagnosis and Potential Treatment of Complex Diseases. Quanterix Press Release. Sep. 17, 2013. 2 pages.

[No Author Listed], Quanterix to Present Poster Session on Blood-based Brain Biomarker Measurements of Sports Related Brain Injury at Neuroscience. Quanterix Press Release. Nov. 4, 2013. 1 page.

[No Author Listed], Quanterix's Simoa technology to detect blood biomarker for concussion in hockey players. Quanterix Press Release. Mar. 14, 2014. 1 page.

[No Author Listed], Quanterix's Ultrasensitive Simoa™ Technology Demonstrates Equivalence with NAT and 3,000x Improvement in Sensitivity over Conventional Immunoassays for HIV Detection. Quanterix Press Release. Oct. 11, 2012. 1 page.

[No Author Listed], Quanterix's Ultrasensitive Simoa™ Technology Forges New Ground with Direct Detection of Genomic DNA in Human Blood and River Water. Quanterix Press Release. Jan. 22, 2013. 2 pages.

Duffy et al., Detection of prostate specific antigen (PSA) in the serum of radical prostatectomy patients at femtogram per milliliter levels using digital ELISA (AccuPSA™) based on single molecule arrays (SiMoA). AACC Meeting Poster. 2010. 1 page.

Duffy, Immunoassays with Broad Dynamic Ranges based on Combining Digital and Digitally Enhanced Analog Detecion of Enzyme Labels. Oak Ridge Conference. Presentation. Apr. 15, 2011. 16 pages.

Okrongly, Single Molecule Enzyme Detection and Application to Immunoassay: Implications for Personalized Medicine. Abstract and Presentation. ISE International Conference. May 4, 2010. 24 pages.

Prabhakar et al., Simultaneous quantification of proinflammatory cytokines in human plasma using the LabMAP assay. J Immunol Methods. Feb. 1, 2002;260(1-2):207-18.

Rissin et al., Immunoassays with broad dynamic ranges based on combining digital and digitally-enhanced analog detection of enzyme labels. Oak Ridge Conference. Poster 7 and Abstract. Apr. 14-15, 2011. 2 pages.

Rissin et al., Simultaneous detection of single molecules and singulated ensembles of molecules enables immunoassays with broad dynamic range. Anal Chem. Mar. 15, 2011;83(6):2279-85. Epub Feb. 23, 2011.

Song et al., Single molecule measurements of tumor necrosis factor α and interleukin-6 in the plasma of patients with Crohn's disease. J Immunol Methods Sep. 30, 2011;372(1-2):177-86. Epub Jul. 27, 2011.

Wilson et al., Development of AccuPSA™, a novel digital immunoassay for sub-femtomolar measurement of PSA in post radical prostatectomy patients. AACR Molecular diagnostics in Cancer Therapeutic Development Abstract and Poster. 2011. 1 page.

Wilson, Serum Measurement of Hypoxia-Induced Amyloid Beta 1-42 Following Resuscitation from Cardiac Arrest. Abstract and Poster. American Academy of Neurology Annual Meeting. Apr. 9, 2011. 2 pages.

\* cited by examiner

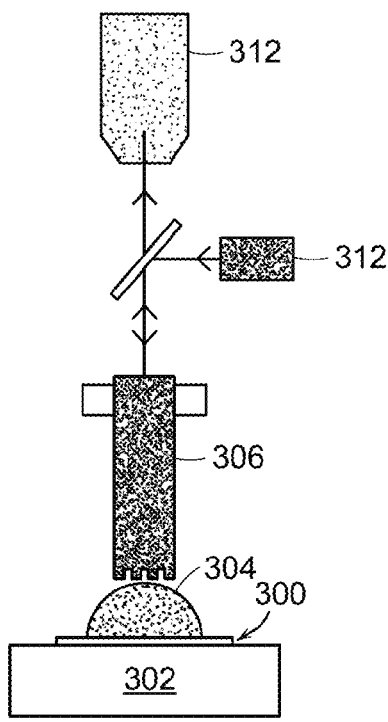
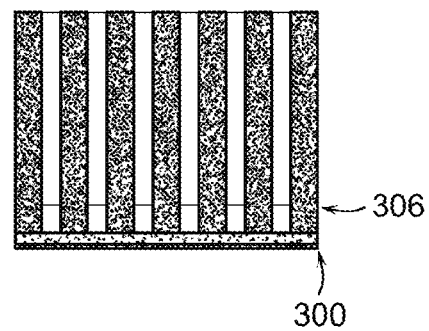
FIG. 12A    FIG. 12B
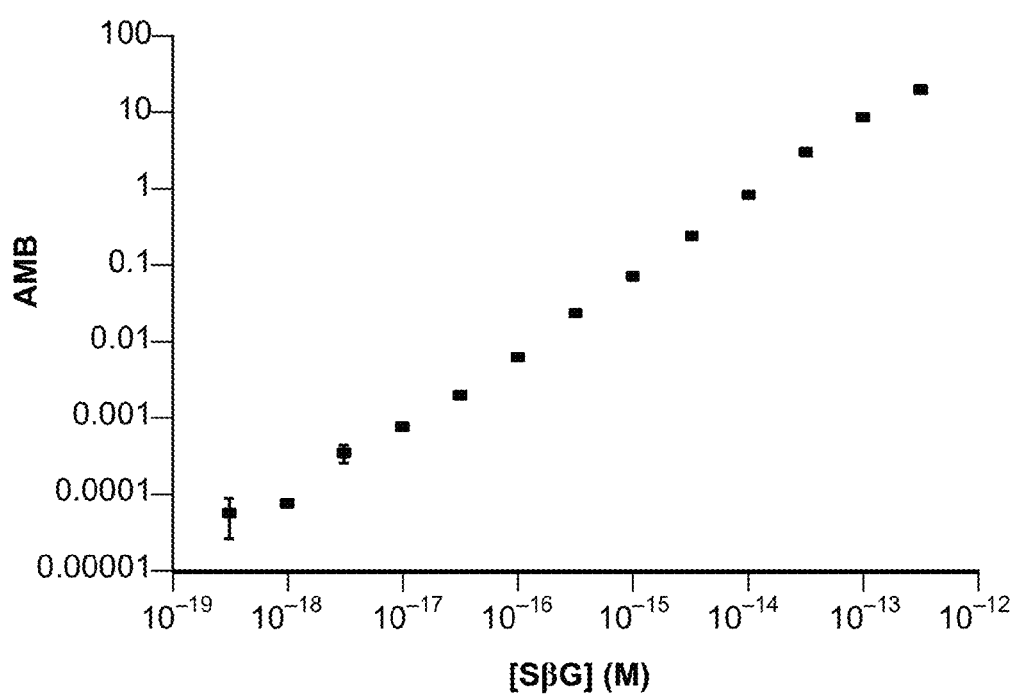
FIG. 13A

| [SβG] (M) | $f_{on}$ (% active) | AMB $AMB_{digital}$ or $AMB_{analog}$ | %CV AMB |
|---|---|---|---|
| 0 | 0 | 0 | 0% |
| $3.16 \times 10^{-19}$ | 0.006 | $5.5 \times 10^{-5}$ | 54% |
| $1.00 \times 10^{-18}$ | 0.007 | $7.3 \times 10^{-5}$ | ND |
| $3.16 \times 10^{-18}$ | 0.03 | $3.4 \times 10^{-4}$ | 25% |
| $1.00 \times 10^{-17}$ | 0.08 | $7.7 \times 10^{-4}$ | 11% |
| $3.16 \times 10^{-17}$ | 0.20 | $2.0 \times 10^{-3}$ | 16% |
| $1.00 \times 10^{-16}$ | 0.62 | $6.2 \times 10^{-3}$ | 7% |
| $3.16 \times 10^{-16}$ | 2.36 | $2.39 \times 10^{-2}$ | 5% |
| $1.00 \times 10^{-15}$ | 6.99 | $7.25 \times 10^{-2}$ | 5% |
| $3.16 \times 10^{-15}$ | 21.89 | 0.2470 | <1% |
| $1.00 \times 10^{-14}$ | 56.16 | 0.8286 | 11% |
| $3.16 \times 10^{-14}$ | 96.27 | 2.902 | 4% |
| $1.00 \times 10^{-13}$ | 99.06 | 8.264 | 12% |
| $3.16 \times 10^{-13}$ | 99.12 | 19.55 | 14% |

FIG. 13B

| [SβG] (fM) | $f_{on}$ (% active beads) | $\mu = AMB_{digital}$ |
|---|---|---|
| 0.6 | 5.07 | 0.0521 |
| 0.8 | 7.10 | 0.0736 |
| 1 | 8.89 | 0.0931 |
| 2 | 16.29 | 0.1778 |
| 4 | 31.33 | 0.3759 |
| 6 | 43.84 | 0.5769 |
| 8 | 53.42 | 0.7639 |

METHODS AND SYSTEMS FOR EXTENDING DYNAMIC RANGE IN ASSAYS FOR THE DETECTION OF MOLECULES OR PARTICLES

RELATED APPLICATIONS

This application claims the benefit of U.S. Provisional Patent Application Ser. No. 61/441,894, filed Feb. 11, 2011, entitled "Methods and Systems for Extending Dynamic Range in Assays for the Detection of Molecules or Particles," by Rissin et al. This application is also a continuation-in-part of U.S. patent application Ser. No. 12/731,136, filed Mar. 24, 2010, and issued as U.S. Pat. No. 8,415,171, entitled "Methods and Systems for Extending Dynamic Range in Assays for the Detection of Molecules or Particles," by Rissin et al., which claims the benefit of U.S. Provisional Patent Application Ser. No. 61/309,165, filed Mar. 1, 2010, entitled "Methods and Systems for Extending Dynamic Range in Assays for the Detection of Molecules or Particles," by Rissin et al. Each of the above-indicated applications is incorporated herein by reference.

FIELD OF THE INVENTION

Described herein are systems and methods for extending the dynamic range of analytical assays and systems used for determining a concentration of analyte molecules or particles in a fluid sample.

BACKGROUND OF THE INVENTION

Methods and systems that are able to quickly and accurately detect and, in certain cases, quantify a target analyte molecule in a sample are the cornerstones of modern analytical measurements. Such systems and methods are employed in many areas such as academic and industrial research, environmental assessment, food safety, medical diagnosis, and detection of chemical, biological, and radiological warfare agents. Advantageous features of such techniques may include specificity, speed, and sensitivity.

Many of the known methods and techniques are limited by the dynamic range of the concentrations the methods and techniques can detect accurately (e.g., limited dynamic range) and/or do not have the sensitivity to detect molecules or particles when they are present at very low concentration.

Accordingly, improved systems and methods for extending the dynamic range of analytical assays and systems used for determining a measure of the concentration of molecules or particles in a fluid sample are needed.

SUMMARY OF THE INVENTION

Described herein are systems and methods for extending the dynamic range of analytical methods and systems used for determining the concentration of analyte molecules or particles in a fluid sample. The subject matter of the present invention involves, in some cases, interrelated products, alternative solutions to a particular problem, and/or a plurality of different uses of one or more systems and/or articles.

In some embodiments, a system for determining a measure of the concentration of analyte molecules or particles in a fluid sample, comprising an assay substrate comprising a plurality of locations each comprising a binding surface forming or contained within such locations, wherein at least one binding surface comprises at least one analyte molecule or particle immobilized on the binding surface, at least one detector configured to address a plurality of the locations, able to produce at least one signal indicative of the presence or absence of an analyte molecule or particle at each location addressed and having an intensity varying with the number of analyte molecules or particles at each location, and at least one signal processor configured to determine from the at least one signal the percentage of said locations containing at least one analyte molecule or particle, and further configured to, based upon the percentage, either determine a measure of the concentration of analyte molecules or particles in the fluid sample based at least in part on the number of locations containing at least one analyte molecule or particle, or determine a measure of the concentration of analyte molecules or particles in the fluid sample based at least in part on an intensity level of the at least one signal indicative of the presence of a plurality of analyte molecules or particles.

In some embodiments, a method for determining a measure of the concentration of analyte molecules or particles in a fluid sample comprises providing analyte molecules or particles immobilized with respect to a binding surface having affinity for at least one type of analyte molecule or particle, the binding surface forming or contained within one of a plurality of locations on a substrate, addressing at least some of the plurality of locations and determining a measure indicative of the percentage of said locations containing at least one analyte molecule or particle, and based upon the percentage, either determining a measure of the concentration of analyte molecules or particles in the fluid sample based at least in part on the number of locations containing at least one analyte molecule or particle or determining a measure of the concentration of analyte molecules or particles in the fluid sample based at least in part on a measured intensity of a signal that is indicative of the presence of a plurality of analyte molecules or particles.

In some embodiments, a method for determining a measure of the concentration of analyte molecules or particles in a fluid sample comprises exposing a plurality of capture objects, each including a binding surface having affinity for at least one type of analyte molecule or particle, to a solution containing or suspected of containing the at least one type of analyte molecules or particles, wherein at least some of the capture objects become associated with at least one analyte molecule or particle, spatially segregating at least a portion of the capture objects subjected to the exposing step into a plurality of locations, addressing at least some of the plurality of locations and determining a measure indicative of the percentage said locations containing a capture object associated with at least one analyte molecule or particle, wherein the locations addressed are locations which contain at least one capture object, and based upon the percentage, either determining a measure of the concentration of analyte molecules or particles in the fluid sample based at least in part on the number of locations containing a capture object associated with at least one analyte molecule or particle, or determining a measure of the concentration of analyte molecules or particles in the fluid sample based at least in part on a measured intensity level of a signal of that is indicative of the presence of a plurality of analyte molecules or particles.

BRIEF DESCRIPTION OF THE DRAWINGS

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents mentioned in the text are incorporated by reference in their entirety. In case of conflict between the description contained in the present specification and a document incorporated by reference, the present specification, including definitions, will control.

FIG. 12A depicts an experimental set-up for detection using light;

FIG. 12B shows a fiber optic array that has been sealed with a sealing component;

FIG. 13A shows a plot of AMB as a function of enzyme concentration, according to one embodiment;

FIG. 13B shows a table including the % active beads and AMB values as a function of enzyme concentration, according to one embodiment;

DETAILED DESCRIPTION

Figure 1:
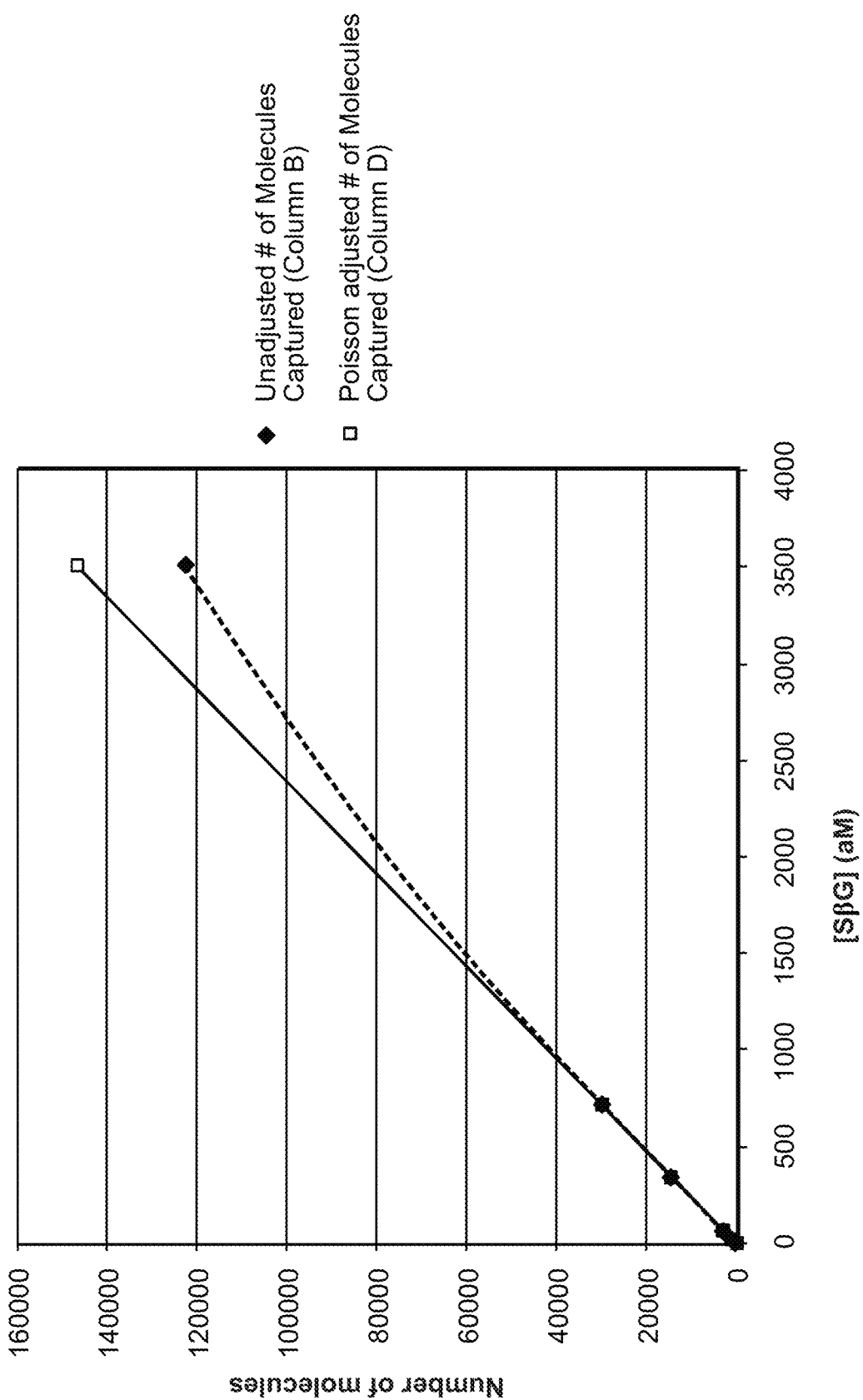
FIG. 1 shows a graphical representation of results of a Poisson distribution adjustment, as performed according to some embodiments.

Described herein are systems and methods for extending the dynamic range of analytical assay methods and systems used for determining a concentration of analyte molecules or particles (such as, for example, cells, cell organelles and other biological or non-biological particulates) in a fluid sample. The subject matter of the present invention involves, in some cases, interrelated products, alternative solutions to a particular problem, and/or a plurality of different uses of one or more systems and/or articles. It should be understood, that while much of the discussion below is directed to analyte molecules, this is by way of example only, and other materials may be detected and/or quantified, for example, analytes in particulate form. Some exemplary examples of analyte molecules and particles are described herein.

The methods and system described herein may be useful to extend the dynamic range of analytical methods and systems used in certain embodiments by employing two or more techniques for determining a measure of the concentration of analyte molecules in a fluid sample. In some embodiments, the dynamic range may be extended by combining both an analog, intensity-based detection/analysis method/system and a digital detection/analysis method/system, as described herein. In some cases, when the analyte molecules in the fluid sample are present at lower concentration ranges, single analyte molecules may be detected and the number of analyte molecules may be determined. A measure of the concentration of analyte molecules in a fluid sample may be based at least in part on this data (e.g., the number of analyte molecule) using a digital analysis method/system. In some cases, the data may be further manipulated using a Poisson distribution adjustment. At higher concentration ranges (e.g., at concentration levels where isolating/detecting/determining single analyte molecules may become less practical) a measure of the concentration of analyte molecules in the fluid sample may be determined using and analog, intensity level-based technique. In an analog analysis method/system, the measure of the concentration may be based at least in part on a measured relative signal intensity, wherein the total measured intensity may be correlated with the presence and quantity of analyte molecules. In certain embodiments, both analog and digital capability may be combined in a single assay/system, such that, for example, a calibration standard may be developed for an analyte molecule of interest across a wide dynamic range. In one such example, a single calibration curve may be generated using both a digital and analog quantification technique, wherein the digital and analog regimes of the calibration are linked by using a calibration factor, as described herein. The determination of an unknown concentration of an analyte molecule in a test fluid sample may be based at least in part by comparing test results (e.g., number/fraction of locations containing an analyte molecule (digital) and/or measured intensity level (analog)) with the calibration curve.

The term, "dynamic range" is given its ordinary meaning in the art and refers to the range of the concentration of analyte molecules in a fluid sample that may be quantitated by a system or method without dilution or concentration of the sample or change in the assay conditions producing a similar result (e.g., concentration of reagents employed, etc.), and wherein the measured concentration of the analyte molecules may be substantially accurately determined. The concentration of analyte molecules in a fluid sample may be considered to be substantially accurately determined if the measured concentration of the analyte molecules in the fluid sample is within about 10% of the actual (e.g., true) concentration of the analyte molecules in the fluid sample. In certain embodiments, the measured concentration of the analyte molecules in the fluid sample is substantially accurately determined in embodiments where the measured concentration is within about 5%, within about 4%, within about 3%, within about 2%, within about 1%, within about 0.5%, within about 0.4%, within about 0.3%, within about 0.2%, or within about 0.1% of the actual concentration of the analyte molecules in the fluid sample. In some cases, the measure of the concentration determined differs from the true (e.g., actual) concentration by no greater than about 20%, no greater than about 15%, no greater than about 10%, no greater than about 5%, no greater than about 4%, no greater than about 3%, no greater than about 2%, no greater than about 1%, or no greater than about 0.5%. The accuracy of the assay method may be determined, in some embodiments, by determining the concentration of analyte molecules in a fluid sample of a known concentration using the selected assay method and comparing the measured concentration with the actual concentration.

In some embodiments, the inventive systems or methods may be capable of measuring concentrations of analyte molecules in a fluid sample over a dynamic range of more than about 1000 (3 log), about 10,000 (4 log), about 100,000 (5 log), about 350,000 (5.5 log), 1,000,000 (6 log), about 3,500,000 (6.5 log), about 10,000,000 (7 log), about 35,000,000 (7.5 log), about 100,000,000 (8 log), or more.

In some embodiments, the concentration (e.g., unknown concentration) of analyte molecules in the fluid sample that may be substantially accurately determined is less than about 5000 fM (femtomolar), less than about 3000 fM, less than about 2000 fM, less than about 1000 fM, less than about 500 fM, less than about 300 fM, less than about 200 fM, less than about 100 fM, less than about 50 fM, less than about 25 fM, less than about 10 fM, less than about 5 fM, less than about 2 fM, less than about 1 fM, less than about 500 aM (attomolar), less than about 100 aM, less than about 10 aM, less than about 5 aM, less than about 1 aM, less than about 0.1 aM, less than about 500 zM (zeptomolar), less than about 100 zM, less than about 10 zM, less than about 5 zM, less than about 1 zM, less than about 0.1 zM, or less. In some cases, the limit of detection (e.g., the lowest concentration of an analyte molecule which may be determined in solution) is about 100 fM, about 50 fM, about 25 fM, about 10 fM, about 5 fM, about 2 fM, about 1 fM, about 500 aM (attomolar), about 100 aM, about 50 aM, about 10 aM, about 5 aM, about 1 aM, about 0.1 aM, about 500 zM (zeptomolar), about 100 zM, about 50 zM, about 10 zM, about 5 zM, about 1 zM, about 0.1 zM, or less. In some embodiments, the concentration of analyte molecules or particles in the fluid sample that may be substantially accurately determined is between about 5000 fM and about 0.1 fM, between about 3000 fM and about 0.1 fM, between about 1000 fM and about 0.1 fM, between about 1000 fM and about 0.1 zM, between about 100 fM and about 1 zM, between about 100 aM and about 0.1 zM, or less. The upper limit of detection (e.g., the upper concentration of an analyte molecule which may be determined in solution) is at least about 100 fM, at least about 1000 fM, at least about 10 pM (picomolar), at least about 100 pM, at least about 1000 pM, at least about 10 nM (nanomolar), at least about 100 nM, at least about 1000 nM, at least about 10 uM, at least about 100 uM, at least about 1000 uM, at least about 10 mM, at least about 100 mM, at least about 1000 mM, or greater. In some embodiments, the concentration of analyte molecules or particles in the fluid sample determined is less than about $50 \times 10^{-15}$ M, or less than about $40 \times 10^{-15}$ M, or less than about $30 \times 10^{-15}$ M, or less than about $20 \times 10^{-15}$ M, or less than about $10 \times 10^{-15}$ M, or less than about, or less than about $1 \times 10^{-15}$ M.

Exemplary Combined Digital/Analog Analysis Methods/Systems

The following section describes exemplary methods and systems for extending the dynamic range of analytical methods/systems used to determine a measure of concentration of analyte molecules or particles in a fluid sample. In some embodiments, the analytical method employed is capable of individually isolating and detecting single analyte molecules at low concentrations. In some cases, the analytical method involves spatially segregating a plurality of analyte molecules into a plurality of locations in or on a surface of a substrate (e.g., plate, chip, optical fiber face, etc.). At low concentration ranges, the analyte molecules may be spatially segregated such that a statistically significant fraction of such locations contain no analyte molecules with at least some of the locations containing at least one analyte molecule. Methods and systems which may be used in conjunction with the methods/systems of the present invention for extending the dynamic range are described herein.

As an exemplary method, and as described in more detail herein, a plurality of analyte molecules in a fluid sample may be made to become immobilized with respect to a plurality of capture objects (e.g., beads) that each include a binding surface having affinity for at least one type of analyte molecule (see, for example, methods and capture objects described in commonly owned U.S. patent application Ser. No. 12/731,130, entitled "Ultra-Sensitive Detection of Molecules or Particles using Beads or Other Capture Objects" by Duffy et al., filed Mar. 24, 2010; and International. Patent Application No. (not yet determined), entitled "Ultra-Sensitive Detection of Molecules or Particles using Beads or Other Capture Objects" by Duffy et al., filed Mar. 1, 2011 (Attorney Docket No. Q0052.70011WO00), each herein incorporated by reference). At least some of the beads (e.g., at least some associated with at least one analyte molecule) may be spatially separated/segregated into a plurality of locations (e.g., reaction vessels), and at least some of the reaction vessels may be addressed/interrogated to detect the presence of a bead and analyte molecule. In some cases, the plurality of reaction vessels addressed is a portion or essentially all of the total quantity of reaction vessels which may contain at least one capture object (e.g., either associated with at least one analyte molecule or not associated with any analyte molecules). It should be understood, that while much of the discussion herein focuses on methods comprising immobilizing analyte molecules with respect to beads (or other capture objects) prior to spatially segregating the plurality of analyte molecules into a plurality of reaction vessels, this is by no means limiting, and other methods/systems may be used for spatially segregating the analyte molecules, (e.g., where the analyte molecules are segregated into a plurality of locations without being immobilized on capture objects). Those of ordinary skill in the art will be able to apply the methods, systems, and analysis described herein to methods which do not employ capture objects (e.g., beads). For example, see U.S. Patent Application No. 20070259448, entitled "Methods and arrays for target analyte detection and determination of target analyte concentration in solution," by Walt et al., filed Feb. 16, 2007; U.S. Patent Application No. 20070259385, entitled "Methods and arrays for detecting cells and cellular components in small defined volumes," by Walt et al., filed Feb. 16, 2007; U.S. Patent Application No. 20070259381, entitled "Methods and arrays for target analyte detection and determination of reaction components that affect a reaction" by Walt et al., filed Feb. 16, 2007; International Patent Application No. PCT/US07/019184, entitled "Methods for Determining the Concentration of an Analyte in Solution" by Walt et al., filed Aug. 20, 2007; and International Patent Application No. PCT/US09/005428, entitled "Ultra-Sensitive Detection of Molecules or Enzymes" by Duffy et al., filed Sep. 9, 2009, herein incorporated by reference.

Following spatially segregating the beads into the reaction vessels, at least a portion of the reaction vessels may be addressed/interrogated to determine the number and/or percentage of the locations addressed which contain a bead associated with at least one analyte molecule. In some cases, the locations addressed are at least a portion of the locations which contain at least one bead (e.g., either associated with at least one analyte molecule or not associated with any analyte molecules). The percentage of locations which contain a bead associated with at least one analyte molecule (the percentage of "active" beads) is the number of beads associated with at least one analyte molecule divided by the total number of beads addressed, multiplied by 100%. Alternatively, if desired, the percentage of activity may be based on the number of locations addressed whether or not they contain a bead (i.e. active bead containing locations as a percentage of locations addressed). As will be understood by those of ordinary skill in the art, in embodiments where beads (or other capture objects) are not employed, the percentage "active beads" in the following discussion may be substituted for the percentage of locations containing at least one analyte molecule (e.g., the percentage "active locations").

In some embodiments, by determining the number/percentage of active beads the bulk analyte concentration in the fluid sample can be determined. Particularly at low concentration levels (e.g., in the digital concentration range), a measure of the concentration of analyte molecules in a fluid sample may be determined at least in part by counting beads as either "on" (e.g., a reaction vessel containing a bead associated with at least one analyte molecule) or "off" (e.g., a reaction vessel containing a bead not associated with any analyte molecule). At low ratios of analyte molecules to beads (e.g., less than about 1:5, less than about 1:10, less than about 1:20, or less), nearly all of the beads are associated with either zero or one analyte molecule. In this range, the percentage of active beads (e.g., "on" reaction vessels) may increase substantially linearly with increasing analyte concentration, and a digital analysis method may be advantageously used to analyze the data.

As the analyte concentration increases, however, a significant population of the beads generally associate with more than one analyte molecule. That is, at least some of the beads associate with two, three, etc. analyte molecules. Therefore, as the analyte concentration increases, at some point the percentage of active beads in a population generally will not be as linearly related to the bulk analyte concentration since a greater fraction of the beads may associate with more than one analyte molecule. In these concentration ranges, the data may still be advantageously analyzed using a digital analysis method (e.g., counting "on" and "off" beads), however it may be possible to improve the accuracy of the assay by applying a Poisson distribution adjustment to account for the binding probability of a population of analyte molecules to a population of beads. For example, according to Poisson distribution adjustment, in an assay that reports about 1.0% active beads (e.g., the ratio of beads associated with at least one analyte molecule to the total number of beads is about 1:100), about 99% of the beads are free of analyte molecules, about 0.995% of beads associate with one analyte molecule, and about 0.005% of beads associate with two analyte molecules. As a comparison, in an assay that reports about 20.0% active beads (e.g., the ratio of beads associated with at least one analyte molecule to the total number of beads is about 1:5), about 80% of the beads are free of analyte molecules, about 17.85% of beads associate with one analyte molecule, about 2.0% of beads associated with two analyte molecules and about 0.15% of beads associated with three analyte molecules. The non-linear effect (e.g., as seen in the second comparative example) can be accounted for across the entire concentration range in which there remains a statistically significant fraction (e.g., as described herein—see Equation 1 below and associated discussion) of beads not associated with any analyte molecules or particles in the sample (e.g., the range in which a digital analysis methods/system may be able to accurately determine a measure of the concentration, e.g., in some cases up to about 20% active beads, up to about 30% active beads, up to about 35% active beads, up to about 40% active beads, up to about 45% active beads, up to about 50% active beads, up to about 60% active bead, up to about 70% active beads, or more) using a Poisson distribution adjustment. A Poisson distribution describes the likelihood of a number of events occurring if the average number of events is known. If the expected number of occurrences is m, then the probability ($P_\mu(v)$) that there are exactly v occurrences (v being a non-negative integer, v=0, 1, 2, . . . ) may be determined by Equation 1:

$$P_\mu(v) = e^{-\mu}\left(\frac{\mu^v}{v!}\right) \quad \text{(Eq. 1)}$$

In some embodiments of the present invention, µ is equal to the ratio of number of analyte molecules detected to the total number of beads detected (e.g., either associated with or not associated with any analyte molecules), and v is the number of beads containing a certain number of analyte molecules (e.g., the number of beads associated with either 0, 1, 2, 3, etc. analyte molecules). By determining µ from an experiment, therefore, the number and, through further calculations, the concentration of analyte molecules can be determined. In the digital/binary mode of measurements where beads associated with 1, 2, 3, 4, etc. analyte molecules are indistinguishable (e.g., where v=1, 2, 3, 4 are indistinguishable) and the analyte molecule containing beads (or locations) are simply characterized as "on." Occurrences of v=0 can by determined definitively as the number of "off" beads (or locations). ($P_\mu(0)$) may be calculated according to Equation 2:

$$P_\mu(0) = e^{-\mu}\left(\frac{\mu^0}{0!}\right) = e^{-\mu} \quad \text{(Eq. 2)}$$

and the number of expected occurrences, µ, may be determined based on a rearrangement of Equation 2, as given in Equation 3:

$$\mu = -\ln[P_\mu(0)] \quad \text{(Eq. 3).}$$

The number of occurrences of beads associated with no analyte molecules, $P_\mu(0)$, is equal to 1 minus the total number of beads with all other occurrences (e.g., beads associated at least one analyte molecule) then μ is given by Equation 4:

$$\mu = \frac{\text{Number of analyte molecules}}{\text{Total number of beads}} = \quad\text{(Eq. 4)}$$

$$-\ln(1 - \text{fraction of "on" beads}).$$

In some cases, μ is also referred to herein as "$\text{AMB}_{digital}$." Rearranging Equation 4, the total number of analyte molecules in the fluid sample contained in the counted locations can be determined using Equation 5:

Number of analyte molecules=−ln(1−fraction of "on" beads)×(Total number of beads) (Eq. 5).

Therefore, the total number of molecules can be determined from the fraction of "on" beads for a given number of beads, and a measure of the concentration of analyte molecules in the fluid sample may be based at least in part on this number (as well as, e.g., any dilutions of the sample during the assay, the number and volume of the wells containing capture objects interrogated, etc). The number of beads with 1, 2, 3, 4, etc. associated analyte molecules can also be determined by calculating $P_\mu(1)$, $P_\mu(2)$, $P_\mu(3)$ etc. from the μ determined and Equation 1.

Table 1 demonstrates the potential utility of Poisson distribution adjustment. Column A shows the number of analyte molecules in the sample calculated from the molarity and volume tested. Column B shows the unadjusted number of molecules captured on beads, where any bead associated with any number (e.g., one, two, three, etc.) of analyte molecules is counted as being associated with a single analyte molecule. Column D is the Poisson adjusted data, wherein beads associated with two analyte molecules are counted as having two molecules bound, and beads associated with three molecules are counted as having three molecules bound, etc. The comparison of the unadjusted and adjusted data can be seen by comparing Columns C and E. These columns give the calculated capture efficiencies of the assay at each concentration, wherein the capture efficiency is the determined number of analyte molecules captured (unadjusted or Poisson adjusted) divided by the number of analyte molecules provided in the fluid sample, multiplied by 100%. Column C shows a calculation the capture efficiency using unadjusted data, and a reduction in capture efficiency is observed as the concentration of analyte molecules increases. Column E shows a calculation the capture efficiency using Poisson adjusted data. FIG. 1 is a graphical representation of the results of an exemplary Poisson distribution adjustment. The unadjusted data deviates from linearity with increasing concentration, while the data which has been subject to a Poisson distribution adjustment is substantially linear through a substantially portion of the plotted concentration range. Using the results shown in column D, the average number of analyte molecules per bead can be calculated (e.g., the Poisson adjusted number of molecules captured divided by the total number of beads addressed). In certain embodiments, the resulting average number of analyte molecules per bead may be used to prepare a calibration curve, as described herein.

TABLE 1

Poisson distribution adjustment

| [SβG] (aM) | Column A # of Molecules in the System | Column B Unadjusted #of Molecules Captured | Column C Digital Read Unadjusted Capture Efficiency | Column D Poisson adjusted # of Molecules Captured | Column E Poisson Adjusted Capture Efficiency |
|---|---|---|---|---|---|
| 0.35 | 21 | 28 | 132% | 28 | 132% |
| 0.7 | 42 | 33 | 79% | 33 | 79% |
| 3.5 | 211 | 159 | 75% | 159 | 75% |
| 7 | 421 | 279 | 66% | 279 | 66% |
| 35 | 2107 | 1778 | 84% | 1782 | 85% |
| 70 | 4214 | 3267 | 78% | 3280 | 78% |
| 350 | 21070 | 13514 | 64% | 13748 | 65% |
| 700 | 42140 | 30339 | 72% | 31552 | 75% |
| 3500 | 210700 | 122585 | 58% | 146380 | 69% |
| 7000 | 421400 | 178112 | 42% | 235716 | 56% |

Above a certain active bead percentage (i.e., where there is no longer a statistically significant fraction of beads present in the population that are not associated with any of analyte molecules or particles, or, potentially advantageously for situations where there may be a statistically significant fraction of beads present in the population that are not associated with any of analyte molecules or particles but that result in active bead percentages above a certain level—e.g., greater than or substantially greater than about 40%, or about 50%, or about 60%, or about 70% (or active location percentage, in embodiments where beads are not employed)) improvements in accuracy and/or reliability in the determination of analyte molecule concentration may potentially be realized by employing an intensity measurement based analog determination and analysis rather than or supplementary to a digital/binary counting/Poisson distribution adjustment as previously described. At higher active bead percentages, the probability of an active bead (e.g., positive reaction vessel) being surrounded by other active beads (e.g., positive reaction vessels) is higher and may in certain assay set ups create certain practical challenges to exclusively using the digital/binary determination method. For example, in certain embodiments, leakage of a detectable component into a reaction vessel from an adjacent reaction vessel may occur to some extent. Use of an analog, intensity level based technique in such situations can potentially yield more favorable performance.

Figure 2:
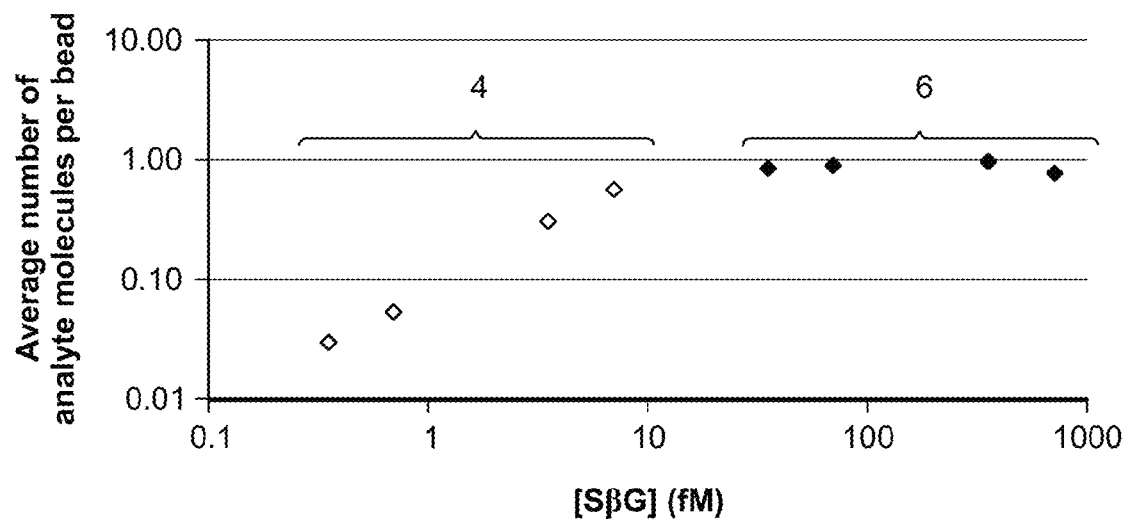
FIG. 2 shows a graph of the average number of enzymes bound per bead versus the concentration of enzymes in a fluid sample, according to one embodiment.

FIG. 2 illustrates a feature of the Poisson adjusted digital readout technique which may be Observed, in some cases, as the analyte concentration increases such that the number of active beads increases to higher levels. At some point, in certain embodiments, the concentration of analyte molecules may reach a level where the digital readout technique, with or without Poisson distribution adjustment, is no longer producing as linear a relationship with respect to concentration as may be desirable, and the analytical technique employed by the system/method of the invention may be altered such that an analog analysis method/system is employed. In analog analysis, the association of multiple analyte molecules at high concentrations with single beads may able to be more effectively and/or reliably quantified. The intensity of at least one signal from the plurality of reaction vessels which contains at least one analyte molecule may be determined. In some cases, the intensity determined may be the total overall intensity determined from all the reaction vessels interrogated containing at least one analyte molecule (e.g., the intensity of the reaction vessels is determined as a whole). In other cases, the intensity of each reaction vessel producing a signal may be determined and averaged, giving rise to an average bead signal (ABS).

To extend the dynamic range of assay methods/systems of the invention to combine both analog and digital analysis methods/systems, a "link" may be established relating the results/parameters of the two analysis methods/systems. This may be done, in certain cases, with the aid of a calibration curve. In some embodiments, a measure of the unknown concentration of analyte molecules in a fluid sample (e.g., test sample) may be determined at least in part by comparison of a measured parameter to a calibration curve, wherein the calibration curve includes data points covering both digital and analog concentration ranges, and hence, has an extended dynamic range as compared to a single mode (i.e., only digital or only analog) analysis method/system. The calibration curve may be produced by conducting the assay with a plurality of standardized samples of known concentration under conditions substantially similar to those used to analyze a test sample of unknown concentration. In one example, the calibration curve may transition from data determined using an analog measurement to a digital analysis system/method as the detected percentage of active beads is reduced to at or below a threshold value (e.g., about 40% active beads, or about 50% active beads, or about 60% active beads, or about 70% active beads, etc.).

To prepare a combined digital-analog calibration curve, in certain embodiments a linkage is made between the results obtained in the low concentration (digital) and high concentration (analog) analytical regimes. In certain embodiments, calibration curve relates analyte molecule concentration to a parameter defined as the average number of analyte molecules per bead, or AMB versus the concentration of molecules in solution. It should be understood, that while the following discussion features exemplary embodiments in which analyte molecules happen to be an enzyme, this is no means limiting, and in other embodiments, other types of analyte molecules or particles may be employed. For example, the analyte molecule may be a biomolecule, and the assay may involve the use of a binding ligand which comprises an enzymatic component. The AMB for a sample with a concentration falling in a range where digital analysis is preferred may be determined using a Poisson distribution adjustment, as described above. The AMB for a sample with a concentration falling in a range where analog analysis is preferred may be determined by converting an analog intensity signal (e.g., average bead signal) to an AMB using a conversion factor, as discussed below.

In a first exemplary embodiment, to prepare a calibration curve and determine an appropriate conversion factor, the assay is carried out on a calibration sample, wherein the percentage of active beads (or percentage of active locations, in embodiments where beads are not employed) is between about 30% and about 50%, or between about 35% and about 45%, or in some cases about 40%, or in some cases greater than 50%. The AMB for this sample can be calculated using a Poisson distribution adjustment, as described above. For this sample, the average bead signal (ABS) is also determined. A conversion factor (CF) relating the ABS and AMB may be defined, for example as according to Equation 6:

$$CF = \frac{AMB_{calibration\ sample}}{ABS_{calibration\ sample}}. \tag{Eq. 6}$$

Therefore, the regime where it is preferred to use an analog determination, the AMB for a sample (e.g., unknown sample, or a calibration sample with a concentration placing it in the analog region) may be calculated according to Equation 7:

$$AMB_{sample\ X} = CF \times ABS_{sample\ X} \tag{Eq. 7}.$$

Figure 3:
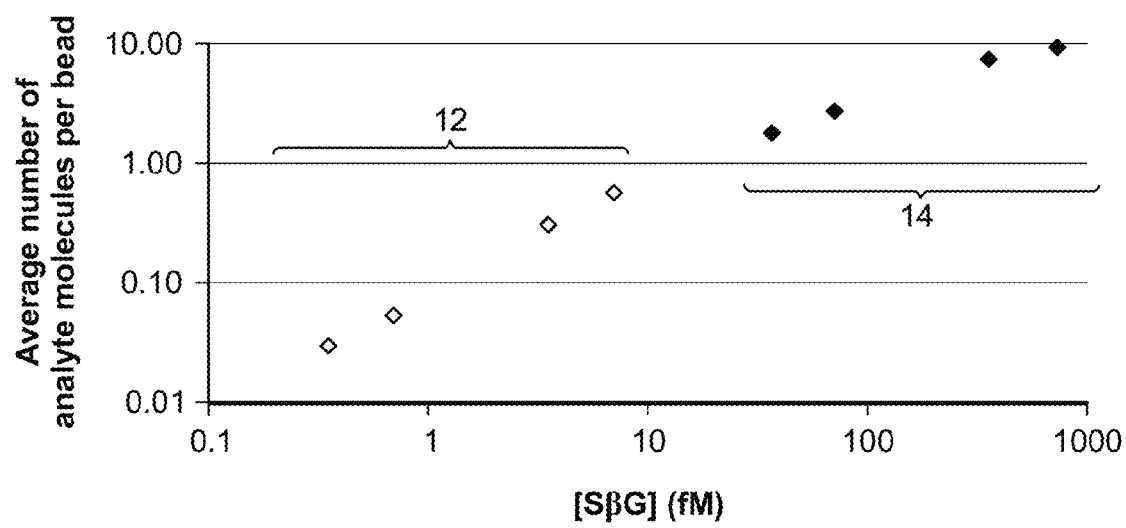
FIG. 3 shows a graph of the average number of enzymes bound per bead versus the concentration of enzymes in a fluid sample, according to one embodiment, wherein the average number of enzymes bound per bead is calculated using two different analytical methods.

For example, in one exemplary embodiment, a calibration curve and conversion factor may be determined as follows. In Table 2 shown below, the highest concentration of analyte molecules (e.g., enzymes in this exemplary embodiment) determined using a digital/binary read-out protocol (about 7 fM) gave rise to about 42.36% active wells. This digital signal was adjusted using Poisson distribution adjustment to determine the total number of bound molecules, and the AMB was determined to be 0.551. The data collected at this concentration level was also analyzed to determine the average bead signal (the ABS was equal to about 1041 fluorescent units). The analog-to-digital conversion factor was, therefore, 0.000529 AMB/fluorescent units, as calculated using Equation 6. For other samples with relatively high concentration ranges, the AMB value can be determined by applying this conversion factor (e.g., as described in Equation 7). Table 2 illustrates the conversion of average bead signal (e.g., average beaded well intensity in Table 2) to AMB using an analog to digital conversion factor, as well as the digitally determined AMB values at some lower concentrations. The combined digital/analog calibration data can be plotted on a single calibration curve of AMB values versus concentration. FIG. 3 shows a graphical representation of converted analog data plotted together with digital data. The analog values are converted to AMB (data points 14) and plotted along with AMB values in the Poisson adjusted digital readout range (data points 12).

TABLE 2

Conversion of the analog readout to AMB

|  | fM | Digital 'on' percentage | Poisson Adjusted Digital AMB | Avg. Beaded Well intensity (Analog Measure) | Analog Converted to Poisson Adjusted AMB using conversion factor | Combined AMB |
|---|---|---|---|---|---|---|
| ANALOG | 700 | — | — | 17243 | 9.130 | 9.130 |
|  | 350 | — | — | 13996 | 7.411 | 7.411 |
|  | 70 | — | — | 5178 | 2.742 | 2.742 |
|  | 35 | — | — | 3279 | 1.736 | 1.736 |
| DIGITAL | 7 | 42.36% | 0.551 | 1041 | — | 0.551 |
|  | 3.5 | 26.21% | 0.304 | — | — | 0.304 |
|  | 0.7 | 5.24% | 0.054 | — | — | 0.054 |
|  | 0.35 | 2.93% | 0.030 | — | — | 0.030 |

The dynamic range demonstrated by the described approach based on the experiments tabulated in Tables 1 and 2 was greater than 6 logs. Generally, the dynamic range of an analysis system/method is bounded by the lower limit of detection for digital readout (e.g., in the specific example described, about 227 zM) and the highest concentration tested and accurately quantifiable by analog readout (e.g., in this example, about 700 fM), i.e., 6.5 log. This dynamic range may be compared to the dynamic range of about 3 logs which can be achieved for the same test samples on a plate reader that only has the ability to measure an analog signal from an ensemble of molecules.

In a second exemplary embodiment, at low ratios of analyte molecules to beads, where there are a significant number of beads that are associated with no analyte molecules ("off" beads), the number of active, analyte molecules-associated (or "on") beads relative to the total number of beads detected may be are used to determine an AMB (i.e., $AMB_{digital}$) via Poisson statistics as described above. At higher ratios, however, a modified approach is taken from that described above in the first exemplary embodiment for preparing a calibration curve. In this embodiment, at higher ratios of analyte molecules to beads, when most beads have one or more analyte molecules bound, and the counting approach becomes less accurate, an AMB (i.e., $AMB_{analog}$) is determined from the average fluorescence intensity of wells containing a bead in the array ($\bar{I}_{bead}$). To convert $\bar{I}_{bead}$ to AMB in the analog regime, images with <10% active beads may be used to determine the average analog intensity of a single enzyme molecule ($\bar{I}_{single}$). The ratio of $\bar{I}_{bead}$ to $\bar{I}_{single}$ over all beads provides an analog AMB, and a calibration curve can prepared as follows. The dynamic range of an assay may be extended beyond the digital regime by measuring the average fluorescence intensity of wells that contain beads to determine the number of molecules (e.g., enzymes) associated with each bead detected. In this embodiment, the AMB can be determined from the average fluorescence intensity value of the active beads ($\bar{I}_{bead}$) and the average fluorescence intensity generated by a single bead (e.g., a single enzyme; $\bar{I}_{single}$). The AMB of an array in the analog range ($AMB_{analog}$) is defined by Equation 8:

$$AMB_{analog} = \frac{f_{on} \times \bar{I}_{bead}}{\bar{I}_{single}} \quad \text{(Eq. 8)}$$

To determine $\bar{I}_{single}$, the $AMB_{digital}$ (e.g., see Equation 4) and $AMB_{analog}$ (Equation 8) can be equated in terms at fractions of active beads where the beads predominantly associate with either one or zero molecules dominate, for example, as shown in Equation 9. In some cases, these values are equated when there is negligible contribution from substrate depletion (e.g., as described herein). In some cases, an array is analyzed and if the fractions of "on" beads <0.1 the condition is taken as meeting these criteria:

$$\bar{I}_{single} = \frac{f_{on} \times \bar{I}_{bead}}{-\ln[1 - f_{on}]}, \quad \text{(Eq. 9)}$$

in arrays where $f_{on} < 0.1$.

AMB can then plotted for both the digital ($AMB_{digital}$ (Equation 4)) and analog ($AMB_{analog}$ (Equation 8)) ranges, and the two curves may be combined into one calibration curve.

When combining the digital and analog data in this second embodiment, an experiment may be employed to determine $\bar{I}_{single}$. The experiment may employ a sample wherein the fraction of active beads is less than about 5%, about 10%, about 15%, about 20%, about 25%, or more. In some cases, the fraction of active beads is about 10%. This may accomplished, as described above, by using calibration data points which cover this range, or specific control samples known to have a digital signal in this range. With two or three concentrations in a calibration curve with $f_{on} < 0.1$, the intensity of individual beads (e.g., the kinetic activities of individual enzyme molecules) can be averaged to determine $\bar{I}_{single}$. In the case of enzymes, the averaging of the intrinsic variation associated with single enzyme molecule velocities (e.g., the enzyme turnover rate) may be such that little to no significant variation to the $\bar{I}_{single}$ measurement is observed. The uncertainty in the mean single enzyme intensity ($\bar{I}_{single}$) as a function of N measurements can be given by $\sigma_{\bar{I}_{single}}/\sqrt{N}$, where $\sigma_{\bar{I}_{single}}$ is the width parameter of the normally distributed single enzyme molecule intensities. For example, with a width parameter of 30% of the average single enzyme velocities, the uncertainty added to the mean value $\bar{I}_{single}$ was 1% when averaging over 1000 single molecule measurements. When the fraction of active beads increases (e.g., 10% and greater), theoretically both digital counting and analog intensities could be used to determine AMB. Below a certain percentage of active beads (e.g., less than about 20%, less than about 15%, less than about 10%, less than about 5%, or less), the contribution of beads associated with multiple enzymes may be too small such that $\bar{I}_{bead}$ does not vary above the measurement noise of % active beads and the analog approach may not provide accurate results.

As $f_{on}$ approaches 100%, as described above, counting "on" and "off" beads may not provide an accurate measurement of the AMB. At intermediate percentages of "on" beads, various factors may be considered to determine the threshold of the fraction of active beads below which $AMB_{digital}$ (Equation 4) is used and above which $AMB_{analog}$ (Equation 8) is used. The choice of this threshold may be illustrated by plotting the imprecision in AMB arising from the variation in digital and analog signals.

Figure 4A:
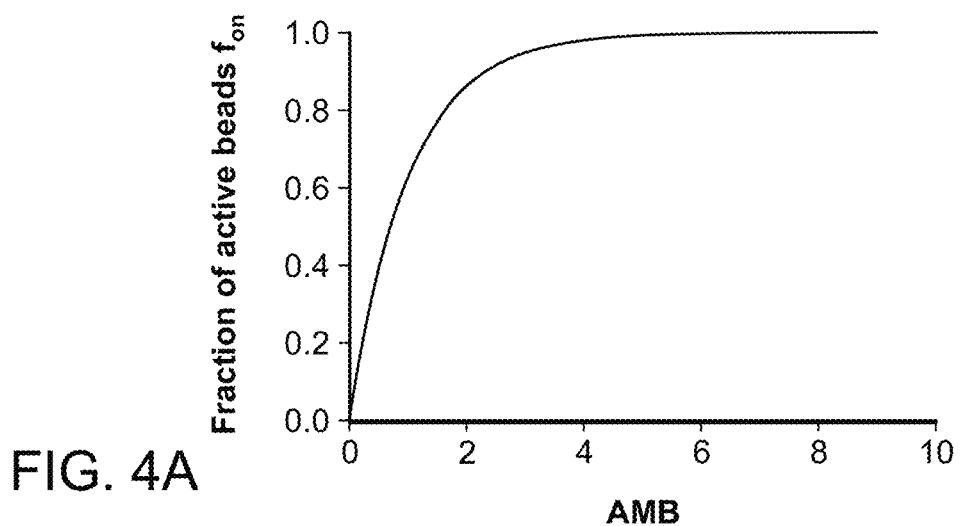
FIG. 4A shows a plot of the fraction of active beads versus the effective analyte concentration, given by the average molecule per bead (AMB), determined from digital counting using the Poisson distribution, accordingly to one embodiment.
Figure 4B:
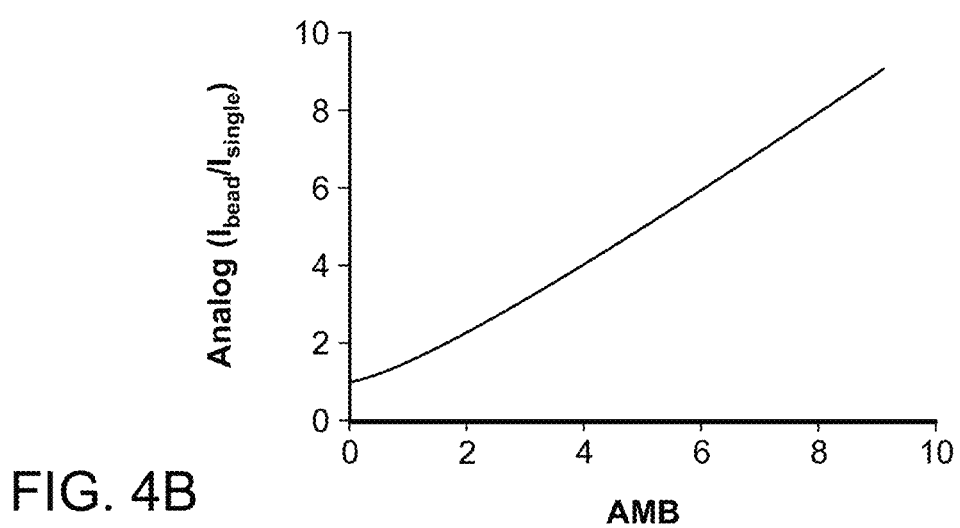
FIG. 4B shows a plot of analog intensity ($I_{bead}/I_{single}$) as a function of effective concentration, AMB, accordingly to one embodiment.
Figure 4C:
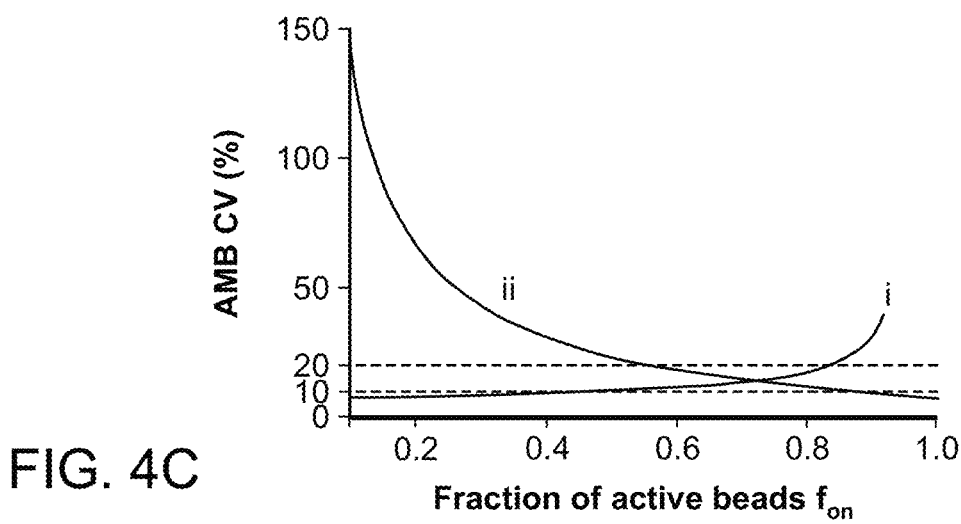
FIG. 4C shows plot of the imprecision in AMB (% CV) as a function of the number of active beads from (i) digital analysis and (ii) analog analyses, according to one embodiment.
Figure 5A:
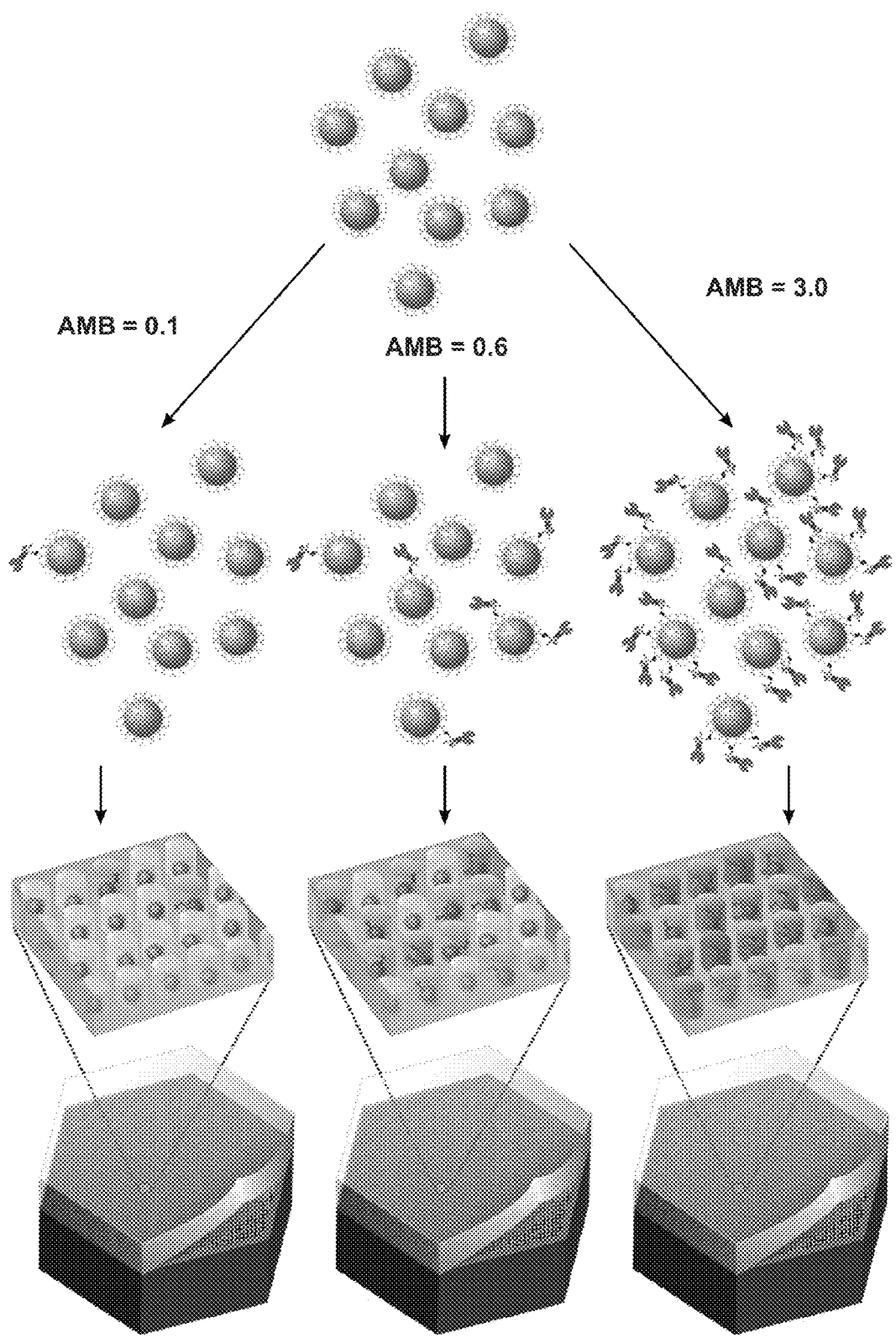
FIG. 5A shows a schematic diagram of an assay protocol of an embodiment of the present invention, wherein AMB=0.1 (left), AMB=0.6 (middle), and AMB=3.
Figure 5D:
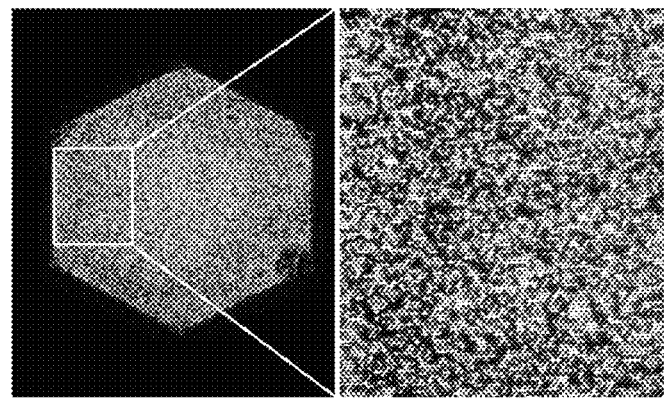
FIGS. 5B-D show fluorescence images generated using an assay according to some embodiments of singulated beads in individual wells at approximate AMBs of (D) 0.1, (E) 0.6, and (F) 3.0.
Figure 5C:
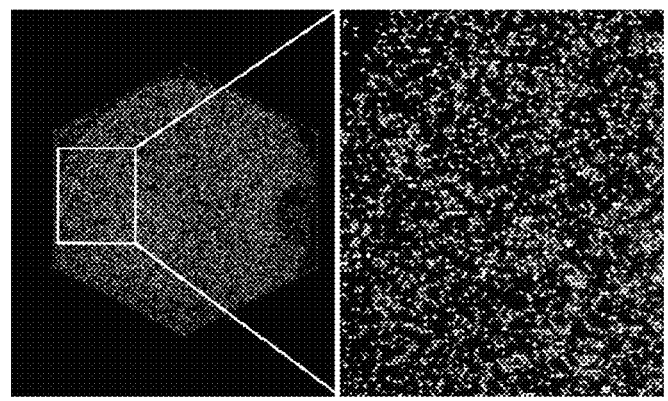
Figure 5B:
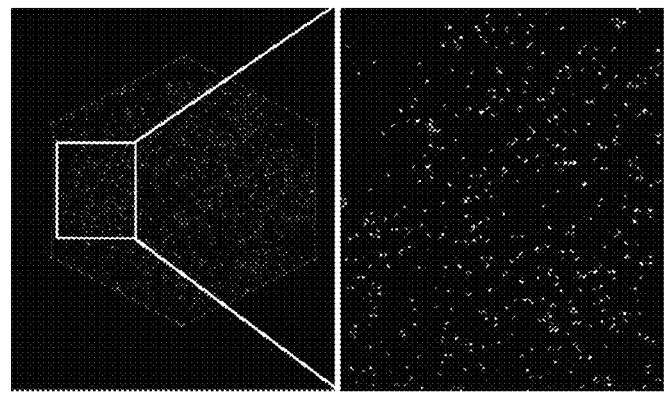

For example, FIG. 4A shows a plot of fraction of active beads against the effective concentration, given by AMB, determined from digital counting using the Poisson distribution (Equation 4). As concentration increases, the slope of % active gets shallower and signal imprecision leads to greater imprecision in concentration determined. FIG. 4B shows a plot of analog intensity ($I_{bead}/I_{single}$) as a function of effective concentration, AMB (Equation 8). At low concentrations, variation in intensity measurements can make it difficult to detect small increases in multiple enzymes, and CVs of extrapolated AMB are high. FIG. 4C shows a plot of the imprecision in AMB (% CV) as a function of $f_{on}$ from (i) digital and (ii) analog analyses assuming a fixed signal CV of 7.1% for both methods. In some cases, the digital-to-analog threshold (e.g., the threshold where there is a transition of determining the concentration between using a digital analysis (e.g., Equation 4) or an analog analysis (e.g., Equation 8) is about 40%, about 50%, about 60%, about 70%, about 80%, or between about 50% and about 80%, or between about 60% and about 80%, or between about 65% and about 75%. In a particular embodiment, the threshold is about 70%, or between about 75% and about 85%. See Examples 8 and 9 for sample experiments.

FIG. 5 depicts an assay where determinations are made at varying AMBs. FIG. 5A (left) shows an AMB=0.1, wherein each active beads are statistically associated predominantly with a single analyte molecule and digital analysis may be conducted. FIG. 5A (middle) shows an AMB=0.6, wherein significant number of active beads are associated with more than one analyte molecule, and an analog or digital analysis may be conducted. If a digital analysis is conducted, multiple analyte molecules per bead may be accounted for using a Poisson distribution analysis. FIG. 5A (right) shows an AMB=3, wherein substantially all of the beads are associated with more than one analyte molecule. In this case, the average number of analyte molecules per bead may be quantified by measurement of the average fluorescence intensity of the active beads and from knowledge of the average fluorescence intensity generated by a single analyte molecules (e.g., enzyme), as described herein. FIG. 5B-D show fluorescence images generated using an assay as described herein of singulated beads in individual wells at approximate AMBs of (D) 0.1, (E) 0.6, and (F) 3.0.

Once a calibration curve has been developed which relates the AMB to a measure of the concentration of analyte molecules in a fluid sample, a measure of concentration of analyte molecules in a test sample (e.g., an unknown sample) may be determined using the calibration curve. An assay may be carried out in a similar manner as was conducted for the calibration samples (e.g., including immobilizing the analyte molecules with respect to a plurality of beads, and spatially segregating at least a portion of the plurality of beads into a plurality of reaction vessels). Following spatially segregating a plurality of beads into a plurality of reaction vessels, at least a portion of the plurality of reaction vessels may be interrogated, in certain embodiments a plurality of times. For example, at least about 1, at least about 2, at least about 3, at least about 4, at least about 5, at least about 6, at least about 7, at least about 8, at least about 9, at least about 10, or more, interrogations may be conducted, the interrogations separated by a period of time of, for example, about 1 second, about 2 seconds, about 5 seconds, about 10 seconds, about 20 seconds, about 30 seconds, about 40 seconds, about 50 seconds, about 1 minute, or more. Each interrogation may produce one set of data. The data may be analyzed to determine the percentage of beads associated with at least one analyte molecule (e.g., the percentage active beads) (or the percentage of active locations, for example, in embodiments where beads are not employed).

In some embodiments, if the percentage of active beads (or locations) is less than about 80%, less than about 70%, less than about 60%, less than about 50%, less than about 45%, less than about 40%, less than about 35%, less than about 30%, less than about 25%, or less than about 20%, the measure of the concentration of analyte molecules or particles in the fluid sample may be based at least in part on the number/percentage of locations determined to contain at least one analyte molecule or particle. That is, at least one set of data may be analyzed using a digital analysis method (which may further include adjustment via a Poisson distribution adjustment) as described herein. For example, the AMB may be determined as described herein (e.g., using a Poisson distribution adjustment) and the concentration may be determined by comparison of the AMB to the calibration curve. In some cases, the set of data used may be a data set collected later in time (e.g., to ensure sufficient time for an enzymatic substrate to be converted to a detectable entity). The measure of the concentration of analyte molecules in a fluid sample may be based at least in part on comparison of a measured parameter to a calibration curve (e.g., formed at least in part by determination of at least one calibration factor).

In other embodiments, for example if the percentage of active beads is relatively high, e.g., greater than about 30%, greater than about 35%, greater than about 40%, greater than about 45%, greater than about 50%, greater than about 60%, greater than about 70%, greater than about 80%, or more, the measure of the concentration of analyte molecules or particles in the fluid sample may be based at least in part on measurement of an intensity level of the at least one signal indicative of the presence of a plurality of analyte molecules or particles. That is, the data may be analyzed using one of the analog analysis methods, as described herein. For example, the AMB may be determined for the sample using Equation 7 or Equation 8. The AMB may be compared with the calibration curve to determine a measure of the concentration of analyte molecules in the fluid sample. In some cases the set of data used may be a data set collected earlier in time (e.g., such as to limit difficulties associated with substrate depletion, photobleaching, etc., as described herein). The measure of the concentration of analyte molecules in a fluid sample may be based at least in part on comparison of a measured parameter to a calibration curve (e.g., formed at least in party by determination of at least one calibration factor).

In yet other embodiments, for example for intermediate concentration ranges where the percentage of active beads may be between about 30% and about 80%, or between about 40% and about 70%, or between about 60% and about 80%, or between about 65% and about 75%, or between about 30% and about 50%, or between about 35% and about 45%, or near 40%, the measure of the concentration of analyte molecules or particles in the fluid sample may be based on an average of the measure of the concentration of analyte molecules or particles as determined by a digital analysis method and as determined by an analog analysis method. That is, at least one set of data may be analyzed using a digital analysis method and/or one of the analog analysis methods, as described herein. Upon determination of the AMB (from the digital and/or analog analysis method and/or average of the two), the AMB may be compared with the calibration curve to determine a measure of the concentration of analyte molecules in the fluid sample.

In some embodiments, in addition to determining a signal indicative of the presence/concentration of analyte molecules, at least one background signal may be determined. In some cases, prior to calculation of an AMB from a set of data, a background data set may be subtracted from the analyzed data set. The background data set may be collected by addressing the array of locations prior to spatially segregating the test sample (e.g., analyte molecules that may be immobilized on a plurality of beads) into the locations and/or following spatial separation but prior to exposure to a plurality of enzymatic substrates (or other precursor labeling agents) to develop the signal.

In some embodiments, in addition to a plurality of capture objects for analyte capture, a plurality of control objects may also be provided and/or employed. A control object(s) may be useful for a variety of purposes including, but not limited to, identification of the orientation of the plurality of locations (e.g., in the case where the plurality of locations is formed as an array of reaction sites, reaction vessels, etc.), to help determine the quality of the assay, and/or to help calibrate the detection system (e.g., optical interrogation system), as described below. It should be understood, that more than one type of control object may be present in any assay format (e.g., a first type of control object to determine quality of the assay and a second type of control object to act as a location marker), or a single type of control object may have more than one of the above-described functions.

In some cases, the control objects used to identify the orientation of the plurality of locations (e.g., reaction vessels, sites, etc.) on an array (e.g., function as location marker(s) for an array). For example, a control object may be randomly or specifically distributed on an array, and may provide one or more reference locations for determining the orientation/position of the array. Such a feature may be useful when comparing multiple images of a portion of the array at different time intervals. That is, the positions of control objects in the array may be used to register the images. In some cases, the control objects may be use to provide reference locations in embodiments where a plurality of images of small overlapping regions are being combined to form a larger image.

The presence of control objects in an assay may provide information regarding the quality of the assay. For example, if a location is found to contain a control object comprising an enzymatic component but no labeling agent is present (e.g., the product of which would be present upon exposure of a control object comprising an enzymatic component to a precursor labeling agent), this gives an indication that some aspect of the assay may not be functioning properly. For example, the quality of the reagents may be compromised (e.g., concentration of precursor labeling agent is too low, decomposition of the precursor labeling agent, etc.), and/or perhaps not all of the locations were exposed to the precursor labeling agent.

In some embodiments, the control objects may be used to calibration the detection system. For example, the control objects may output an optical signal which may be used to calibration an optical detection system. In some embodiments, the control objects can be characterized and doped with a particular characteristic (e.g., fluorescence, color, absorbance, etc.) which can act as a quality control check for the detection system performance.

In some cases, the control objects may be used to standardize or normalize the system to account for variations of the performance and/or characteristics of different system components in different assays, over the course of time, etc. (e.g., detection system, arrays, reagents, etc.) between different potion of an array used in a test, and/or between two different arrays. For example, experimental set-up, parameters and/or variations may lead to changes the intensity of a signal (e.g., fluorescence signal) produced from a single array at different time points, or between at least two arrays at simultaneous or different time points. In addition, in a single array, different portions of the array may produce different background signals. Such variations may lead to changes in calibration signals (e.g., determination of an average bead signal) between arrays, portions of and array or at multiple times, which can lead to inaccurate determinations in some cases. Non-limiting examples of parameters that may cause variation include labeling agent concentration, temperature, focus, intensity of detection light, depth and/or size of the locations in an array, etc. To account for the effects of some or all of such variations, in some embodiments, a plurality of control objects may be utilized. In certain instances, such control objects are essentially free of association with analyte molecules or particles. In certain embodiments, less than about 20%, about 10%, about 5%, about 1%, etc. of the control objects are associated with analyte molecules or particles. The control objects may be distinguishable from the capture objects (e.g., each may produce a distinguishable signal) and the system may be configured such that any analyte molecules associated with a control object are not accounted for in the concentration determination of the analyte molecules. The signals from the control objects may be used to normalize the interrogation values between different arrays, or in areas of a single array. For example, because the signals from the control objects should be approximately equal between arrays and/or about a single array, the control object signals may be normalized to an appropriate value and the signals of the non-control objects (e.g., the capture objects associated with an analyte molecule) may be adjusted accordingly.

As a specific example, in some cases, a group of control objects being equal to or less than 10% active may be provided to the array. The $I_{single}$ from the capture objects may be determined by equating the digital AMB (e.g., Equation 4) and analog AMB (e.g., Equation 8). At low concentration of analyte molecules in the fluid sample, the percentage of active control objects in is an analog region and $AMB_{analog}$ for the fluid sample may be calculated using the $I_{single}$ determined using the control objects (e.g., not using an $I_{single}$ calculated using capture objects associated with the analyte molecules from the fluid sample). This approach may reduced any imprecision in $AMB_{analog}$ caused by array-to-array, intra-array, and/or day-to-day variation in $I_{single}$ as this value is determined using the control objects (e.g., which may be calibrated with other determinations and/or interrogations of control objects).

The control objects may be dispersed throughout the assay array of locations or may be segregated in a set of locations separated from the assay capture objects. For example, a segregated portion of capture objects may be provided in a region on the assay site separate from the region containing capture objects, and the value of $I_{single}$ for these sites provides a specific denominator for Equation 8 for this particular portion of an array or this set of arrays. In such cases, the capture beads do not necessarily need to be distinguishable from the control objects since the control objects are spatially separated from the capture objects.

In some embodiments, an increased dynamic range may be produced or enhanced through use of an imaging camera with a high resolution. For example, the above measurements (e.g., given in Table 2) were obtained using a 12-bit camera. The "n"-bit characterization of the electronic resolution of a camera shows that $2^n$ quantized analog intensity units can be determined. So for a 12-bit camera, 4096 discrete intensity increments may be distinguished. Thus, a dynamic range of the order of 3.6 logs can be achieved typically, and increasing the resolution of the camera may expand the dynamic range of concentrations which may be accurately measured in the digital analysis regime, as described herein.

In general, practice of the invention is not particularly limited to any specific dynamic ranges or camera types. Instead of or in addition to the techniques discussed above, other methods/systems may be employed to expand or further expand dynamic range. For example, detection of a greater quantity of beads (or other capture objects) may expand the dynamic range. In the examples whose results are tabulated in the Tables above, about 13% of beads which were exposed to the sample comprising analyte molecules were detected. However in other embodiments, increasing the number of reaction vessels (e.g., locations) interrogated and/or by using cameras with larger fields of view, up to 100% of the beads which were exposed to the sample could be detected. By detecting an increased number of beads, the dynamic range could be expanded by at least 1 more log in the digital counting end of the range (e.g., from about 4.5 logs to about 5.5 logs, extending the entire range to about 7.5 logs). By using more beads, dynamic range can also be extended by lowering the limit of detection (LOD) of the digital read-out analysis method/system. For example, by increasing the number of beads, the limiting effects of Poisson noise may be reduced because more events could be counted. In certain embodiments, it may be possible, with one or more of the above described inventive dynamic range extending techniques to detect a single analyte molecule per sample. The dynamic range can also be extended in the higher concentration, analog analysis range. For example, increasing the electronic resolution of the camera (e.g., linescan with a 24-bit photomultiplier tube or use of advanced 16- and 18-bit imaging cameras) may extend the dynamic range of analog measurements.

As described below, for embodiments in which a precursor labeling agent is used to facilitate the production of a detectable signal (e.g., assays where that use enzyme labeled analyte molecules or binding ligands attached to analyte molecules), acquisition of images at shorter time intervals after the analyte molecules have been segregated into the plurality of locations and exposed to a precursor labeling agent that is converted by to a detected labeling agent (i.e. after shorter incubation time) may also be able to extend the dynamic range as fewer labeling agent molecules (e.g., converted enzymatic substrate molecules) may be detected. For example, in the example whose results are tabulated in Table 2, the lowest analog measurement was on 1041 analog counts (see Table 2). The 12-bit camera used has a dynamic range from 16 counts to 65536 counts. In some embodiments, by reducing the incubation time, the dynamic range may be extended by acquiring the measurement at the low end of the counts (e.g., the lowest analog measurement could potentially be made at 16 counts (e.g., instead of 1041 counts)) and thus, the total analog dynamic range would be 3.6 logs, equating to a total digital+analog dynamic range of about 8.1 logs. A similar effect could be achieved by reducing the acquisition time of the image (e.g., how long the shutter is open for light to fall on the CCD chip). Again, that time could be minimized to give the lowest possible analog response at the digital-to-analog switch point and maximize dynamic range. These changes may potentially lead to dynamic range in excess of 9 logs for a 12-bit camera in certain embodiments. For example, by implementing the changes to the digital and analog measurements described here for a 12-bit camera a total dynamic range of (5.5 log digital+3.6 log analog) 9.1 logs may be achieved. By using 16-, 18-, and 24-bit imaging system, that dynamic range could be extended to 10.3, 10.9, and 12.7, logs respectively.

In some cases, the digital-to-analog conversion methods described herein may include techniques and analysis to account for substrate depletion and/or photobleaching. Substrate depletion may occur in embodiments where the assay involves detecting a labeling agent (e.g., fluorescent enzymatic product) which is formed from a precursor labeling agent (e.g., enzymatic substrate) upon exposure to an analyte molecule (or binding ligand associated with an analyte molecule). It may be advantageous to account for substrate depletion, for example, in embodiments where a reaction vessel contains more than one analyte molecule (or binding ligand). For example, in a certain experiment, consider that approximately 2.1 million substrate molecules are available for turnover in a reaction vessel. In this example, the enzymatic component, beta-galactosidase has a turnover rate of $186 \text{ s}^{-1}$ at 100 µM substrate concentration. If there is only one enzymatic component or molecule (or binding ligand) per bead (e.g., present in a reaction vessel), that enzymatic component retains 99% of its activity over a duration of a three minute experiment. If, on the other hand, there are on average 50 enzymatic components or molecules per bead (or per reaction vessel, as in a higher concentration sample), approximately 43% of the overall activity may be lost of the duration of the experiment due to substrate depletion. This loss in overall reaction chamber activity can result in a decreased intensity value than would be expected from a chamber containing ten enzymatic components or molecules.

To mitigate substrate depletion effects on the accuracy of analog measurements, in some embodiments, various techniques may be employed, two examples of which are discussed here. First, the duration of the time to collect the data set which is analyzed may be reduced. For example, fluorescent images at t=0 and t=30 s may be used to calculate the intensity value instead of a longer duration (e.g., t=0 and t=150 s). Performing a measurement over a shorter time period may reduce the amount of substrate that is depleted, and may aid in maintaining a linear rate of fluorescent product formation. Additionally, exposing the reaction chamber containing fluorescent product to excitation light twice (e.g., at t=0 and t=30) versus a larger number of times (e.g., at t=0, 30, 60, 90, 120, 150 s) may reduce photobleaching effects. Table 3 illustrates the reduction in enzyme activity over time due to substrate depletion for an exemplary assay embodiment.

TABLE 3

Reduction in enzyme activity over time
100 µM RDG

| | # enz/beaded well | | |
|---|---|---|---|
| | 1 | 5 | 10 |
| turnover rate decline over time t (s) | | | |
| 0 | 505 | 505 | 505 |
| 30 | 504 | 498 | 492 |
| 60 | 502 | 492 | 478 |
| 90 | 501 | 485 | 464 |
| 120 | 500 | 478 | 448 |
| 150 | 498 | 471 | 432 |
| 180 | 497 | 464 | 416 |
| % activity remaining from t = 0 t (s) | | | |
| 0 | 100% | 100% | 100% |
| 30 | 100% | 99% | 97% |
| 60 | 100% | 97% | 95% |
| 90 | 99% | 96% | 92% |
| 120 | 99% | 95% | 89% |
| 150 | 99% | 93% | 86% |
| 180 | 98% | 92% | 82% |

Figure 6:
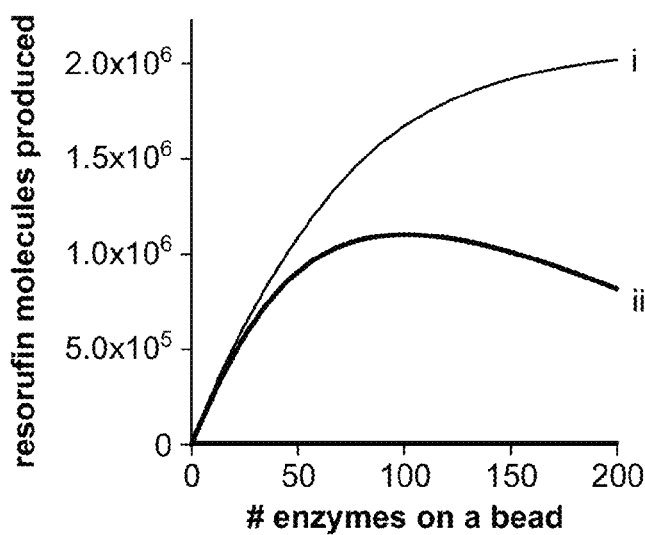
FIG. 6 shows a plot of the number of resorufin molecules produced as a function of the number of enzymes on a bead, according to some embodiments.

For example, FIG. 6 shows a theoretical curve of the amount of RGP converted into resorufin over the course of an assay measurement from a 100 µM RPG solution as a function of the number of enzyme molecules in a sealed well containing a bead, taking substrate depletion into account. Assuming that the assay is conducted using a camera with unlimited sensitivity (e.g., not limited by the number of bits) and imaging starting immediately after sealing, an assay may remain approximately linear to over AMB=50. Specifically, FIG. 6 shows a plot of the number of resorufin molecules produced during a 150 second experiment as a function of the number of enzymes on a bead wherein is the theoretical limit of a modeled where (i) image acquisition begins at t=0, immediately when the seal is made, and before any RGP is converted into resorufin; and (ii) where image acquisition begins at t=45 second after sealing.

Another technique which may be employed to mitigate the effects of substrate depletion involves increasing the substrate concentration. The $K_m$ of the enzyme/substrate pair in the above example was about 62 µM. The turnover rate of an enzyme is defined by the substrate concentration as elucidated by the Michaelis-Menten equation. At substrate concentrations much greater than the $K_m$, the enzyme turnover rate may begin to plateau. For example, at about 400 µM substrate, the average enzyme turnover rate is about 707 s$^{-1}$, while at about 200 µM the turnover rate is about 624 s$^{-1}$, and at about 100 µM the average turnover is about 504 s$^{-1}$. Reducing the concentration of the substrate in half from about 400 µM to about 200 µM results in about 11% reduction in turnover rate, while reducing the concentration of substrate from about 200 µM to about 100 µM results in about 20% reduction in turnover rate. Consequently, if substrate depletion occurs during an assay measurement while using high substrate concentrations, the depletion may have a smaller effect on the enzyme turnover rate as compared to depletion occurring when using a lower substrate concentration (e.g., close to $K_m$). Table 4 illustrates an example of the change in depletion effects as the substrate concentration is altered.

TABLE 4

Depletion effects as substrate concentration is altered

| 100 µM RDG turnover rate decline over time t (s) | # enz/beaded well 10 | 200 µM RDG turnover rate decline over time t (s) | # enz/beaded well 10 |
|---|---|---|---|
| 0 | 505 | 0 | 624 |
| 30 | 492 | 30 | 618 |
| 60 | 478 | 60 | 611 |
| 90 | 464 | 90 | 605 |
| 120 | 448 | 120 | 597 |
| 150 | 432 | 150 | 590 |
| 180 | 416 | 180 | 582 |

| % activity remaining from t (s) | # enz/beaded well 10 | % activity remaining from t (s) | # enz/beaded well 10 |
|---|---|---|---|
| 0 | 100% | 0 | 100% |
| 30 | 97% | 30 | 99% |
| 60 | 95% | 60 | 98% |
| 90 | 92% | 90 | 97% |
| 120 | 89% | 120 | 96% |
| 150 | 86% | 150 | 95% |
| 180 | 82% | 180 | 93% |

Figure 7:
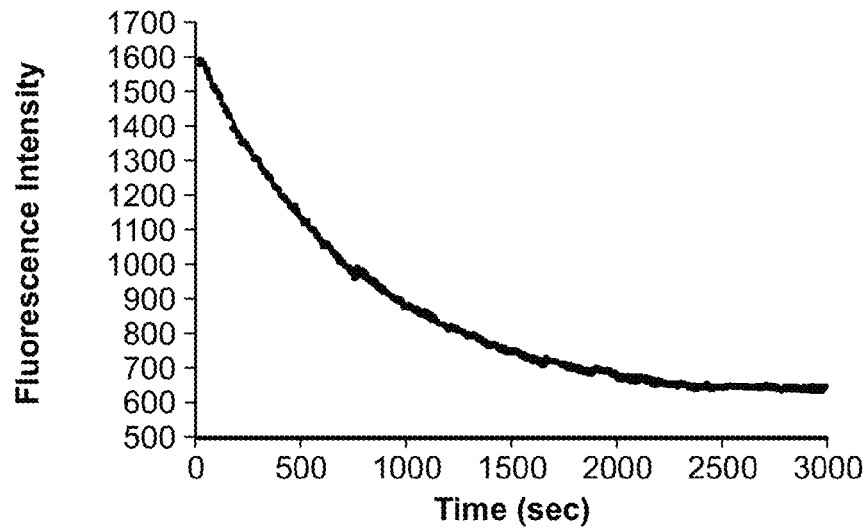
FIG. 7 shows a graph of the fluorescence intensity versus time, which may be used to determine the rate of photobleaching, according to some embodiments.

To mitigate photobleaching effects on raw fluorescence intensity, in some embodiments, the photobleaching rate of the fluorescent product may be determined. In the example shown in FIG. 7, the photobleaching rate was determined by enclosing a solution containing a fluorescent product being detected (10 µM resorufin) in the reaction vessels and monitoring the fluorescence decrease every 15 s with an exposure time of 2000 ms over 50 min. An exponential fit of the data yielded a photobleaching rate, $k_{ph}$, of 0.0013 s$^{-1}$ (see FIG. 7). A unique $k_{ph}$ can be determined for the specific optical parameters used in each assay system set-up and can be used to adjust the data set collected for the photobleaching effects on raw fluorescence intensities.

The following sections provide additional description, examples and guidance related to various aspects of analytical assay methods/systems, analyte molecules, analyzer systems, etc., that may be used to practice various embodiments of the inventive analysis methods/systems described above. Additional information may also be found in U.S. patent application Ser. No. 12/731,130, entitled "Ultra-Sensitive Detection of Molecules or Particles using Beads or Other Capture Objects" by Duffy et al., filed Mar. 24, 2010; International Patent Application No. (not yet determined), entitled "Ultra-Sensitive Detection of Molecules or Particles using Beads or Other Capture Objects" by Duffy et al., filed Mar. 1, 2011 (Attorney Docket No. Q0052.70011 WO00); U.S. Patent Application No. 20070259448, entitled "Methods and arrays for target analyte detection and determination of target analyte concentration in solution," by Walt et al., filed Feb. 16, 2007; U.S. Patent Application No. 20070259385, entitled "Methods and arrays for detecting cells and cellular components in small defined volumes," by Walt et al., filed Feb. 16, 2007; U.S. Patent Application No. 20070259381, entitled "Methods and arrays for target analyte detection and determination of reaction components that affect a reaction" by Walt et al., filed Feb. 16, 2007; U.S. patent application Ser. No. 12/731,135, entitled "Ultra-Sensitive Detection of Molecules using Dual Detection Methods" by Duffy et al., filed Mar. 24, 2010; International Patent Application No. (not yet determined), entitled "Ultra-Sensitive Detection of Molecules using Dual Detection Methods" by Duffy et al., filed Mar. 1, 2011 (Attorney Docket No. Q0052.70012WO00); International Patent Application No. PCT/US07/019,184, entitled "Methods for Determining The Concentration of an Analyte In Solution" by Walt et al., filed Aug. 20, 2007; and International Patent Application No. PCT/US09/005,428, entitled "Ultra-Sensitive Detection of Molecules or Enzymes" by Duffy et al., filed Sep. 9, 2009, herein incorporated by reference.

Methods and Systems for Segregating Analyte Molecules into Arrays of Locations

In certain embodiments, the assay methods and systems of the present invention employ a step of spatially segregating analyte molecules into a plurality of locations to facilitate detection/quantification, such that each location comprises/contains either zero or one or more analyte molecules. Additionally, in some embodiments, the article comprising the locations is configured in a manner such that each location can be individually addressed. While exemplary embodiments for spatially segregating a plurality of analyte molecules into a plurality of locations are described herein, numerous other methods may potentially be employed.

In some embodiments, an inventive method for determining a measure of the concentration of analyte molecules in a fluid sample comprises detecting analyte molecules immobilized with respect to a binding surface having affinity for at least one type of analyte molecule. In certain embodiments the binding surface may form (e.g., a surface of a well/reaction vessel on a substrate) or be contained within (e.g., a surface of a capture object, such as a bead, contained within a well) one of a plurality of locations (e.g., a plurality of wells/reaction vessels) on a substrate (e.g., plate, dish, chip, optical fiber end, etc). At least a portion of the locations may be addressed and a measure indicative of the number/percentage of the locations containing at least one analyte molecule or particle may be made. In some cases, based upon the number/percentage, a measure of the concentration of analyte molecules or particles in the fluid sample may be determined. The measure of the concentration of analyte molecules or particles in the fluid sample may be determined of a digital analysis method/system optionally employing Poisson distribution adjustment and/or based at least in part on a measured intensity of a signal, as has been described in detail above.

As described above, in embodiments where the analyte molecules are immobilized with respect to a plurality of capture objects, the locations addressed may be locations which contain at least one capture object (e.g., either associated with or not associated with any analyte molecules), and thus, in these embodiments, the percentage of locations containing at least one analyte molecule is also the percentage of capture objects associated with at least one analyte molecule (e.g., the percentage "active" beads). Thus, in some embodiments, a method for determining a measure of the concentration of analyte molecules or particles in a fluid sample comprises exposing a plurality of capture objects (e.g., beads), each including a binding surface having affinity for at least one type of analyte molecule or particle (e.g., a plurality of capture components), to a solution containing or suspected of containing the at least one type of analyte molecules or particles, wherein at least some of the capture objects become associated with at least one analyte molecule or particle. At least a portion of the capture objects (e.g., beads) may be spatially segregated into a plurality of locations (e.g., reaction vessels on a surface). At least a portion of the plurality of locations (e.g., in some cases, locations containing at least one capture object) may be addressed to determine a measure indicative of the percentage of locations containing at least one analyte molecule or particle (e.g., in some cases, the percentage of capture objects associated with at least one analyte molecule). As described above, in some cases, based upon the determined percentage, a measure of the concentration of analyte molecules or particles in the fluid sample may be determined based at least in part on the number/percentage of capture objects containing at least one analyte molecule or particle and/or based at least in part on a measured intensity of a signal that is indicative of the presence of a plurality of analyte molecules or particles.

Additionally, in some cases, a system for determining a measure of the concentration of analyte molecules or particles in a fluid sample comprises an assay substrate (e.g., plate, dish, slide, chip, optical fiber face, etc.) comprising a plurality of locations (e.g., reaction vessels) each comprising a binding surface forming (e.g., a plurality of capture components) or containing such a surface (e.g., containing a bead comprising a plurality of capture components) within such locations, wherein at least one binding surface comprises at least one analyte molecule or particle immobilized on the binding surface. The system may also comprise at least one detector configured to address at least a portion of the plurality of locations and able to produce at least one signal indicative of the presence or absence of an analyte molecule or particle at each location addressed and having the ability to measure intensity levels varying with the number of analyte molecules or particles at each location. Additionally, the system may comprise at least one signal processor configured to determine from the at least one signal the number/percentage of the addressed locations containing at least one analyte molecule or particle, and further configured to, based upon the number/percentage, determine a measure of the concentration of analyte molecules or particles in the fluid sample based at least in part on the number of locations containing at least one analyte molecule or particle (digital/binary analysis), and/or determine a measure of the concentration of analyte molecules or particles in the fluid sample based at least in part on an intensity level of the at least one signal indicative of the presence of a plurality of analyte molecules or particles, using techniques described previously.

The assay methods and systems provided herein may employ a variety of different components, steps, and aspects as described herein. For example, a method may further comprise determining at least one background signal determination (e.g., and further comprising subtracting the background signal from other determinations), wash steps, and the like. In some cases, the assays or systems may include the use of at least one binding ligand, as described herein. In some cases, the measure of the concentration of analyte molecules in a fluid sample is based at least in part on comparison of a measured parameter to a calibration curve. In some instances, the calibration curve is formed at least in part by determination at least one calibration factor, as described above.

In some embodiments, the plurality of analyte molecules may be spatially segregated into a plurality of locations, wherein the locations comprise a plurality of reaction vessels. The analyte molecules may be partitioned across the plurality of reaction vessels such that at least some of the reaction vessels contain at least one analyte molecule and a statistically significant fraction of the reactions vessels contain no analyte molecules. A statistically significant fraction of reaction vessels that contain at least one analyte molecule (or no analyte molecules) will typically be able to be reproducibly detected and quantified using a particular system of detection and will typically be above the background noise (e.g., non-specific binding) that is determined when carrying out the assay with a sample that does not contain any analyte molecules, divided by the total number of locations addressed. A "statistically significant fraction" as used herein for the present embodiments, may be estimated according to the Equation 10:

$$n > 3\sqrt{n} \tag{Eq. 10}$$

wherein n is the number of determined events for a selected category of events. That is, a statistically significant fraction occurs when the number of events n is greater than three times square root of the number of events. For example, to determine a statistically significant fraction of the reaction vessels which contain an analyte molecule or particle, n is the number of reaction vessels which contain an analyte molecule. As another example, to determine a statistically significant fraction of the capture objects associated with a single analyte molecule, n is the number of capture objects associated with a single analyte molecule.

In some embodiments, the statistically significant fraction of locations that contain at least one analyte molecule (or a single analyte molecule in some cases where the ratio of locations to analyte molecules would lead, statistically, to essentially only zero or one analyte molecule contained in each location) to the total number of locations (or capture objects) is less than about 1:2, less than about 1:3, less than about 1:4, less than about 2:5, less than about 1:5, less than about 1:10, less than about 1:20, less than about 1:100, less than about 1:200, or less than about 1:500. Therefore, in such embodiments, the fraction of locations (or capture objects) not containing any analyte molecules to the total number of locations (or capture objects) is at least about 1:100, about 1:50, about 1:20, about 1:10, about 1:5, about 1:4, about 1:3, about 1:2, about 1:1, about 2:1, about 3:1, about 4:1, about 5:1, about 10:1, about 20:1, about 50:1, about 100:1, or greater.

In some embodiments, as noted previously, the percentage of locations which contain at least one analyte molecules is less than about 50%, less than about 40%, less than about 30%, less than about 20%, less than about 10%, less than about 5%, less than about 2%, less than about 1%, less than about 0.5%, less than about 0.01%, or less, the total number of locations (or capture objects). In some embodiments, the percentage of locations which do not contain (or capture object associated with) any analyte molecule is at least about 30%, at least about 40%, at least about 50%, at least about 60%, at least about 70%, at least about 80%, at least about 90%, at least about 95%, at least about 98%, or greater, the total number of locations (or capture objects).

Methods and techniques for partitioning a plurality of analyte molecules or particles into a plurality of reaction vessels is described in U.S. patent application Ser. No. 12/731,130, entitled "Ultra-Sensitive Detection of Molecules or Particles using Beads or Other Capture Objects" by Duffy et al., filed Mar. 24, 2010; International Patent Application No. (not yet determined), entitled "Ultra-Sensitive Detection of Molecules or Particles using Beads or Other Capture Objects" by Duffy et al., filed Mar. 1, 2011 (Attorney Docket No. Q0052.70011 WO00); U.S. Patent Application No. 20070259448, entitled "Methods and arrays for target analyte detection and determination of target analyte concentration in solution," by Walt et al., filed Feb. 16, 2007; U.S. Patent Application No. 20070259385, entitled "Methods and arrays for detecting cells and cellular components in small defined volumes," by Walt et al., filed Feb. 16, 2007; U.S. Patent Application No. 20070259381, entitled "Methods and arrays for target analyte detection and determination of reaction components that affect a reaction" by Walt et al., filed Feb. 16, 2007; International Patent Application No. PCT/US07/019184, entitled "Methods for Determining The Concentration of an Analyte In Solution" by Walt et al., filed Aug. 20, 2007; and International Patent Application No. PCT/US09/005,428, entitled "Ultra-Sensitive Detection of Molecules or Enzymes" by Duffy et al., filed Sep. 9, 2009, herein incorporated by reference.

In some embodiments, the assay methods may comprise the use of a plurality of capture objects. The plurality of capture objects (e.g., beads) may be configured to capture an analyte molecule or particle. In some cases, the plurality of capture objects comprises a plurality of beads. The beads may or may not be magnetic. At least a portion of the capture objects may be spatially segregated into a plurality of locations (e.g., reaction vessels/wells). The plurality of analyte molecules may be exposed to a plurality of types of binding ligands prior to, concurrent with, or following association of the plurality of analyte molecules with respect to the capture components. Various other aspects of assay methods using such capture components are described in commonly owned U.S. patent application Ser. No. 12/731,130, entitled "Ultra-Sensitive Detection of Molecules or Particles using Beads or Other Capture Objects" by Duffy et al., filed Mar. 24, 2010; and International Patent Application No. (not yet determined), entitled "Ultra-Sensitive Detection of Molecules or Particles using Beads or Other Capture Objects" by Duffy et al., filed Mar. 1, 2011 (Attorney Docket No. Q0052.70011 WO00), each, herein incorporated by reference. Specifically, the methods and systems described herein may be used in combination with and in context with the single molecules methods and systems described in the above-referenced applications. In some cases, the capture objects may be themselves detectable (e.g., fluorescence emission), and the beads may be selected such that the detection of the beads does not or does not substantially interfere with the detection of the analyte molecules.

In some embodiments, the analyte molecules may be directly detected or indirectly detected. In the case of direct detection, the analyte molecule may comprise a molecule or moiety that may be directly interrogated and/or detected (e.g., a fluorescent entity). In the case of indirect detection, an additional component is used for determining the presence of the analyte molecule. In some cases, the analyte molecules may be composed to a precursor labeling agent (e.g., enzymatic substrate) and the enzymatic substrate may be converted to a detectable product (e.g., fluorescent molecule) upon exposure to an analyte molecule. In some cases, the plurality analyte molecules may be exposed to at least one additional reaction component prior to, concurrent with, and/or following spatially separating at least some of the analyte molecules into a plurality of locations. In some cases, a plurality of capture objects at least some associated with at least one analyte molecule may be exposed to a plurality of binding ligands. In certain embodiments, a binding ligand may be adapted to be directly detected (e.g., the binding ligand comprises a detectable molecule or moiety) or may be adapted to be indirectly detected (e.g., including a component that can convert a precursor labeling agent into a labeling agent), as discussed more below. More than one type of binding may be employed in any given assay method, for example, a first type of binding ligand and a second type of binding ligand. In one example, the first type of binding ligand is able to associate with a first type of analyte molecule and the second type of binding ligand is able to associate with the first binding ligand. In another example, both a first type of binding ligand and a second type of binding ligand may associate with the same or different epitopes of a single analyte molecule, as described herein.

Certain binding ligands can comprise an entity that is able to facilitate detection, either directly or indirectly. A component may be adapted to be directly detected in embodiments where the component comprises a measurable property (e.g., a fluorescence emission, a color, etc.). A component may facilitate indirect detection, for example, by converting a precursor labeling agent into a labeling agent (e.g., an agent that is detected in an assay). A "precursor labeling agent" is any molecule, particle, or the like, that can be converted to a labeling agent upon exposure to a suitable converting agent (e.g., an enzymatic component comprise in a binding ligand). A "labeling agent" is any molecule, particle, or the like, that facilitates detection, by acting as the detected entity, using a chosen detection technique.

In some embodiments, at least one binding ligand comprises an enzymatic component. In some embodiments, the analyte molecule may comprise an enzymatic component. The enzymatic component may convert a precursor labeling agent (e.g., an enzymatic substrate) into a labeling agent (e.g., a detectable product). A measure of the concentration of analyte molecules in the fluid sample can then be determined based at least in part by determining the number of locations containing a labeling agent (e.g., by relating the number of locations containing a labeling agent to the number of locations containing an analyte molecule (or number of capture objects associated with at least one analyte molecule to total number of capture objects)). Non-limiting examples of enzymes or enzymatic components include horseradish peroxidase, beta-galactosidase, and alkaline phosphatase. Other non-limiting examples of systems or methods for detection include embodiments where nucleic acid precursors are replicated into multiple copies or converted to a nucleic acid that can be detected readily, such as the polymerase chain reaction (PCR), rolling circle amplification (RCA), ligation, Loop-Mediated Isothermal Amplification (LAMP), etc. Such systems and methods will be known to those of ordinary skill in the art, for example, as described in "DNA Amplification: Current Technologies and Applications," Vadim Demidov et al., 2004.

Figure 8:
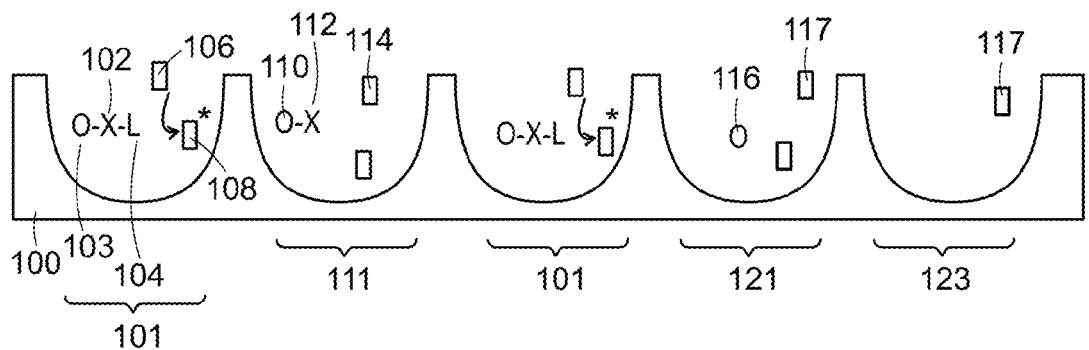
FIG. 8 is a schematic diagram depicting one embodiment of a step of a method of the invention employing a precursor labeling agent

As an example of an assay method which comprises the use of a precursor labeling agent, as shown in FIG. 8, substrate 100 comprising a plurality of locations is provided, wherein the locations comprise reaction vessels. In reaction vessel 101 (e.g., location), analyte molecule 102 is immobilized with respect to bead 103 (e.g., capture object). Binding ligand 104 is associated with analyte molecule 102. Binding ligand 104 comprises an enzymatic component (not shown). Precursor labeling agent 106 is converted to labeling agent 108 (upon exposure to the enzymatic component). Labeling agent 108 is detected using methods described herein. In contrast, reaction vessel 111 contains analyte molecule 112 immobilized with respect to bead 110. In this reaction vessel, analyte molecule 112 is not associated with a binding ligand comprising an enzymatic component. Therefore, precursor labeling agent 114 is not converted to a labeling agent in the reaction vessel. Thus this reaction vessel would give a different signal as compared to reaction vessel 101 where the precursor labeling agent was converted to a labeling agent. In some cases, there may also be reaction vessels which contain a bead not associated with an analyte molecule, for example, reaction vessel 121 contains bead 116. Additionally, some of the reaction vessels may not comprise any bead, for example, reaction vessel 123. Reaction vessels 121 and 123 may give different signals as compared to reaction vessel 101 as there would be no labeling agent present. However, reaction vessels 121 and 123 may contain precursor labeling agent 117. More than one precursor labeling agent may be present in any given reaction vessel.

In certain embodiments, solubilized, or suspended precursor labeling agents may be employed, wherein the precursor labeling agents are converted to labeling agents which are insoluble in the liquid and/or which become immobilized within/near the location (e.g., within the reaction vessel in which the labeling agent is formed). Such precursor labeling agents and labeling agents and their use is described in commonly owned U.S. patent application Ser. No. 12/236,484, filed Sep. 23, 2008, entitled "High Sensitivity Determination of the Concentration of Analyte molecules in a Fluid Sample," by Duffy et al., incorporated herein by reference.

In some embodiments, techniques may be used to prevent or reduce dissociation of an analyte molecule from a capture component and/or capture object, and/or to prevent or reduce dissociation of a binding ligand from an analyte molecule and/or another binding ligand. As will be known to those of ordinary skill in the art, some reversible affinity interactions between selected analyte molecules, capture components, and/or binding ligands (e.g., between an antibody and an antigen) are governed by thermodynamics. Accordingly, at some point during certain assay methods, some dissociation may occur between an analyte molecule and a capture component and/or a binding ligand, and/or between a binding ligand and an analyte molecule and/or another binding ligand. This may result in a reduced number of analyte molecules (e.g., immunocomplexes) being detected than are actually present. The dissociation constant of a particular pair of components (e.g., antibody-antigen pair), washing and/or fluid exposure, time between exposure and interrogation, and/or other factors, may affect the degree to which a dissociation event alters determination of analyte molecules and/or particles. Accordingly, certain techniques may be used to reduce the effects of dissociation processes.

In a first embodiment, dissociation may be reduced or eliminated by removing fluids from the assay locations (e.g., wells) following spatial segregation of a plurality of analyte molecules (e.g., associated with a capture object via a capture component and/or associated with at least one binding ligand) into a plurality of such locations. That is, all or substantially all of the fluid surrounding or substantially contained in or at the locations may be removed. For example, the fluid may be removed by air and/or vacuum drying. Removal of the fluid may reduce or eliminate dissociation. Immediately prior to interrogation of the locations, a fluid may be added to the locations thereby rehydrating the complexes to facilitate interrogation using a detector.

In a second embodiment, dissociation may be reduced or eliminated by crosslinking an analyte molecule with a capture component, and/or crosslinking a binding ligand with an analyte molecule and/or a second binding ligand. For example, an analyte molecule comprising an antigen may be crosslinked with a binding ligand and/or capture component comprising an antibody. Crosslinking methods and techniques that may be employed are known to those of ordinary skill in the art.

In some embodiments, a plurality of locations may be addressed and/or a plurality of capture objects and/or species/molecules/particles of interest may be detected substantially simultaneously. "Substantially simultaneously" when used in this context, refers to addressing/detection of the locations/capture objects/species/molecules/particles of interest at approximately the same time such that the time periods during which at least two locations/capture objects/species/molecules/particles of interest are addressed/detected overlap, as opposed to being sequentially addressed/detected, where they would not. Simultaneous addressing/detection can be accomplished by using various techniques, including optical techniques (e.g., CCD detector). Spatially segregating capture objects/species/molecules/particles into a plurality of discrete, resolvable locations, according to some embodiments facilitates substantially simultaneous detection by allowing multiple locations to be addressed substantially simultaneously. For example, for embodiments where individual species/molecules/particles are associated with capture objects that are spatially segregated with respect to the other capture objects into a plurality of discrete, separately resolvable locations during detection, substantially simultaneously addressing the plurality of discrete, separately resolvable locations permits individual capture objects, and thus individual species/molecules/particles (e.g., analyte molecules) to be resolved. For example, in certain embodiments, individual molecules/particles of a plurality of molecules/particles are partitioned across a plurality of reaction vessels such that each reaction vessel contains zero or only one species/molecule/particle. In some cases, at least about 80%, at least about 85%, at least about 90%, at least about 95%, at least about 96%, at least about 97%, at least about 98%, at least about 99%, at least about 99.5% of all species/molecules/particles are spatially separated with respect to other species/molecules/particles during detection. A plurality of species/molecules/particles may be detected substantially simultaneously within a time period of less than about 1 second, less than about 500 milliseconds, less than about 100 milliseconds, less than about 50 milliseconds, less than about 10 milliseconds, less than about 1 millisecond, less than about 500 microseconds, less than about 100 microseconds, less than about 50 microseconds, less than about 10 microseconds, less than about 1 microsecond, less than about 0.5 microseconds, less than about 0.1 microseconds, or less than about 0.01 microseconds, less than about 0.001 microseconds, or less. In some embodiments, the plurality of species/molecules/particles may be detected substantially simultaneously within a time period of between about 100 microseconds and about 0.001 microseconds, between about 10 microseconds and about 0.01 microseconds, or less.

In some embodiments, the locations are optically interrogated. The locations exhibiting changes in their optical signature may be identified by a conventional optical train and optical detection system. Depending on the detected species (e.g., type of fluorescence entity, etc.) and the operative wavelengths, optical filters designed for a particular wavelength may be employed for optical interrogation of the locations. In embodiments where optical interrogation is used, the system may comprise more than one light source and/or a plurality of filters to adjust the wavelength and/or intensity of the light source. In some embodiments, the optical signal from a plurality of locations is captured using a CCD camera.

Other non-limiting examples of camera imaging types that can be used to capture images include charge injection devices (CIDs), complimentary metal oxide semiconductors (CMOSs) devices, scientific CMOS (sCMOS) devices, and time delay integration (TDI) devices, as will be known to those of ordinary skill in the art. The camera may be obtained from a commercial source. CIDs are solid state, two dimensional multi pixel imaging devices similar to CCDS, but differ in how the image is captured and read. For examples of CCDs, see U.S. Pat. No. 3,521,244 and U.S. Pat. No. 4,016,550. CMOS devices are also two dimensional, solid state imaging devices but differ from standard CCD arrays in how the charge is collected and read out. The pixels are built into a semiconductor technology platform that manufactures CMOS transistors thus allowing a significant gain in signal from substantial readout electronics and significant correction electronics built onto the device. For example, see U.S. Pat. No. 5,883,83). sCMOS devices comprise CMOS imaging technology with certain technological improvements that allows excellent sensitivity and dynamic range. TDI devices employs a CCD device which allows columns of pixels to be shifted into and adjacent column and allowed to continue gathering light. This type of device is typically used in such a manner that the shifting of the column of pixels is synchronous with the motion of the image being gathered such that a moving image can be integrated for a significant amount of time and is not blurred by the relative motion of the image on the camera. In some embodiments, a scanning mirror system coupled with a photodiode or photomultiplier tube (PMT) could be used to for imaging.

In one embodiment, the plurality of locations is formed directly as a plurality of reaction vessels in an end of a fiber optic bundle. According to one embodiment, the array of reaction vessels for the present invention can be used in conjunction with an optical detection system such as the system described in U.S. Publication No. 20030027126. For example, according to one embodiment, the array of reaction vessels of the present invention is formed in one end of a fiber optic assembly comprising a fiber optic bundle constructed of clad fibers so that light does not mix between fibers.

Figure 9A:
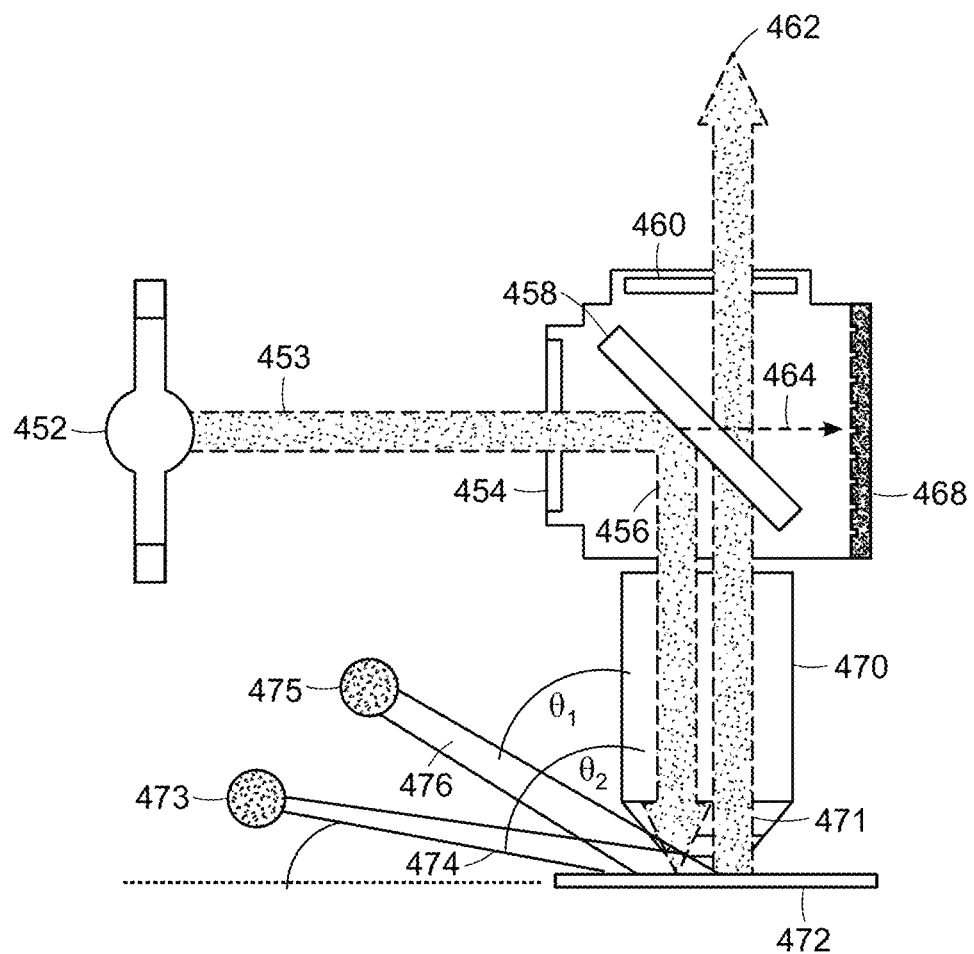
FIGS. 9A and 9B show a non-limiting example of a system employing an optical detection system.
Figure 9B:
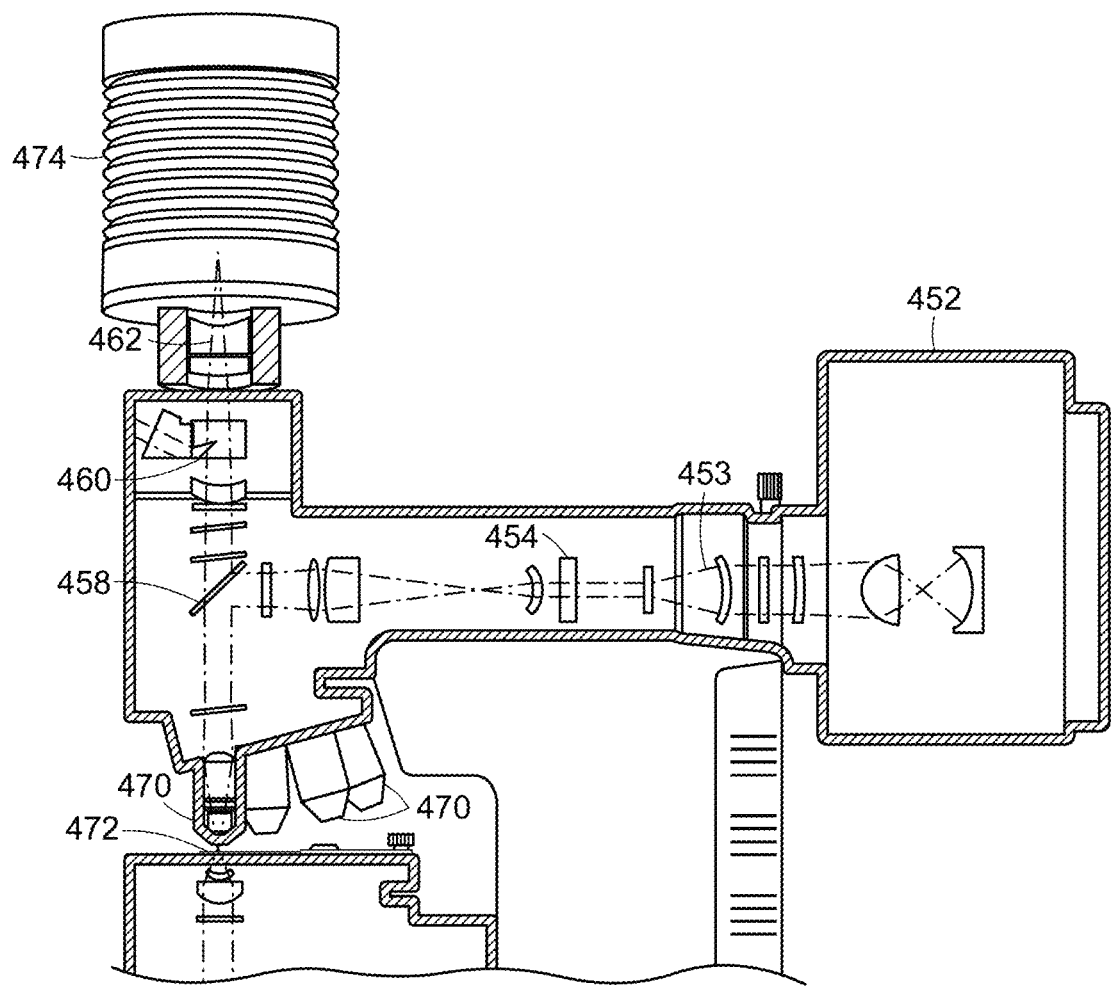

FIGS. 9A and 9B show non-limiting examples of a system of the present invention according to some embodiments. The system comprises a light source 452, excitation filter 454, dichromatic mirror 458, emission filter 460, objective 470, and array 472. Light 453 given off from light source 452 is passed through excitation filter 454. The light reflects off dichromatic mirror 458, passes through objective 470 and shines on array 472. In some cases, stray light 464 may be reduced by a stray light reducing function 468, such as an iris or aperture. Light 471 emitted from the array passes through objective 470 and emission filter 460. Light 462 is observed. The system may comprise additional components (e.g., additional filters, mirrors, magnification devices, etc.) as needed for particular applications, as would be understood by those of ordinary skill in the art.

The system shown in FIG. 9A may additionally comprise components which aid in the determination of the number of reaction vessels which contain a capture object (e.g., using white light). Alternatively, the additional components may be used to determine the total number of locations and/or provide spatially information regarding the position of the locations (e.g., containing or not containing a capture object), which may help corroborate signals observed under different light regimes (e.g., fluorescence, white light) corresponding with the position of a location (e.g., a mask may be created).

In FIGS. 9A and 9B, excitation light is emitted from source 452 and collimated into a beam 453. The excitation filter 454 may be configured to transmit only the wavelength band that excites the fluorophore (e.g., 575 nm+/−10 nm for resorufin). The excitation light is reflected downward by the dichroic filter 458 and excites the substrate 472 containing the sample through the objective lens 470. The image light is collected by the objective lens 470, collimated into a beam 471 and transmitted through the dichroic filter 458. Only the image light corresponding to the fluorescence wavelength band (e.g., 670 nm+/−30 nm for resorufin) is transmitted through the emission filter 460. The remaining collimated beam 462 contains only the emitted fluorescence wavelengths which will subsequently be imaged through the camera system.

The same system may be used to determine the positioning of the locations containing sample (e.g., reaction vessels). The array comprising the reaction vessels containing capture objects may be illuminated with a "bright field" white light illumination. The array may be illuminated (e.g., using light source 475 shown in FIG. 9A) by directing a pseudo-collimated white light (e.g., white light LED) onto the array surface from an angle (e.g., $\theta_1$ in FIG. 9A may be about 20 degrees, about 25 degrees, about 30 degrees, about 35 degrees, about 40 degrees, or greater) just outside the numerical aperture of the collection objective. Light that hits the surface of the array 472 (e.g., light 476) is reflected (and scattered) off the surface, collimated 471, and collected by the objective lens (470). The collimated beam is subsequently imaged through the camera system.

The same system may also be used to determine which locations contain a capture object (e.g., bead). Any particular bead may or may not be associated with an analyte molecule and/or binding ligand. The array may be illuminated (e.g., using light source 473 as shown in FIG. 9A) with a "dark field" white light illumination. The array may be illuminated by aiming a pseudo-collimated white light (e.g., white light LED 473) onto the array surface from an angle (e.g., $\theta_2$ in FIG. 9A is about 65 degrees, about 70 degrees, about 75 degrees, about 80 degrees, about 85 degrees) substantially outside the numerical aperture of the collection objective. Light that hits the surface of the array 472 (e.g., light 474) is reflected (and scattered) off the surface, collimated 471, and collected by the objective lens 470. The collimated beam is subsequently imaged by the camera system.

In some embodiments, an optical detection system may be employed, for example, as described in U.S. Publication No. 2003/0027126. In an exemplary system, light returning from an array of reaction vessels formed at the distal end of a fiber optic bundle is altered via use of a magnification changer to enable adjustment of the image size of the fiber's proximal or distal end. The magnified image is then shuttered and filtered by a shutter wheel. The image is then captured by charge coupled device (CCD) camera. A computer may be provided that includes and executes imaging processing software to process the information from the CCD camera and also optionally may be configured to control shutter and filter wheels. As depicted in U.S. Publication No. 20030027126, the proximal end of the bundle is received by a z-translation stage and x-y micropositioner.

Figure 10:
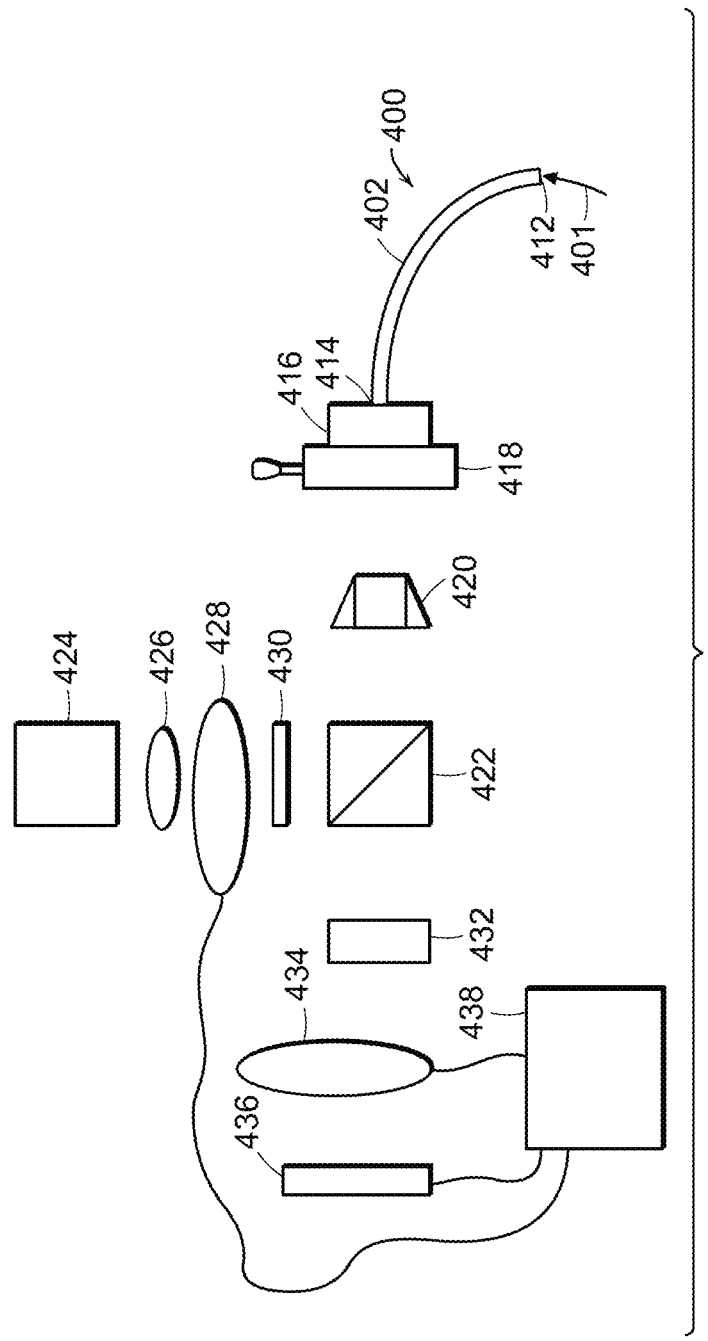
FIG. 10 is a schematic block diagram showing a system employing a fiber optic assembly with an optical detection system.

For example, FIG. 10 shows a schematic block diagram of a system employing a fiber optic assembly 400 with an optical detection system. The fiber optic assembly 400 that comprises a fiber optic bundle or array 402 that is constructed from clad fibers so that light does not mix between fibers. An array of reaction vessels 401 is formed at/attached to the bundle's distal end 412, with the proximal end 414 being operatively connected with a z-translation stage 416 and x-y micropositioner 418. These two components act in concert to properly position the proximal end 414 of the bundle 402 for a microscope objective lens 420. Light collected by the objective lens 420 is passed to a reflected light fluorescence attachment with three pointer cube slider 422. The attachment 422 allows directs light from a 75 watt Xe lamp 424 through the objective lens 420 to be coupled into the fiber bundle 402. The light from source 424 is condensed by condensing lens 426, then filtered and/or shuttered by filter and shutter wheel 428, and subsequently passes through a ND filter slide 430. Light returning from the distal end 412 of the bundle 402 passes through the attachment 422 to a magnification changer 432 which enables adjustment of the image size of the fiber's proximal or distal end. Light passing through the magnification changer 432 is then shuttered and filtered by a second wheel 434. The light is collected by a charge coupled device (CCD) camera 436. A computer 438 executes imaging processing software to process the information from the CCD camera 436 and also optionally controls other components of the system, including but not limited to the first and second shutter and filter wheels 428, 434. An array of reaction vessels used to practice some embodiments of the present invention may be integral with or attached to the distal end of the fiber optic bundle using a variety of compatible processes. In some cases, microwells are formed at the center of each individual fiber of the fiber optic bundle and the microwells may or may not be sealed. Each optical fiber of the fiber optic bundle may convey light from the single microwell formed at the center of the fiber's distal end. This feature enables the interrogation of the optical signature of individual reaction vessels to identify reactions/contents in each microwell. Consequently, by collecting the image of the end of the bundle with the CCD array, the optical signatures of the reaction vessels may be individually interrogated and/or imaged substantially simultaneously.

The plurality of locations may be formed using any suitable technique. In some embodiments, the plurality of locations comprises a plurality of reaction vessels/wells on a substrate. The reactions vessels, in certain embodiments, may be configured to receive and contain only a single capture object.

In some embodiments of the present invention, the plurality of reaction vessels may be sealed (e.g., after the introduction of the analyte molecules, binding ligands, and/or precursor labeling agent), for example, through the mating of the second substrate and a sealing component. The sealing of the reaction vessels may be such that the contents of each reaction vessel cannot escape the reaction vessel during the remainder of the assay. In some cases, the reaction vessels may be sealed after the addition of the analyte molecules and, optionally, at least one type of precursor labeling agent to facilitate detection of the analyte molecules. For embodiments employing precursor labeling agents, by sealing the contents in some or each reaction vessel, a reaction to produce the detectable labeling agents can proceed within the sealed reaction vessels, thereby producing a detectable amount of labeling agents that is retained in the reaction vessel for detection purposes.

The plurality of locations comprising a plurality of reaction vessels may be formed using a variety of methods and/or materials. In some cases, the plurality of reaction vessels is formed as an array of depressions on a first surface. In other cases, however, the plurality of reaction vessels may be formed by mating a sealing component comprising a plurality of depressions with a substrate that may either have a featureless surface or include depressions aligned with those on the sealing component. Any of the device components, for example, the substrate or sealing component, may be fabricated from a compliant material, e.g., an elastomeric polymer material, to aid in sealing. The surfaces may be or made to be hydrophobic or contain hydrophobic regions to minimize leakage of aqueous samples from the microwells.

In some cases, the sealing component may be capable of contacting the exterior surface of an array of microwells (e.g., the cladding of a fiber optic bundle as described in more detail below) such that each reaction vessel becomes sealed or isolated such that the contents of each reaction vessel cannot escape the reaction vessel. According to one embodiment, the sealing component may be a silicone elastomer gasket that may be placed against an array of microwells with application of substantially uniform pressure across the entire substrate. In some cases, the reaction vessels may be sealed after the addition of the plurality of capture objects used for analyte capture and, optionally, any precursor labeling agent molecule that may be used to facilitate detection of the analyte molecule.

Figure 11:
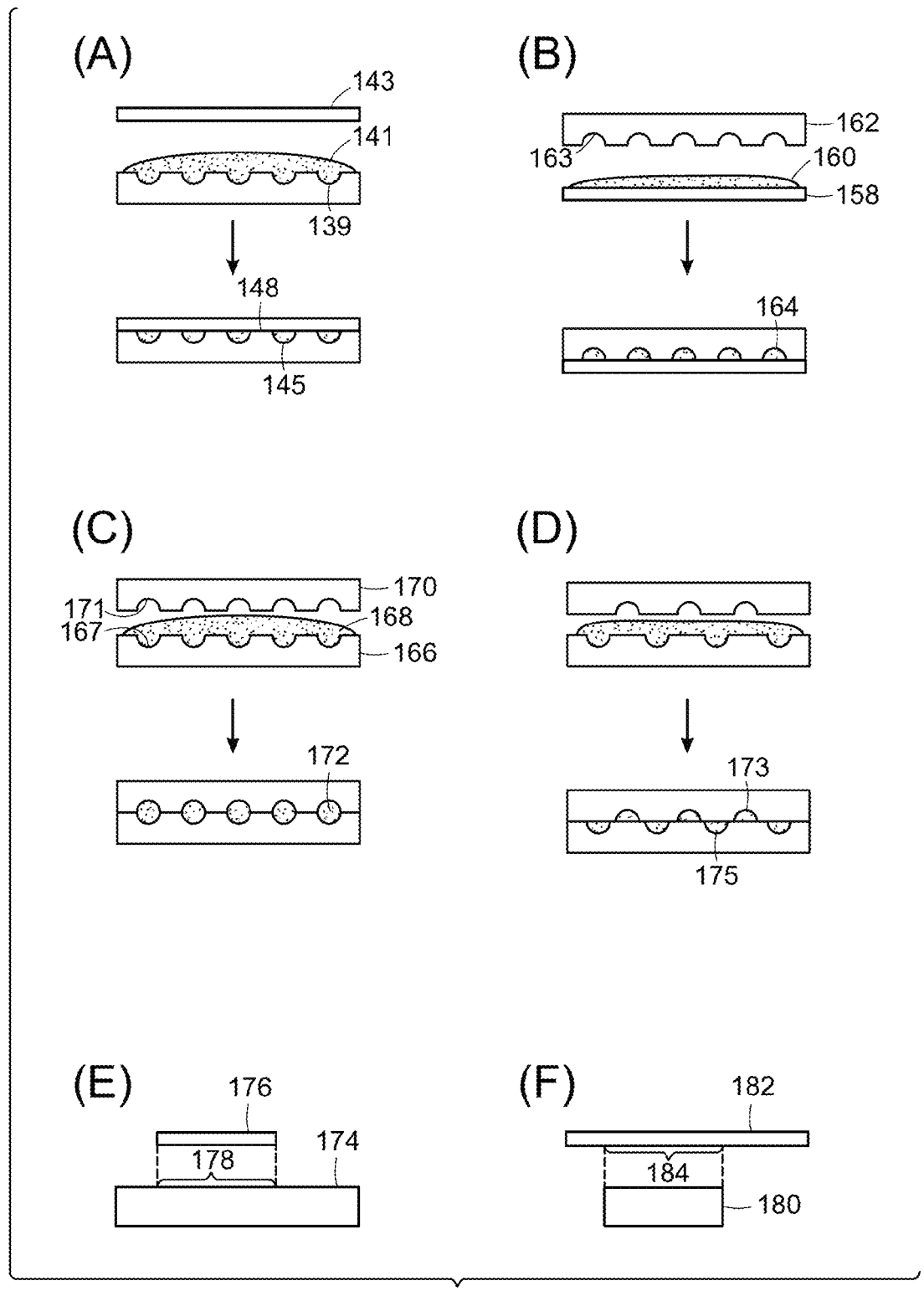
FIG. 11 is a schematic flow diagram depicting an embodiment of a method (steps A-D) for the formation of a plurality of reaction vessels through mating of a substrate and a sealing component and depicting examples of the size (E, F) of a sealing component relative to a substrate.

A non-limiting example of the formation of a plurality of reaction vessels containing assay solution on/in a substrate is depicted in FIG. 11. FIG. 11, panel (A) shows a surface comprising a plurality of microwells 139, which have been exposed to an assay solution 141 (e.g., a solution containing the analyte molecules), and a sealing component 143. Sealing component 143 in this example comprises a substantially planar bottom surface. Mating of substrate 139 with sealing component 143 forms a plurality of sealed reaction vessels 145. The areas between the reaction vessels 148 may be modified to aid in the formation of a tight seal between the reaction vessels.

A second embodiment is shown in FIG. 11, panel (B), in which sealing component 162 comprising a plurality of microwells 163 is mated with a substantially planar surface 158 which has been exposed to assay solution 162, thereby forming a plurality of reaction vessels 164.

In a third embodiment, as shown in FIG. 11, panel (C), substrate surface 166 comprising a plurality of microwells 167 is mated with sealing component 170 also comprising a plurality of microwells 171. In this embodiment, the microwells in the substrate and the microwells in the sealing components are substantially aligned so each reaction vessel 172 formed comprises a portion of the microwell from the sealing component and a portion of a microwell from the substrate. In FIG. 11, panel (D), the microwells are not aligned such that each reaction vessel comprises either a microwell from the sealing component 173 or a microwell from the substrate 175.

The sealing component may be essentially the same size as the substrate or may be different in size. In some cases, the sealing component is approximately the same size as the substrate and mates with substantially the entire surface of the substrate. In other cases, as depicted in FIG. 11, panel (E), the sealing component 176 is smaller than the substrate 174 and the sealing component only mates with a portion 178 of the substrate. In yet another embodiment, as depicted in FIG. 11, panel (F), the sealing component 182 is larger than the substrate 180, and only a portion 184 of the sealing component mates with the substrate 180.

In some embodiments, the reaction vessels may all have approximately the same volume. In other embodiments, the reaction vessels may have differing volumes. The volume of each individual reaction vessel may be selected to be appropriate to facilitate any particular assay protocol. For example, in one set of embodiments where it is desirable to limit the number of capture objects used for analyte capture contained in each vessel to a small number, the volume of the reaction vessels may range from attoliters or smaller to nanoliters or larger depending upon the nature of the capture objects, the detection technique and equipment employed, the number and density of the wells on the substrate and the expected concentration of capture objects in the fluid applied to the substrate containing the wells. In one embodiment, the size of the reaction vessel may be selected such only a single capture object used for analyte capture can be fully contained within the reaction vessel (see, for example, U.S. patent application Ser. No. 12/731,130, entitled "Ultra-Sensitive Detection of Molecules or Particles using Beads or Other Capture Objects" by Duffy, et al., filed Mar. 24, 2010; or International Patent Application No. (not yet determined), entitled "Ultra-Sensitive Detection of Molecules or Particles using Beads or Other Capture Objects" by Duffy, et al., filed Mar. 1, 2011, (Attorney Docket No. Q0052.70011 WO00)), herein incorporated by reference).

In accordance with one embodiment of the present invention, the reaction vessels may have a volume between about 1 femtoliter and about 1 picoliter, between about 1 femtoliters and about 100 femtoliters, between about 10 attoliters and about 100 picoliters, between about 1 picoliter and about 100 picoliters, between about 1 femtoliter and about 1 picoliter, or between about 30 femtoliters and about 60 femtoliters. In some cases, the reaction vessels have a volume of less than about 1 picoliter, less than about 500 femtoliters, less than about 100 femtoliters, less than about 50 femtoliters, or less than about 1 femtoliter. In some cases, the reaction vessels have a volume of about 10 femtoliters, about 20 femtoliters, about 30 femtoliters, about 40 femtoliters, about 50 femtoliters, about 60 femtoliters, about 70 femtoliters, about 80 femtoliters, about 90 femtoliters, or about 100 femtoliters.

The total number of locations and/or density of the locations employed in an assay (e.g., the number/density of reaction vessels in an array) can depend on the composition and end use of the array. For example, the number of reaction vessels employed may depend on the number of types of analyte molecule and/or binding ligand employed, the suspected concentration range of the assay, the method of detection, the size of the capture objects, the type of detection entity (e.g., free labeling agent in solution, precipitating labeling agent, etc.). Arrays containing from about 2 to many billions of reaction vessels (or total number of reaction vessels) can be made by utilizing a variety of techniques and materials. Increasing the number of reaction vessels in the array can be used to increase the dynamic range of an assay or to allow multiple samples or multiple types of analyte molecules to be assayed in parallel. The array may comprise between one thousand and one million reaction vessels per sample to be analyzed. In some cases, the array comprises greater than one million reaction vessels. In some embodiments, the array comprises between about 1,000 and about 50,000, between about 1,000 and about 1,000,000, between about 1,000 and about 10,000, between about 10,000 and about 100,000, between about 100,000 and about 1,000,000, between about 100,000 and about 500,000, between about 1,000 and about 100,000, between about 50,000 and about 100,000, between about 20,000 and about 80,000, between about 30,000 and about 70,000, between about 40,000 and about 60,000 reaction vessels. In some embodiments, the array comprises about 10,000, about 20,000, about 50,000, about 100,000, about 150,000, about 200,000, about 300,000, about 500,000, about 1,000,000, or more, reaction vessels.

The array of reaction vessels may be arranged on a substantially planar surface or in a non-planar three-dimensional arrangement. The reaction vessels may be arrayed in a regular pattern or may be randomly distributed. In a specific embodiment, the array is a regular pattern of sites on a substantially planar surface permitting the sites to be addressed in the X-Y coordinate plane.

In some embodiments, the reaction vessels are formed in a solid material. As will be appreciated by those in the art, the number of potentially suitable materials in which the reaction vessels can be formed is very large, and includes, but is not limited to, glass (including modified and/or functionalized glass), plastics (including acrylics, polystyrene and copolymers of styrene and other materials, polypropylene, polyethylene, polybutylene, polyurethanes, cyclic olefin copolymer (COC), cyclic olefin polymer (COP), Teflon®, polysaccharides, nylon or nitrocellulose, etc.), elastomers (such as poly (dimethyl siloxane) and poly urethanes), composite materials, ceramics, silica or silica-based materials (including silicon and modified silicon), carbon, metals, optical fiber bundles, or the like. In general, the substrate material may be selected to allow for optical detection without appreciable autofluorescence. In certain embodiments, the reaction vessels may be formed in a flexible material.

A reaction vessel in a surface (e.g., substrate or sealing component) may be formed using a variety of techniques known in the art, including, but not limited to, photolithography, stamping techniques, molding techniques, etching techniques, or the like. As will be appreciated by those of the ordinary skill in the art, the technique used can depend on the composition and shape of the supporting material and the size and number of reaction vessels.

In a particular embodiment, an array of reaction vessels is formed by creating microwells on one end of a fiber optic bundle and utilizing a planar compliant surface as a sealing component. In certain such embodiments, an array of reaction vessels in the end of a fiber optic bundle may be formed as follows. First, an array of microwells is etched into the end of a polished fiber optic bundle. Techniques and materials for forming and etching a fiber optic bundle are known to those of ordinary skill in the art. For example, the diameter of the optical fibers, the presence, size and composition of core and cladding regions of the fiber, and the depth and specificity of the etch may be varied by the etching technique chosen so that microwells of the desired volume may be formed. In certain embodiments, the etching process creates microwells by preferentially etching the core material of the individual glass fibers in the bundle such that each well is approximately aligned with a single fiber and isolated from adjacent wells by the cladding material. Potential advantages of the fiber optic array format is that it can produce thousands to millions of reaction vessels without complicated microfabrication procedures and that it can provide the ability to observe and optically address many reaction vessels simultaneously.

Each microwell may be aligned with an optical fiber in the bundle so that the fiber optic bundle can carry both excitation and emission light to and from the wells, enabling remote interrogation of the well contents. Further, an array of optical fibers may provide the capability for simultaneous or non-simultaneous excitation of molecules in adjacent vessels, without signal "cross-talk" between fibers. That is, excitation light transmitted in one fiber does not escape to a neighboring fiber.

Alternatively, the equivalent structures of a plurality of reaction vessels may be fabricated using other methods and materials that do not utilize the ends of an optical fiber bundle as a substrate. For example, the array may be a spotted, printed or photolithographically fabricated substrate produced by techniques known in the art; see for example WO95/25116; WO95/35505; PCT US98/09163; U.S. Pat. Nos. 5,700,637, 5,807,522, 5,445,934, 6,406,845, and 6,482,593. In some cases, the array may be produced using molding, embossing, and/or etching techniques as will be known to those of ordinary skill in the art.

In certain embodiments, the present invention provides a system equipped with a mechanical platform that applies a sealing component to a substrate. The platform may be positioned beneath a stage on the system. After the chosen reaction components have been added to an array of reaction vessels, the sealing component may be mated with the array. For example, the sealing component may be sandwiched between a flat surface (such as, for example, a microscope slide) and the array of reaction vessels using uniform pressure applied by the mechanical platform.

A non-limiting embodiment is illustrated in FIG. 12A. A sealing component 300 is placed on top of mechanical platform 302. The assay solution 304 is placed on top of the sealing component 300. The mechanical platform is moved upwards towards the array 306 (e.g., fiber optic array) such that uniform pressure is applied. As shown in FIG. 12B, the sealing component 300 forms a tight seal with the array 306. In other instances, varying pressure may be applied to the sealing component to form a tight seal between the sealing component and the array. The system may also comprise additional components 312 that may be utilized to analyze the array (e.g., microscope, computer, etc.) as discussed more herein.

In some embodiments, the plurality of locations may not comprise a plurality of reaction vessels/wells. For example, in embodiments where capture objects are employed, a patterned substantially planar surface may be employed and the patterned areas form a plurality of locations. In some cases, the patterned areas may comprise substantially hydrophilic surfaces which are substantially surrounded by substantially hydrophobic surfaces. In certain embodiments, a plurality of capture objects (e.g., beads) may be substantially surrounded by a substantially hydrophilic medium (e.g., comprising water), and the beads may be exposed to the patterned surface such that the beads associate in the patterned areas (e.g., the hydrophilic locations on the surface), thereby spatially segregating the plurality of beads. For example, in one such embodiment, a substrate may be or include a gel or other material able to provide a sufficient barrier to mass transport (e.g., convective and/or diffusional barrier) to prevent capture objects used for analyte capture and/or precursor labeling agent and/or labeling agent from moving from one location on or in the material to another location so as to cause interference or cross-talk between spatial locations containing different capture objects during the time frame required to address the locations and complete the assay. For example, in one embodiment, a plurality of capture objects is spatially separated by dispersing the capture objects on and/or in a hydrogel material. In some cases, a precursor labeling agent may be already present in the hydrogel, thereby facilitating development of a local concentration of the labeling agent (e.g., upon exposure to a binding ligand or analyte molecule carrying an enzymatic component). As still yet another embodiment, the capture objects may be confined in one or more capillaries. In some cases, the plurality of capture objects may be absorbed or localized on a porous or fibrous substrate, for example, filter paper. In some embodiments, the capture objects may be spatially segregated on a uniform surface (e.g., a planar surface), and the capture objects may be detected using precursor labeling agents which are converted to substantially insoluble or precipitating labeling agents that remain localized at or near the location of where the corresponding capture object is localized. The use of such substantially insoluble or precipitating labeling agents is described herein. In some cases, single analyte molecules may be spatially segregated into a plurality of droplets. That is, single analyte molecules may be substantially contained in a droplet containing a first fluid. The droplet may be substantially surrounded by a second fluid, wherein the second fluid is substantially immiscible with the first fluid.

In some embodiments, during the assay, at least one washing step may be carried out. In certain embodiments, the wash solution is selected so that it does not cause appreciable change to the configuration of the capture objects and/or analyte molecules and/or does not disrupt any specific binding interaction between at least two components of the assay (e.g., a capture component and an analyte molecule). In other cases, the wash solution may be a solution that is selected to chemically interact with one or more assay components. As will be understood by those of ordinary skill in the art, a wash step may be performed at any appropriate time point during the inventive methods. For example, a plurality of capture objects may be washed after exposing the capture objects to one or more solutions comprising analyte molecules, binding ligands, precursor labeling agents, or the like. As another example, following immobilization of the analyte molecules with respect to a plurality of capture objects, the plurality of capture objects may be subjected to a washing step thereby removing any analyte molecules not specifically immobilized with respect to a capture object.

Analyzer Systems

The invention also involves a system for determining a measure of the concentration of analyte molecules or particles in a fluid sample configured to perform at least some of the assay steps and/or signal/data processing steps described above.

For example in certain embodiments, the invention involves a system for determining a measure of the concentration of analyte molecules or particles in a fluid sample, comprising an assay substrate comprising a plurality of locations each comprising a binding surface forming or contained within such locations, wherein at least one binding surface comprises at least one analyte molecule or particle immobilized on the binding surface, at least one detector configured to address a plurality of the locations and able to produce at least one signal indicative of the presence or absence of an analyte molecule or particle at each location addressed and having an intensity varying with the number of analyte molecules or particles at each location, and at least one signal processor configured to determine from the at least one signal the percentage of the locations containing at least one analyte molecule or particle, and further configured to, based upon the percentage, either determine a measure of the concentration of analyte molecules or particles in the fluid sample based at least in part on the number of locations containing at least one analyte molecule or particle, or determine a measure of the concentration of analyte molecules or particles in the fluid sample based at least in part on an intensity level of the at least one signal indicative of the presence of a plurality of analyte molecules or particles:

In certain such embodiments, the signal processor may comprise or be a part of the computer 438 illustrated in FIG. 10. The signal processor/computer can be part of or coupled in operative association with the remaining components of the system, and, in some embodiments, configured and/or programmed to control and adjust operational parameters of the system as well as analyze and calculate values, as described above. In some embodiments, the signal processor/ computer can send and receive control signals to set and/or control operating parameters of the other components of the system. In other embodiments, the signal processor/computer can be separate from and/or remotely located with respect to other system components and may be configured to receive data from one or more other components of the system via indirect and/or portable means, such as via portable electronic data storage devices, such as magnetic disks, or via communication over a computer network, such as the Internet or a local intranet.

The signal processor/computer may include several known components and circuitry, including a processing unit (i.e., processor), a memory system, input and output devices and interfaces (e.g., an interconnection mechanism), as well as other components, such as transport circuitry (e.g., one or more busses), a video and audio data input/output (I/O) subsystem, special-purpose hardware, as well as other components and circuitry, as described below in more detail. Further, the signal processor/computer may be a multi-processor computer system or may include multiple computers connected over a computer network.

The signal processor/computer may include a processor, for example, a commercially available processor such as one of the series x86, Celeron and Pentium processors, available from Intel, similar devices from AMD and Cyrix, the 680×0 series microprocessors available from Motorola, and the PowerPC microprocessor from IBM. Many other processors are available, and the computer system is not limited to a particular processor.

A processor typically executes a program called an operating system, of which Windows 7, Windows Vista, WindowsNT, Windows95 or 98, UNIX, Linux, DOS, VMS, MacOS and OS8 are examples, which controls the execution of other computer programs and provides scheduling, debugging, input/output control, accounting, compilation, storage assignment, data management and memory management, communication control and related services. The processor and operating system together define a computer platform for which application programs in high-level programming languages are written. The signal processor/computer is not limited to a particular computer platform.

The signal processor/computer may include a memory system, which typically includes a computer readable and writeable non-volatile recording medium, of which a magnetic disk, optical disk, a flash memory and tape are examples. Such a recording medium may be removable, for example, a floppy disk, read/write CD or memory stick, or may be permanent, for example, a hard drive.

Such a recording medium stores signals, typically in binary form (i.e., a form interpreted as a sequence of one and zeros). A disk (e.g., magnetic or optical) has a number of tracks, on which such signals may be stored, typically in binary form, i.e., a form interpreted as a sequence of ones and zeros. Such signals may define a software program, e.g., an application program, to be executed by the microprocessor, or information to be processed by the application program.

The memory system of the signal processor/computer also may include an integrated circuit memory element, which typically is a volatile, random access memory such as a dynamic random access memory (DRAM) or static memory (SRAM). Typically, in operation, the processor causes programs and data to be read from the non-volatile recording medium into the integrated circuit memory element, which typically allows for faster access to the program instructions and data by the processor than does the non-volatile recording medium.

The processor generally manipulates the data within the integrated circuit memory element in accordance with the program instructions and then copies the manipulated data to the non-volatile recording medium after processing is completed. A variety of mechanisms are known for managing data movement between the non-volatile recording medium and the integrated circuit memory element, and the signal processor/computer that implements the methods, steps, systems and system elements described above is not limited thereto. The signal processor/computer is not limited to a particular memory system.

At least part of such a memory system described above may be used to store one or more data structures (e.g., look-up tables) or equations described above. For example, at least part of the non-volatile recording medium may store at least part of a database that includes one or more of such data structures. Such a database may be any of a variety of types of databases, for example, a file system including one or more flat-file data structures where data is organized into data units separated by delimiters, a relational database where data is organized into data units stored in tables, an object-oriented database where data is organized into data units stored as objects, another type of database, or any combination thereof.

The signal processor/computer may include a video and audio data I/O subsystem. An audio portion of the subsystem may include an analog-to-digital (A/D) converter, which receives analog audio information and converts it to digital information. The digital information may be compressed using known compression systems for storage on the hard disk to use at another time. A typical video portion of the I/O subsystem may include a video image compressor/decompressor of which many are known in the art. Such compressor/decompressors convert analog video information into compressed digital information, and vice-versa. The compressed digital information may be stored on hard disk for use at a later time.

The signal processor/computer may include one or more output devices. Example output devices include a cathode ray tube (CRT), liquid crystal displays (LCD) and other video output devices, printers, communication devices such as a modem or network interface, storage devices such as disk or tape, and audio output devices such as a speaker.

The signal processor/computer also may include one or more input devices. Example input devices include a keyboard, keypad, track ball, mouse, pen and tablet, communication devices such as described above, and data input devices such as audio and video capture devices and sensors. The signal processor/computer is not limited to the particular input or output devices described herein.

The signal processor/computer may include specially programmed, special purpose hardware, for example, an application-specific integrated circuit (ASIC). Such special-purpose hardware may be configured to implement one or more of the methods, steps, simulations, algorithms, systems, and system elements described above. The signal processor/computer and components thereof may be programmable using any of a variety of one or more suitable computer programming languages. Such languages may include procedural programming languages, for example, C, Pascal, Fortran and BASIC, object-oriented languages, for example, C++, Java and Eiffel and other languages, such as a scripting language or even assembly language.

The methods, steps, simulations, algorithms, systems, and system elements may be implemented using any of a variety of suitable programming languages, including procedural programming languages, object-oriented programming languages, other languages and combinations thereof, which may be executed by such a computer system. Such methods, steps, simulations, algorithms, systems, and system elements can be implemented as separate modules of a computer program, or can be implemented individually as separate computer programs. Such modules and programs can be executed on separate computers.

The methods, steps, simulations, algorithms, systems, and system elements described above may be implemented in software, hardware or firmware, or any combination of the three, as part of the computer implemented control system described above or as an independent component.

Such methods, steps, simulations, algorithms, systems, and system elements, either individually or in combination, may be implemented as a computer program product tangibly embodied as computer-readable signals on a computer-readable medium, for example, a non-volatile recording medium, an integrated circuit memory element, or a combination thereof. For each such method, step, simulation, algorithm, system, or system element, such a computer program product may comprise computer-readable signals tangibly embodied on the computer-readable medium that define instructions, for example, as part of one or more programs, that, as a result of being executed by a computer, instruct the computer to perform the method, step, simulation, algorithm, system, or system element.

Exemplary Target Analytes

As will be appreciated by those in the art, a large number of analyte molecules and particles may be detected and, optionally, quantified using methods and systems of the present invention; basically, any analyte molecule that is able to be made to become immobilized with respect to a binding ligand can be potentially investigated using the invention. Certain more specific targets of potential interest that may comprise an analyte molecule are mentioned below. The list below is exemplary and non-limiting.

In some embodiments, the analyte molecule may be a biomolecule. Non-limiting examples of biomolecules include hormones, antibodies, cytokines, proteins, nucleic acids, lipids, carbohydrates, lipids cellular membrane antigens and receptors (neural, hormonal, nutrient, and cell surface receptors) or their ligands, or combinations thereof. Non-limiting embodiments of proteins include peptides, polypeptides, protein fragments, protein complexes, fusion proteins, recombinant proteins, phosphoproteins, glycoproteins, lipoproteins, or the like. As will be appreciated by those in the art, there are a large number of possible proteinaceous analyte molecules that may be detected or evaluated for binding partners using the present invention. In addition to enzymes as discussed above, suitable protein analyte molecules include, but are not limited to, immunoglobulins, hormones, growth factors, cytokines (many of which serve as ligands for cellular receptors), cancer markers, etc. Non-limiting examples of biomolecules include PSA and TNF-alpha.

In certain embodiments, the analyte molecule may be a host-translationally modified protein (e.g., phosphorylation, methylation, glycosylation) and the capture component may be an antibody specific to a post-translational modification. Modified proteins may be captured with capture components comprising a multiplicity of specific antibodies and then the captured proteins may be further bound to a binding ligand comprising a secondary antibody with specificity to a post-translational modification. Alternatively, modified proteins may be captured with capture components comprising an antibody specific for a post-translational modification and then the captured proteins may be further bound to binding ligands comprising antibodies specific to each modified protein.

In another embodiment, the analyte molecule is a nucleic acid. A nucleic acid may be captured with a complementary nucleic acid fragment (e.g., an oligonucleotide) and then optionally subsequently labeled with a binding ligand comprising a different complementary oligonucleotide.

Suitable analyte molecules and particles include, but are not limited to small molecules (including organic compounds and inorganic compounds), environmental pollutants (including pesticides, insecticides, toxins, etc.), therapeutic molecules (including therapeutic and abused drugs, antibiotics, etc.), biomolecules (including hormones, cytokines, proteins, nucleic acids, lipids, carbohydrates, cellular membrane antigens and receptors (neural, hormonal, nutrient, and cell surface receptors) or their ligands, etc), whole cells (including prokaryotic (such as pathogenic bacteria) and eukaryotic cells, including mammalian tumor cells), viruses (including retroviruses, herpesviruses, adenoviruses, lentiviruses, etc.), spores, etc.

In some embodiments, the analyte molecule may be an enzyme. Non-limiting examples of enzymes include, an oxidoreductase, transferase, kinase, hydrolase, lyase, isomerase, ligase, and the like. Additional examples of enzymes include, but are not limited to, polymerases, cathepsins, calpains, amino-transferases such as, for example, AST and ALT, proteases such as, for example, caspases, nucleotide cyclases, transferases, lipases, enzymes associated with heart attacks, and the like. When a system/method of the present invention is used to detect the presence of viral or bacterial agents, appropriate target enzymes include viral or bacterial polymerases and other such enzymes, including viral or bacterial proteases, or the like.

In other embodiments, the analyte molecule may comprise an enzymatic component. For example, the analyte particle can be a cell having an enzyme or enzymatic component present on its extracellular surface. Alternatively, the analyte particle is a cell having no enzymatic component on its surface. Such a cell is typically identified using an indirect assaying method described below. Non-limiting example of enzymatic components are horseradish peroxidase, beta-galactosidase, and alkaline phosphatase.

The fluid sample containing or suspected of containing an analyte molecule may be derived from any suitable source. In some cases, the sample may comprise a liquid, fluent particulate solid, fluid suspension of solid particles, supercritical fluid, and/or gas. In some cases, the analyte molecule may be separated or purified from its source prior to determination; however, in certain embodiments, an untreated sample containing the analyte molecule may be tested directly. The source of the analyte molecule may be synthetic (e.g., produced in a laboratory), the environment (e.g., air, soil, etc.), a mammal, an animal, a plant, or any combination thereof. In a particular example, the source of an analyte molecule is a human bodily substance (e.g., blood, serum, plasma, urine, saliva, tissue, organ, or the like). The volume of the fluid sample analyzed may potentially be any amount within a wide range of volumes, depending on a number of factors such as, for example, the number of capture objects used/available, the number of locations us/available, etc. In a few particular exemplary embodiments, the sample volume may be about 0.01 ul, about 0.1 uL, about 1 uL, about 5 uL, about 10 uL, about 100 uL, about 1 mL, about 5 mL, about 10 mL, or the like. In some cases, the volume of the fluid sample is between about 0.01 uL and about 10 mL, between about 0.01 uL and about 1 mL, between about 0.01 uL and about 100 uL, or between about 0.1 uL and about 10 uL.

In some cases, the fluid sample may be diluted prior to use in an assay. For example, in embodiments where the source of an analyte molecule is a human body fluid (e.g., blood, serum), the fluid may be diluted with an appropriate solvent (e.g., a buffer such as PBS buffer). A fluid sample may be diluted about 1-fold, about 2-fold, about 3-fold, about 4-fold, about 5-fold, about 6-fold, about 10-fold, or greater, prior to use. The sample may be added to a solution comprising the plurality of capture objects, or the plurality of capture objects may be added directly to or as a solution to the sample.

Capture Components

In some embodiments of the present invention, the analyte molecules may be immobilized with respect to a surface (e.g., the surface of a capture object, the surface of a location (e.g., reaction vessel), or the like). The analyte molecules may be immobilized with respect to a surface prior to, concurrent with, or following exposure to a plurality of types of binding ligands. In some embodiments, immobilization of the analyte molecules with respect to a surface may aid in removal of any excess binding ligands from the solution without concern of dislodging the analyte molecule from the surface (e.g., from the reaction vessel). Generally, a capture component allows the attachment of a molecule, particle, or complex to a solid support (e.g., capture object, location, etc.) for the purposes of immobilization, detection, quantification, and/or other analysis of the molecule, particle, or complex.

As will be appreciated by those in the art, the composition of the capture component will depend on the composition of the analyte molecule. Capture components for a wide variety of target molecules are known or can be readily found or developed using known techniques. For example, when the target molecule is a protein, the capture components may comprise proteins, particularly antibodies or fragments thereof (e.g., antigen-binding fragments (Fabs), Fab' fragments, pepsin fragments, F(ab')$_2$ fragments, full-length polyclonal or monoclonal antibodies, antibody-like fragments, etc.), other proteins, such as receptor proteins, Protein A, Protein C, etc., or small molecules. In some cases, capture components for proteins comprise peptides. For example, when the target molecule is an enzyme, suitable capture components may include enzyme substrates and/or enzyme inhibitors. In some cases, when the target analyte is a phosphorylated species, the capture component may comprise a phosphate-binding agent. For example, the phosphate-binding agent may comprise metal-ion affinity media such as those describe in U.S. Pat. No. 7,070,921 and U.S. Patent Application No. 20060121544. In addition, when the target molecule is a single-stranded nucleic acid, the capture component may be a complementary nucleic acid. Similarly, the target molecule may be a nucleic acid binding protein and the capture component may be a single-stranded or double-stranded nucleic acid; alternatively, the capture component may be a nucleic acid-binding protein when the target molecule is a single or double stranded nucleic acid. Alternatively, as is generally described in U.S. Pat. Nos. 5,270,163, 5,475,096, 5,567,588, 5,595,877, 5,637,459, 5,683,867, 5,705,337, and related patents, nucleic acid "aptamers" may be developed for capturing virtually any target molecule. Also, for example, when the target molecule is a carbohydrate, potentially suitable capture components include, for example, antibodies, lectins, and selectins. As will be appreciated by those of ordinary skill in the art, any molecule that can specifically associate with a target molecule of interest may potentially be used as a capture component.

For certain embodiments, suitable target analyte molecule/capture component pairs can include, but are not limited to, antibodies/antigens, receptors/ligands, proteins/nucleic acid, nucleic acids/nucleic acids, enzymes/substrates and/or inhibitors, carbohydrates (including glycoproteins and glycolipids)/lectins and/or selectins, proteins/proteins, proteins/small molecules; small molecules/small molecules, etc. According to one embodiment, the capture components are portions (particularly the extracellular portions) of cell surface receptors that are known to multimerize, such as the growth hormone receptor, glucose transporters (particularly GLUT 4 receptor), and T-cell receptors and the target analytes are one or more receptor target ligands.

In a particular embodiment, the capture component may be attached to the surface via a linkage, which may comprise any moiety, functionalization, or modification of the binding surface and/or capture component that facilitates the attachment of the capture component to the surface. The linkage between the capture component and the surface may comprise one or more chemical or physical (e.g., non-specific attachment via van der Waals forces, hydrogen bonding, electrostatic interactions, hydrophobic/hydrophilic interactions; etc.) bonds and/or chemical linkers providing such bond(s). In certain embodiments, the capture component comprises a capture extender component. In such embodiments, the capture component comprises a first portion that binds the analyte molecule and a second portion that can be used for attachment to the binding surface.

In certain embodiments, a surface may also comprise a protective or passivating layer that can reduce or minimize non-specific attachment of non-capture components (e.g., analyte molecules, binding ligands) to the binding surface during the assay which may lead to false positive signals during detection or to loss of signal. Examples of materials that may be utilized in certain embodiments to form passivating layers include, but are not limited to: polymers, such as poly(ethylene glycol), that repel the non-specific binding of proteins; naturally occurring proteins with this property, such as serum albumin and casein; surfactants, e.g., zwitterionic surfactants, such as sulfobetaines; naturally occurring long-chain lipids; and nucleic acids, such as salmon sperm DNA.

One embodiment utilizes proteinaceous capture components. As is known in the art, any number of techniques may be used to attach a proteinaceous capture component to a wide variety of solid surfaces. "Protein" or "proteinaceous" in this context includes proteins, polypeptides, peptides, including, for example, enzymes, and antibodies. A wide variety of techniques are known to add reactive moieties to proteins, for example, the method outlined in U.S. Pat. No. 5,620,850. The attachment of proteins to surfaces is known, for example, see Heller, Acc. Chem. Res. 23:128 (1990), and many other similar references.

In some embodiments, the capture component (or binding ligand) may comprise Fab' fragments. The use of Fab' fragments as opposed to whole antibodies may help reduce non-specific binding between the capture component and the binding ligand. In some cases, the Fc region of a capture component (or binding ligand) may be removed (e.g., proteolytically). In some cases, an enzyme may be used to remove the Fc region (e.g., pepsin, which may produce F(ab')$_2$ fragments and papain, which may produce Fab fragments). In some instances, the capture component may be attached to a binding surface using amines or may be modified with biotin (e.g., using NHS-biotin) to facilitate binding to an avidin or streptavidin coated capture object surface. F(ab')$_2$ fragments may be subjected to a chemical reduction treatment (e.g., by exposure to 2-mercaptoethylamine) to, in some cases, form two thiol-bearing Fab' fragments. These thiol-bearing fragments can then be attached via reaction with a Michael acceptor such as maleimide. For example, the Fab' fragments may then be treated with a reagent (e.g., maleimide-biotin) to attach at least one biotin moiety (i.e., biotinylated) to facilitate attachment to streptavidin-coated surfaces as described above.

Certain embodiments utilize nucleic acids as the capture component, for example for when the analyte molecule is a nucleic acid or a nucleic acid binding protein, or when the it is desired that the capture component serve as an aptamer for binding a protein, as is well known in the art.

According to one embodiment, each binding surface comprises a plurality of capture components. The plurality of capture components, in some cases, may be distributed randomly on the binding surface like a "lawn." Alternatively, the capture components may be spatially segregated into distinct region(s) and distributed in any desired fashion.

Binding between the capture component and the analyte molecule, in certain embodiments, is specific, e.g., as when the capture component and the analyte molecule are complementary parts of a binding pair. In certain such embodiments, the capture component binds both specifically and directly to the analyte molecule. By "specifically bind" or "binding specificity," it is meant that the capture component binds the analyte molecule with specificity sufficient to differentiate between the analyte molecule and other components or contaminants of the test sample. For example, the capture component, according to one embodiment, may be an antibody that binds specifically to some portion of an analyte molecule (e.g., an antigen). The antibody, according to one embodiment, can be any antibody capable of binding specifically to an analyte molecule of interest. For example, appropriate antibodies include, but are not limited to, monoclonal antibodies, bispecific antibodies, minibodies, domain antibodies, synthetic antibodies (sometimes referred to as antibody mimetics), chimeric antibodies, humanized antibodies, antibody fusions (sometimes referred to as "antibody conjugates"), and fragments of each, respectively. As another example, the analyte molecule may be an antibody and the capture component may be an antigen.

According to one embodiment in which an analyte particle is a biological cell (e.g., mammalian, avian, reptilian, other vertebrate, insect, yeast, bacterial, cell, etc.), the capture component may be a ligand having specific affinity for a cell surface antigen (e.g., a cell surface receptor). In one embodiment, the capture component is an adhesion molecule receptor or portion thereof, which has binding specificity for a cell adhesion molecule expressed on the surface of a target cell type. In use, the adhesion molecule receptor binds with an adhesion molecule on the extracellular surface of the target cell, thereby immobilizing or capturing the cell. In one embodiment in which the analyte particle is a cell, the capture component is fibronectin, which has specificity for, for example, analyte particles comprising neural cells.

In some embodiments, as will be appreciated by those of ordinary skill in the art, it is possible to detect analyte molecules using capture components for which binding to analyte molecules that is not highly specific. For example, such systems/methods may use different capture components such as, for example, a panel of different binding ligands, and detection of any particular analyte molecule is determined via a "signature" of binding to this panel of binding ligands, similar to the manner in which "electronic noses" work. This may find particular utility in the detection of certain small molecule analytes. In some embodiments, the binding affinity between analyte molecules and capture components should be sufficient to remain bound under the conditions of the assay, including wash steps to remove molecules or particles that are non-specifically bound. In some cases, for example in the detection of certain biomolecules, the binding constant of the analyte molecule to its complementary capture component may be between at least about $10^4$ and about $10^6$ $M^{-1}$, at least about $10^5$ and about $10^9$ $M^{-1}$, at least about $10^7$ and about $10^9$ $M^{-1}$, greater than about $10^9$ $M^{-1}$, or greater.

Binding Ligands and Precursor Labeling Agents/Labeling Agent

In some embodiment, the assay may comprise the use of at least one binding ligand. Binding ligands may be selected from any suitable molecule, particle, or the like, as discussed more below, able to associate with an analyte molecule and/or to associate with another binding ligand. Certain binding ligands can comprise a component that is able to facilitate detection, either directly (e.g., via a detectable moiety) or indirectly. A component may facilitate indirect detection, for example, by converting a precursor labeling agent molecule into a labeling agent molecule (e.g., an agent that is detected in an assay). In some embodiments, the binding ligand may comprise an enzymatic component (e.g., horseradish peroxidase, beta-galactosidase, alkaline phosphatase, etc). A first type of binding ligand may or may not be used in conjunction with additional binding ligands (e.g., second type, etc.), as discussed herein.

In some embodiments, the plurality of analyte molecules (e.g., in some cases, immobilized with respect to a capture object) may be exposed to a plurality of binding ligands such that a binding ligand associates with at least some of the plurality of analyte molecules. In some cases, greater than about 80%, greater than about 85%, greater than about 90%, greater than about 95%, greater than about 97%, greater than about 98%, greater than about 99%, or more, analyte molecules associate with a binding ligand.

For the capture step, the choice of bead concentration may depend on several competing factors. For example, it can be advantageous if sufficient beads are present to capture most of the target analyte from thermodynamic and kinetic perspectives. As an exemplary illustration, thermodynamically, 200,000 beads in 100 µL that each have about 80,000 capture components (e.g. antibodies) bound to correlates to an antibody concentration of about 0.3 nM, and the antibody-protein equilibrium at that concentration may give rise to a relatively high capture efficiency of target analyte molecules in certain cases (e.g. >70%). Kinetically, for 200,000 beads dispersed in 100 µL, the average distance between beads can be estimated to be about 80 µm. Proteins the size of TNF-α and PSA (17.3 and 30 kDa, respectively), as exemplary analyte molecules, for example, will typically tend to diffuse 80 µm in less than 1 min, such that, over a 2 hour incubation, capture of such analyte molecules will tend not to be limited kinetically. In addition, it can also be advantageous to provide sufficient beads loaded onto the arrays to limit Poisson noise to a desired or acceptable amount. Considering as an example a situation where 200,000 beads in a in 10 µL volume are loaded onto an array, typically about 20,000-30,000 beads may become trapped in femtoliter sized wells of the array. For a typical background signal (e.g. due to non specific binding, etc.) of 1% active beads, this loading would be expected to result in a background signal of 200-300 active beads detected, corresponding to a coefficient of variation (CV) from Poisson noise of 6-7%, which may be acceptable in typical embodiments. However, bead concentrations above certain concentrations may be undesirable in certain cases in that they may lead to: a) increases in non-specific binding that may reduce signal-to-background; and/or b) undesirably low ratios of analyte-to-bead such that the fraction of active beads is too low, resulting in high CVs from Poisson noise. In certain embodiments, considering a balance of factors such as those discussed above, providing about 200,000 to 1,000,000 beads per 100 µL of test sample may be desirable or, in certain cases optimal, for performing certain assays of the invention.

For embodiments of the inventive assay employing one or more binding ligand(s) to label the captured analyte molecules, it may be advantageous to, in certain instances, adjust the concentrations used to yield desirable or optimal performance. For example, considering an embodiment involving an analyte molecule that is a protein (captured protein) and employing a first binding ligand comprising a detection antibody and a second binding ligand comprising an enzyme conjugate (e.g. SβG), the concentrations of detection antibody and enzyme conjugate (SβG) used to label the captured protein may in some cases be limited or minimized to yield an acceptable background signal (e.g. 1% or less) and Poisson noise. The choice of the concentrations of detection antibody and enzyme conjugate (SβG) used to label the captured protein can be factors in improving the performance of or optimizing certain of the inventive assay methods. In certain cases, it may be desirable for only a fraction of the capture proteins to be labeled so as to avoid saturating signals produced by the assay. For example, for a particular assay where background levels observed are equivalent to ~1-2 fM of target protein, such that the ratio of analyte to bead may be about 0.3-0.6, the number of active beads may be in the range of about 25-40% if every protein was labeled with an enzyme, which may be higher than desirable in some cases. To produce background signals that may be closer to a lower end of the dynamic range for a digital detection assay—considering e.g. that in certain cases 1% active beads may provide a reasonable noise floor for background in digital detection assays of the invention—appropriate labeling of the captured protein can potentially be achieved by kinetic control of the labeling steps, either by limiting or minimizing the concentrations of both labeling reagents or by using shorter incubation times. For example, in an embodiment where label concentrations are minimized, use of a standard ELISA incubation time may provide acceptable results; e.g. using a total assay time of ~6 h. This length of time may be acceptable for testing that tolerates a daily turnaround time for samples. For shorter turnaround times of, for example, <1 hour (e.g., for point-of-care applications), the assay could be performed with shorter incubations with higher concentrations of labels.

In some embodiments, more than one type of binding ligand may be used. In some embodiments, a first type of binding ligand and a second type of binding ligand may be provided. In some instances, at least two, at least three, at least four, at least five, at least eight, at least ten, or more, types of binding ligands may be provided. When a plurality of capture objects, some of which are associated with at least one analyte molecule, are exposed to a plurality of types of binding ligand, at least some of the plurality of immobilized analyte molecules may associate with at least one of each type of binding ligand. The binding ligands may be selected such that they interact with each other in a variety of different manners. In a first example, the first type of binding ligand may be able to associate with an analyte molecule and the second type of binding ligand may be able to associate with the first type of binding ligand. In such embodiments, the first type of binding ligand may comprise a first component which aids in association of the analyte molecule and a second component which aids in association of the second type of binding ligand with the first type of binding ligand. In a particular embodiment, the second component is biotin and the second type of binding ligand comprises an enzyme or an enzymatic component which associates with the biotin.

As another example, both the first type of binding ligand and the second type of binding ligand may associate directly with an analyte molecule. Without being bound by theory or any particular mechanism, the association of both the first type and the second type of binding ligand may provide additional specificity and reliability in performing an assay, by identifying only locations which are determined to contain both the first type of binding ligand and/or the second type of binding ligand (e.g., either through direct or indirect detection) as containing an analyte molecule. Such assay methods may reduce the number of false positives caused by non-specific binding as locations that are found to only have a single type of binding ligand (e.g., only the first type of labeling agent or the second type of labeling agent) would be not be considered or counted as a location comprising an analyte molecule. The first type of binding ligand may comprise a first type of enzymatic component and the second type of binding ligand may comprise a second type of enzymatic component which differs from the first type of enzymatic component. A capture object comprising an analyte molecule, the first type of binding ligand, and the second type of binding ligand may be exposed to a first type of precursor labeling agent which is converted to a first type of labeling agent (e.g., comprising a first measurable property) upon exposure to the first type of enzymatic component and a second type of precursor labeling agent which is converted to a second type of labeling agent (e.g., comprising a measurable property which is distinguishable from the first measurable property) upon exposure to the second type of enzymatic component. Therefore, only locations which are determined to contain the first type of labeling agent and the second type of labeling agent are determined to contain an analyte molecule. As another example, the first type of binding ligand and the second type of binding ligand may each incorporate a component (e.g., such as a DNA label) and a third type of binding ligand may comprise two components complimentary to the components of the first type and second type of binding ligands (e.g., two types of complimentary DNA labels), wherein the third type of binding ligand also comprises an molecule or moiety for direct or indirect detection (e.g., the presence of the third type of binding ligand in a reaction vessel is required to determine the presence or absence of an analyte molecule in a location). When both the first type of binding ligands and the second types of binding ligands are present in substantially close proximity to each other (e.g., via association with an analyte molecule) association of the third type of binding ligand may occur, and therefore, for detection of the analyte molecule. More information regarding the use of more than one type of binding ligand in a manner which may reduce certain negative affects associated with non-specific binding, are described in commonly owned U.S. patent application Ser. No. 12/731,135, entitled "Ultra-Sensitive Detection of Molecules using Dual Detection Methods" by Duffy et al., filed Mar. 24, 2010; and International Patent Application Ser. No. (not yet determined), entitled "Ultra-Sensitive Detection of Molecules using Dual Detection Methods" by Duffy et al., filed Mar. 1, 2011, (Attorney Docket No. Q0052.70012WO00), incorporated by reference.

The following examples are included to demonstrate various features of the invention. Those of ordinary skill in the art should, in light of the present disclosure, will appreciate that many changes can be made in the specific embodiments which are disclosed while still obtaining a like or similar result without departing from the scope of the invention as defined by the appended claims. Accordingly, the following examples are intended only to illustrate certain features of the present invention, but do not necessarily exemplify the full scope of the invention.

Example 1

The following example describes materials used in Examples 2-10. Optical fiber bundles were purchased from Schott North America (Southbridge, Mass.). Non-reinforced gloss silicone sheeting was obtained from Specialty Manufacturing (Saginaw, Mich.). Hydrochloric acid, anhydrous ethanol, and molecular biology grade Tween-20 were purchased from Sigma-Aldrich (Saint Louis, Mo.). 2.7-μm-diameter carboxyl-terminated magnetic beads were purchased from Varian, Inc. (Lake Forest, Calif.). 1-ethyl-3-(3-dimethylaminopropyl) carbodiimide hydrochloride (EDC), N-hydroxysulfosuccinimide (NHS), and SuperBlock® T-20 Blocking Buffer were purchased from Thermo Scientific (Rockford, Ill.). Streptavidin-β-galactosidase (SβG) was purchased from Invitrogen, Sigma-Aldrich, or conjugated in house using standard protocols. Resorufin-β-D-galactopyranoside (RGP) was purchased from Invitrogen (Carlsbad, Calif.). The fiber polisher and polishing consumables were purchased from Allied High Tech Products (Rancho Dominguez, Calif.). Monoclonal capture antibody to PSA, monoclonal detection antibody to PSA, and purified PSA were purchased from BiosPacific. The Chromalink™ biotinylation reagent was purchased from Solulink, Inc (San Diego, Calif.). Purified DNA was purchased from Integrated DNA Technologies.

Example 2

The following describes a non-limiting example of the preparation of 2.7-um-diameter magnetic beads functionalized with biotin for capture of the exemplary analyte, SβG. Beads functionalized with DNA capture probe (5'-NH$_2$/C12-GTT GTC AAG ATG CTA CCG TTC AGA G-3') were prepared according to the manufacturer's instructions. These beads were incubated with 1 μM of biotinylated complementary DNA (5'-biotin-C TCT GAA CGG TAG CAT CTT GAC AAC-3') overnight (16 h) in TE buffer containing 0.5M NaCl and 0.01% Tween-20. After incubation, the beads were washed three times in PBS buffer containing 0.1% Tween-20. The bead stock was distributed into a microtiter plate giving 400,000 beads per well in 100 μL. The buffer was aspirated from the microtiter plate wells, the beads were resuspended and incubated with various concentrations of SβG in Superblock containing 0.05% Tween-20 for 5 h. The beads were then separated and washed six times with 5×PBS buffer containing 0.1% Tween-20.

In an alternative embodiment, a bead concentration of 200,000 beads per 100 μL of SβG target solution was used. Beads were resuspended and incubated with various concentrations of SβG in target solutions diluted in SuperblockSuperBlock containing 0.05% Tween-20 for 54 h. 100 μL of the various target solutions were aliquotted into a microtiter plate. The beads were then separated with a microtiter plate magnet and washed six times with 5×PBS buffer containing 0.1% Tween-20. For detection, the beads were resuspended in 10 μL of PBS containing 0.1% Tween-20, and the aliquots were loaded onto a femtoliter-volume well array.

Example 3

The following describes a non-limiting example of the preparation of microwells arrays. Optical fiber bundles approximately 5-cm long were sequentially polished on a polishing machine using 30-, 9-, and 1-micron-sized diamond lapping films. The polished fiber bundles were chemically etched in a 0.025 M HCl solution for 130 seconds, and then immediately submerged into water to quench the reaction. On average, the wells etch at a rate of approximately 1.5 to 1.7 μm per minute. Therefore, wells of 3.25 um depth are produced in about 115 to 130 s. To remove impurities from etching, the etched fibers were sonicated for 5 s and washed in water for 5 min. The fibers were then dried under vacuum and exposed to air plasma for 5 min to clean and activate the glass surface. The arrays were silanized for 30 minutes in a 2% solution of silane to make the surfaces hydrophobic. In some cases, the dimensions of the wells (e.g., 3.25±0.5 μm) were configured for retaining single beads in wells while maintaining good seals.

Example 4

The following describes a non-limiting example of the loading of beads into microwells. Prior to loading of the beads into the etched wells, the beads may be exposed to the fluid sample comprising the analyte molecules. To apply the solution of beads to the etched wells in a fiber bundle, clear PVC tubing (1/16" I.D. 1/8" O.D.) and clear heat shrink (3/16" ID) were cut into approximately 1 cm long. A piece of PVC tubing was first place on the etched end of a fiber bundle to create a reservoir to hold the bead solution, followed by the application of heat shrink around the interface between the PVC tubing and fiber bundle to provide a tight seal. 10 uL of the concentrated bead solution was pipetted into the reservoir created by the PVC tubing. The fiber bundle was then centrifuged at 3000 rpm (~1300 g) for 10 minutes to force the beads into the etched wells. The PVC tubing/heat shrink assembly was removed after centrifugation. The distal end of the fiber bundle was dipped in PBS solution to wash off excess bead solution, followed by swabbing the surface with deionized water. In embodiments where the bead concentrations was 200,000 per 10 μL, this typically resulted in 40-60% of wells in a 50,000-well array being occupied by a single bead.

Example 5

The following describes a non-limiting example of the loading and detection of beads and enzyme-labeled beads in microwell arrays. A custom-built imaging system containing a mercury light source, filter cubes, objectives, and a CCD camera was used for acquiring fluorescence images. Fiber bundle arrays were mounted on the microscope stage using a custom fixture. A droplet of β-galactosidase substrate (RPG) was placed on the silicone gasket material, and put into contact with the distal end of the fiber array. The precision mechanical platform moved the silicone sheet into contact with the distal end of the etched optical fiber array, creating an array of isolated femtoliter reaction vessels. Fluorescence images were acquired at 577 nm with an exposure time 1011 ms. Five frames (at 30 seconds per frame) were taken for each fiber bundle array. The fluorescent images were analyzed using image analysis software to determine the presence or absence of enzymatic activity within each well of the microwell array. The data was analyzed using a developed image processing software using MathWorks MATLAB and MathWorks Image Processing toolbox. The software aligns acquired image frames, identifies reaction vessel positions, locates reaction vessels with beads and measures the change in reaction vessel intensity over a predefined time period. Reaction vessels containing beads with sufficient intensity growth over all data frames are counted and the final number of active reaction vessels is reported as a percentage of all identified reaction vessels As well as fluorescence, the arrays were imaged with white light to identify those wells that contain beads. After acquiring the fluorescence images, the distal (sealed) end of the fiber bundle arrays were illuminated with white light and imaged on the CCD camera. Due to scattering of light by the beads, those wells that contained a bead appeared brighter in the image than wells without beads. Beaded wells were identified using this method by software.

Example 6

The following non-limiting method describes extending the dynamic range of single molecule measurements. The experiment described above in Example 5 was repeated across a wide range of enzyme concentrations (e.g., see Table 2 for range of concentrations). The images generated in this experiment were analyzed in different ways depending on the concentration tested. For example, as described in the above in the detailed description, when the percentage of beads associated with at least one analyte molecules (e.g., enzymes) was less than about 50% (or 45%, or 40%, or 35%, etc.) the average molecule per bead was determined by counting the total number of "on" beads. An "on" bead was identified as a well that contained a bead (from the white light image), and whose fluorescence increased in all four consecutive frames after the first frame, and whose overall fluorescence increased by at least 20% from the first frame to the last. The total number of "on" beads may be adjusted using a Poisson distribution adjustment. At high ratios of "on" beads, the average bead signal was determined from the intensity of the second frame captured. The analog-to-digital conversion factor was determined using a sample of known concentration which had an "on" bead percentage between about 30% and about 50%. The results for the samples of known concentration may be plotted on a calibration curve, with aid of a calibration factor. Using the resulting calibration curve, the unknown concentration of analyte molecules in a fluid sample may be determined. For example, by addressing at least some of the plurality of locations containing at least one bead and determining a measure indicative of the percentage of said locations containing at least one analyte molecule or particle (e.g., the percentage of "on" beads). Depending on the percentage, a measure of the unknown concentration of analyte molecules or particles in the fluid sample may be determined based at least in part on the percentage or based at least in part on a measured intensity of a signal that is indicative of the presence of a plurality of analyte molecules or particles, and by comparison of the value with the calibration curve.

Example 7

The following example describes the preparation and characterization of biotinylated PSA detection antibodies and enzyme conjugates. Detection antibodies were biotinylated using the Chromalink™ biotinylation reagent. This reagent contains a succinimidyl ester group that attaches biotin groups to the antibody via lysine residues, and a bis aryl hydrazone chromophore that allows quantification of the number of biotin molecules per antibody. The average number of biotin groups on the anti-PSA antibody ranged from 7.5 to 9.5. Streptavidin-β-galactosidase (SβG) was conjugated using standard protocols. HPLC characterization of the conjugate indicated that >80% of the conjugate molecules contained one β-galactosidase molecule, with an average of 1.2 enzymes/conjugate. Comparison to molecular weight standards indicated that the average number of streptavidin molecules conjugated to each enzyme molecule was 2.7. As each detection antibody contains multiple biotin groups, it is possible that a single protein molecule bound to a single detection antibody could be bound to multiple enzyme conjugates. Analysis of the fluorescence intensity generated by enzyme-associated beads in the single molecule regime (AMB<0.1) suggests, however, that multiple enzyme conjugates did not bind to single detection antibody molecules: these fluorescent intensities were consistent with the previously-known kinetics of single molecules of β-galactosidase.

Example 8

The following example describes the capture of PSA on magnetic beads and formation of enzyme-labeled immunocomplexes. Beads functionalized with a monoclonal antibody to PSA were prepared according to the manufacturer's instructions. Test solutions (100 μL) were incubated with suspensions of 500,000 magnetic beads for 2 h at 23° C. The beads were then separated and washed three times in 5×PBS and 0.1% Tween-20. The beads were resuspended and incubated with solutions containing detection antibody (~1 nM) for 60 min at 23° C. The beads were then separated and washed three times in 5×PBS and 0.1% Tween-20. The beads were incubated with solutions containing SβG (15 pM) for 30 min at 23° C., separated and washed seven times in 5×PBS and 0.1% Tween-20. The beads were then resuspended in 25 μL of PBS, and 10 μL of the bead solution was loaded onto a femtoliter-volume well array.

Example 9

The following example describes an exemplary system where a combined digital and analog enzyme label detection was carried out using the analysis described above in the context of the second analog analysis embodiment (Equation 8). The SβG binding assay described above in Example 7 and using the methods and apparatus described in the other examples demonstrated an extended dynamic range can be achieved by combining digital and analog determination of AMB. FIG. 13 shows AMB determined from images of populations of biotin-presenting beads that had been incubated with concentrations of SβG ranging from zeptomolar to picomolar. Specifically, FIGS. 13A and 13B show that a broad dynamic range was achieved by combining digital and analog measurements. FIG. 13A shows a plot of AMB as a function of enzyme concentration. The error bars are standard deviations over three replicates. FIG. 13B shows a table including the % active and AMB values as a function of enzyme concentration. AMB was determined using Equation 4 for % active <70% and AMB was determined using Equation 8 for % active >70%. The threshold between analog and digital in this example was between 10 fM and 31.6 fM.

For images with % active beads <70%, $AMB_{digital}$ was determined using Equation 4. All the arrays with <10% active beads were used to determine $I_{single}$, a total of 7566 beads; $I_{single}$ was equal to 298 au. The average fluorescence intensities of beads in images with over 70% active were determined, and $AMB_{analog}$ values were calculated using Equation 8. Because the 0 M SβG concentration yielded no active beads, the lower limit of detection in this experiment could not be calculated using the background plus 3 s.d. method. Using a previously established LOD of 220 zM, and the highest concentration detected in the linear range of this curve, 316 fM, a 6.2-log linear dynamic range for detecting enzyme label was observed. The linear digital dynamic range was 4.7 logs and the analog linear dynamic range was 1.5 logs.

Example 10

Figure 14A:
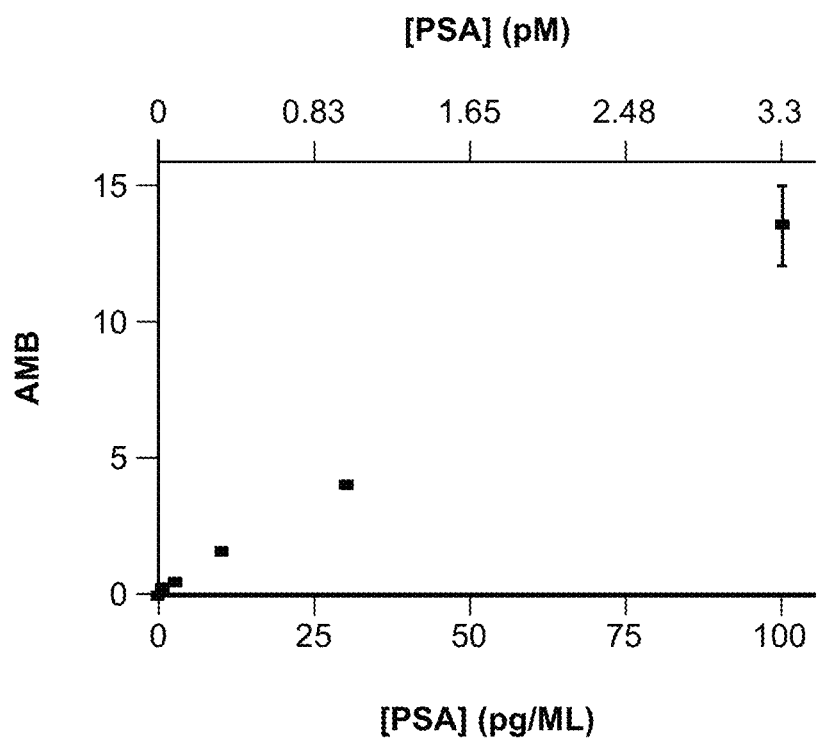
FIGS. 14A and 14B are plots showing a combined digital and analog analysis of PSA samples, according to some embodiments.
Figure 14B:
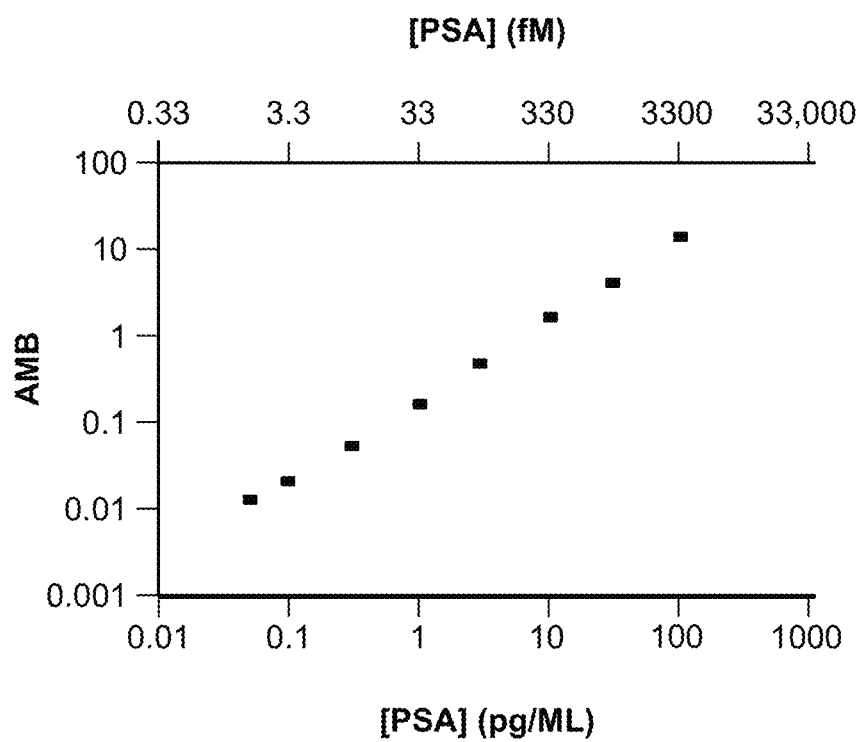

This example describes a combined digital and analog system and method for measuring PSA in serum. The combined digital and analog approach was used for determining concentration of PSA with a wide dynamic range. Clinically, PSA is used to screen for prostate cancer and to monitor for biochemical recurrence of the disease in patients who have undergone surgery to remove the cancer. The PSA levels in the serum of patients who have undergone radical prostatectomy (RP) are known to range from 0.014 pg/mL to over 100 pg/mL. To successfully measure the PSA levels in the majority of patients in a single test requires an assay with 4 logs of dynamic range. The experiments were conducted as described in Example 8. FIGS. 14A and 14B show that by combining digital and analog analyses, the working range of the inventive PSA assay ranged from 0.008 pg/mL to 100 pg/mL, enabling precise quantification of PSA levels in the vast majority of RP patient samples in one pass. Specifically, FIGS. 14A and 14B show combined digital and analog PSA assay results with a 4-log working range and calculated LOD of 0.008 pg/mL. AMB is plotted as a function of PSA concentration in (FIG. 14A) linear-linear space and (FIG. 14B) log-log space. Error bars are shown for all data points based on quadruplicate measurements.

The assay was used to measure the concentration of PSA in the sera of 17 prostate cancer patients collected at 2 to 46 weeks (mean=13.8 weeks) after radical prostatectomy surgery. These samples were collected close to surgery in order to push the lower limits of detection of digital ELISA. Here, in order to evaluate the dynamic range of the assay across the intended clinical range, samples collected closer to surgery were tested to capture patients with higher PSA whose cancer could recur. PSA was, however, undetectable in all of these samples using a leading PSA diagnostic test (Siemens). Serum samples were diluted 1:4 in buffer and the AMB was measured using the methods described herein. The concentration of PSA for each sample was determined by reading the AMB off a simultaneously acquired calibration curve similar to FIG. 14B. Table 4 summarizes the AMB and PSA Concentrations determined from these samples, along with the imprecision for signal and concentration given by % CV. PSA was quantified in all of the samples in one experiment. The average PSA concentration in these samples was 33 pg/mL, with a high of 136 pg/mL and a low of 0.4 pg/mL. When combined with previous measurements of PSA in patient who had undergone radical prostatectomy (RP) surgery, the detected concentrations of PSA in clinical samples ranged from 0.46 fM (0.014 pg/mL) to 4.5 µM (136 pg/mL), demonstrating the importance of the good dynamic range provided by the inventive assay of this example.

TABLE 4

Summary of AMB and [PSA] determined for 17 serum samples from post-RP patients[a]

| sample ID | mean AEB | std dev AEB | AEB CV, % | [PSA] (pg/mL) | std dev [PSA] | [PSA] CV, % |
|---|---|---|---|---|---|---|
| S640 | 8.8 | 1.2 | 13 | 41.0 | 7.5 | 18 |
| S641 | 0.87 | 0.08 | 10 | 4.1 | 0.4 | 11 |
| S643 | 0.23 | 0.002 | 1 | 1.1 | 0.01 | 1 |
| S644 | 15.2 | 1.0 | 6 | 136 | 13 | 10 |
| S645 | 1.5 | 0.06 | 4 | 6.1 | 0.2 | 4 |
| S647 | 11.0 | 0.1 | 1 | 80.4 | 1.9 | 2 |
| S648 | 7.4 | 0.3 | 3 | 32.3 | 1.6 | 5 |
| S649 | 1.5 | 0.2 | 11 | 6.1 | 0.6 | 10 |
| S650 | 0.22 | 0.008 | 4 | 1.2 | 0.03 | 2 |
| S651 | 0.50 | 0.02 | 5 | 2.3 | 0.1 | 4 |
| S615 | 12.6 | 1.0 | 8 | 70.7 | 8.6 | 12 |
| S653 | 1.3 | 0.2 | 18 | 5.0 | 0.8 | 16 |
| S616 | 0.44 | 0.05 | 12 | 1.7 | 0.2 | 13 |
| S618 | 13.6 | 0.7 | 5 | 79.2 | 6.2 | 8 |
| S624 | 14.8 | 0.5 | 3 | 88.9 | 4.1 | 5 |
| S627 | 0.098 | 0.003 | 3 | 0.39 | 0.01 | 3 |
| S628 | 0.92 | 0.04 | 5 | 3.7 | 0.15 | 4 |

[a]Standard deviations and CVs were determined over triplicate tests. Sample S644 had an AEB value beyond the range of the calibration curve, but its concentration was determined by extrapolation.

Example 11

Figures 15A, 15B:
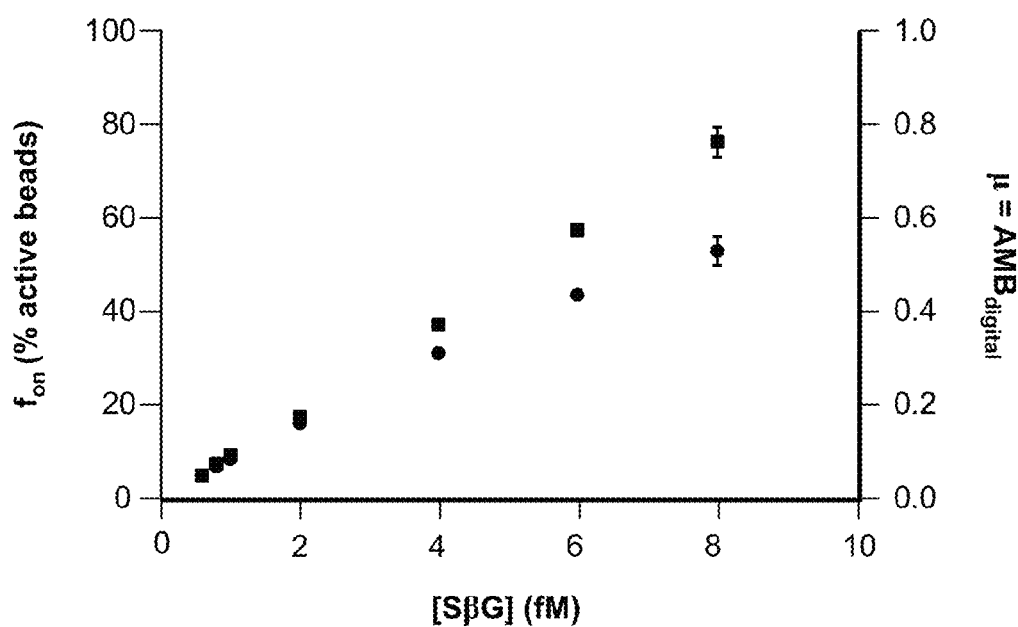
FIG. 15A is a data table that shows conversion of % active beads to $AMB_{digital}$ using Poisson statistics, according to one embodiment.
FIG. 15B shows a plots of % active beads (diamonds) and $AMB_{digital}$ (squares) as a function of enzyme concentration, according to some embodiments.

FIG. 15 demonstrates a non-limiting example of a Poisson distribution analysis in the digital range of a calibration curve using an assay for streptavidin-β-galactosidase (SβG) that resulted in beads having well-defined enzyme/bead ratios. Briefly, beads were functionalized with a biotinylated capture molecule, and these beads were used to capture various concentrations of the SβG enzyme conjugate. The beads were loaded into the femtoliter arrays and, after sealing a solution of RGP into the wells of the array, fluorescence was generated from bound enzymes accumulated in the reaction chambers for 2.5 min, with fluorescent images acquired every 30 s. A white light image of the array was acquired at the end of the experiment. These images were analyzed to identify wells that contained beads (from the white light image) and determine which of those beads had associated bound enzyme molecules (from time-lapsed fluorescent images. FIG. 15B shows that $AMB_{digital}$ determined from Equation 4 maintained a linear response up to 50% active, despite non-linear variation in $f_{on}$. Specifically, FIG. 15 shows (FIG. 15A) conversion of % active beads to $AMB_{digital}$ using Poisson statistics. The center column is the fraction of active beads determined by digital counting as a function of enzyme concentration. The right column is the average enzyme per bead (AMB) determined from % active beads using Equation 4. This conversion accounts statistically for beads associated with multiple enzyme molecules using a digital counting method; (FIG. 15B) shows a plot of % active beads (diamonds) and $AMB_{digital}$ (squares) as a function of enzyme concentration. The % active beads deviates from linearity with increasing concentration as expected from the Poisson distribution. In this experiment, $AMB_{digital}$ was linear with concentration up to about 50% active beads. Error bars were determined from the standard deviation over three measurements.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively.

What is claimed:

1. A system for determining a measure of the concentration of analyte molecules or particles in a fluid sample, comprising:
   an assay substrate comprising a plurality of locations each comprising a binding surface forming or contained within such locations, wherein at least one binding surface comprises at least one analyte molecule or particle immobilized on the binding surface;
   at least one detector configured to address a plurality of the locations, able to produce at least one signal indicative of the presence or absence of an analyte molecule or particle at each location addressed and having an intensity varying with the number of analyte molecules or particles at each location; and
   at least one signal processor configured to determine from the at least one signal the percentage of said locations containing at least one analyte molecule or particle, and further configured to, based upon the percentage, either determine a measure of the concentration of analyte molecules or particles in the fluid sample based at least in part on the number of locations containing at least one analyte molecule or particle, or determine a measure of the concentration of analyte molecules or particles in the fluid sample based at least in part on an intensity level of the at least one signal indicative of the presence of a plurality of analyte molecules or particles.

2. The system of claim 1, wherein the binding surface is contained within such locations.

3. The system of claim 2, wherein the binding surface comprises a plurality of capture objects.

4. The system of claim 3, wherein the plurality of capture objects comprise a plurality of beads.

5. The system of claim 3, wherein the locations addressed are locations which contain at least one capture object.

6. The system of claim 1, wherein when the percentage of said locations containing at least one analyte molecule or particle is less than about 40%, less than about 35%, or less than about 30%, the measure of the concentration of analyte molecules or particles in the fluid sample is based at least in part on the number of locations containing at least one analyte molecule or particle.

7. The system of claim 1, wherein when the percentage of said locations containing at least one analyte molecule or particle is less than about 80%, less than about 75%, or less than about 70%, less than about 65%, or less than about 60%, the measure of the concentration of analyte molecules or particles in the fluid sample is based at least in part on the number of locations containing at least one analyte molecule or particle.

8. The system of claim 1, wherein when the percentage of said locations containing at least one analyte molecule or particle is greater than about 30%, greater than about 35%, greater than about 40%, or greater than about 45%, the measure of the concentration of analyte molecules or particles in the fluid sample is based at least in part on an intensity level of the at least one signal indicative of the presence of a plurality of analyte molecules or particles.

9. The system of claim 1, wherein when the percentage of said locations containing at least one analyte molecule or particle is greater than about 60%, greater than about 65%, greater than about 70%, or greater than about 75%, the measure of the concentration of analyte molecules or particles in the fluid sample is based at least in part on an intensity level of the at least one signal indicative of the presence of a plurality of analyte molecules or particles.

10. The system of claim 1, wherein when the percentage of said locations containing at least one analyte molecule or particle is between about 30% and about 50%, or between about 35% and about 45%, or about 40%, the measure of the concentration of analyte molecules or particles in the fluid sample is an average of the measure of the concentration of analyte molecules or particles in the fluid sample based at least in part on the number of locations containing at least one analyte molecule or particle and the measure of the concentration of analyte molecules or particles in the fluid sample based at least in part on an intensity level of the at least one signal indicative of the presence of a plurality of analyte molecules or particles.

11. The system of claim 1, wherein when the percentage of said locations containing at least one analyte molecule or particle is between about 60% and about 80%, or between about 65% and about 75%, or about 70%, the measure of the concentration of analyte molecules or particles in the fluid sample is an average of the measure of the concentration of analyte molecules or particles in the fluid sample based at least in part on the number of locations containing at least one analyte molecule or particle and the measure of the concentration of analyte molecules or particles in the fluid sample based at least in part on an intensity level of the at least one signal indicative of the presence of a plurality of analyte molecules or particles.

12. The system of claim 1, wherein the plurality of locations comprises a plurality of reaction vessels.

13. The system of claim 12, wherein the average volume of the plurality of reaction vessels is between about 10 attoliters and about 100 picoliters.

14. The system of claim 1, further comprising a plurality of control objects contained within at least a portion of the locations.

15. The system of claim 14, wherein the plurality of control beads are used to identify the orientation of the plurality of locations.

16. The system of claim 14, wherein the plurality of control beads are used to calibrate the at least one detector.

17. The system of claim 14, wherein the plurality of control objects comprise a plurality of beads.

* * * * *